US008951964B2

(12) United States Patent
McDaniel et al.

(10) Patent No.: US 8,951,964 B2
(45) Date of Patent: Feb. 10, 2015

(54) PHENANTHRIDINE MACROCYCLIC HEPATITIS C SERINE PROTEASE INHIBITORS

(75) Inventors: Keith F. McDaniel, Wauconda, IL (US); Hui-Ju Chen, Grayslake, IL (US); Jason P. Shanley, Chicago, IL (US); David J. Grampovnik, Waukegan, IN (US); Brian Green, Wonder Lake, IL (US); Timothy Middleton, Elkhorn, WI (US); Todd Hopkins, Lake Villa, IL (US); Yat Sun Or, Watertown, MA (US)

(73) Assignees: AbbVie Inc., North Chicago, IL (US); Enanta Pharmaceuticals, Inc., Watertown, MA (US)

( * ) Notice: Subject to any disclaimer, the term of this patent is extended or adjusted under 35 U.S.C. 154(b) by 92 days.

(21) Appl. No.: 13/339,448

(22) Filed: Dec. 29, 2011

(65) Prior Publication Data
US 2012/0295842 A1 Nov. 22, 2012

Related U.S. Application Data

(60) Provisional application No. 61/428,488, filed on Dec. 30, 2010, provisional application No. 61/449,331, filed on Mar. 4, 2011.

(51) Int. Cl.
*A61K 38/00* (2006.01)
*A01N 37/18* (2006.01)
*C07D 487/04* (2006.01)

(52) U.S. Cl.
CPC ................................... *C07D 487/04* (2013.01)
USPC .......................................................... 514/4.3

(58) Field of Classification Search
None
See application file for complete search history.

(56) References Cited

U.S. PATENT DOCUMENTS

| | | | |
|---|---|---|---|
| 5,831,002 A | 11/1998 | Haupt et al. |
| 6,268,207 B1 | 7/2001 | Bailey |
| 6,323,180 B1 | 11/2001 | Llinas-Brunet et al. |
| 6,329,379 B1 | 12/2001 | Llinas-Brunet et al. |
| 6,329,417 B1 | 12/2001 | Llinas-Brunet et al. |
| 6,410,531 B1 | 6/2002 | Llinas-Brunet et al. |
| 6,420,380 B2 | 7/2002 | Llinas-Brunet et al. |
| 6,534,523 B1 | 3/2003 | Bailey et al. |
| 6,608,027 B1 | 8/2003 | Tsantrizos et al. |
| 6,642,204 B2 | 11/2003 | Llinas-Brunet et al. |
| 6,653,295 B2 | 11/2003 | Glunz et al. |
| 6,699,855 B2 | 3/2004 | Zhang et al. |
| 6,727,366 B2 | 4/2004 | Han et al. |
| 6,767,991 B1 | 7/2004 | Llinas-Brunet et al. |
| 6,774,212 B2 | 8/2004 | Han |
| 6,803,374 B2 | 10/2004 | Priestley et al. |
| 6,846,806 B2 | 1/2005 | Priestley |
| 6,867,185 B2 | 3/2005 | Campbell et al. |
| 6,869,964 B2 | 3/2005 | Campbell et al. |
| 6,872,805 B2 | 3/2005 | Campbell et al. |
| 6,878,722 B2 | 4/2005 | Campbell et al. |
| 6,939,854 B2 | 9/2005 | Priestley |
| 6,995,174 B2 | 2/2006 | Wang et al. |
| 7,037,911 B2 | 5/2006 | Zhang |
| 7,041,698 B2 | 5/2006 | Ripka et al. |
| 7,091,184 B2 | 8/2006 | Llinas-Brunet et al. |
| 7,112,601 B2 | 9/2006 | Glunz et al. |
| 7,119,072 B2 | 10/2006 | Llinas-Brunet et al. |
| 7,122,627 B2 | 10/2006 | Priestley et al. |
| 7,132,504 B2 | 11/2006 | Scola et al. |
| 7,135,462 B2 | 11/2006 | Scola et al. |
| 7,153,848 B2 | 12/2006 | Hudyma et al. |
| 7,157,424 B2 | 1/2007 | Chen et al. |
| 7,173,004 B2 | 2/2007 | McPhee et al. |
| 7,176,208 B2 | 2/2007 | Nakajima et al. |
| 7,183,302 B2 | 2/2007 | Romine et al. |
| 7,189,844 B2 | 3/2007 | Gallou et al. |
| 7,309,708 B2 | 12/2007 | Tu et al. |
| 7,323,447 B2 | 1/2008 | Sin et al. |
| 7,348,425 B2 | 3/2008 | Hudyma et al. |
| 7,368,452 B2 | 5/2008 | Nakajima et al. |
| 7,375,218 B2 | 5/2008 | Gallou |
| 7,491,794 B2 | 2/2009 | Blatt et al. |
| 7,504,378 B2 | 3/2009 | Llinas-Brunet et al. |
| 7,544,798 B2 | 6/2009 | Busacca et al. |
| 7,566,719 B2 | 7/2009 | Nakajima et al. |
| 7,592,419 B2 | 9/2009 | Venkatraman et al. |
| 7,601,709 B2 | 10/2009 | Miao et al. |
| 7,608,590 B2 | 10/2009 | Rosenquist et al. |

(Continued)

FOREIGN PATENT DOCUMENTS

| | | |
|---|---|---|
| EP | 1437362 A1 | 7/2004 |
| EP | 1455809 | 6/2011 |

(Continued)

OTHER PUBLICATIONS

International Search Report of PCT/US2011/067701.
International Search Report for corresponding PCT International Application No. PCT/US09/05082 dated Apr. 1, 2010.
Lu, Liangjun, et al.: "Mutations Conferring Resistance to a Potent Hepatitis C Virus Serine Protease Inhibitor in Vitro," Antimicrobial Agents and Chemotherapy, Jun. 2004, vol. 48, No. 6, pp. 2260-2266.
A. Johansson et al., "Acyl Sulfonamides as Potent protease Inhibitors of the Hepatitis C Virus Full-Length NS3 (Protease-Helicase/NTPase): A Comparative Study of Different C-Terminals", Bioorganic & Medicinal Chemistry, vol. 11, pp. 2551-2568 (2003).
N. Goudreau et al., "NMR Structural Characterization of Peptide Inhibitors Bound to the Hepatitis C Virus NS3 Protease: Design of a New P2 Substituent", J. Med. Chem., vol. 47, pp. 123-132 (2004).
N. Goudreau et al., "The terapeutic potential of NS3 protease inhibitors in HCV infection", Expert Opin. Investig. Drugs, 14(9), pp. 1129-1144 (2005).

(Continued)

*Primary Examiner* — Thomas S Heard
(74) *Attorney, Agent, or Firm* — Edwards Wildman Palmer LLP; Jeffrey D. Hsi; Stephen W. Rafferty

(57) ABSTRACT

The present invention relates to novel macrocyclic compounds and methods of treating a hepatitis C infection in a subject in need of such therapy with said macrocyclic compounds. The present invention further relates to pharmaceutical compositions comprising the compounds of the present invention, or pharmaceutically acceptable salts, esters, or prodrugs thereof, in combination with a pharmaceutically acceptable carrier or excipient.

20 Claims, No Drawings

(56) References Cited

U.S. PATENT DOCUMENTS

| | | |
|---|---|---|
| 7,642,235 B2 | 1/2010 | Llinas-Brunet et al. |
| 7,642,339 B2 | 1/2010 | Chaudhary et al. |
| 7,659,245 B2 | 2/2010 | Simmen et al. |
| 7,687,459 B2 | 3/2010 | Niu et al. |
| 7,741,281 B2 | 6/2010 | D'Andrea et al. |
| 7,763,584 B2 | 7/2010 | Wang et al. |
| 7,772,180 B2 | 8/2010 | Sin et al. |
| 7,772,183 B2 | 8/2010 | Carini et al. |
| 7,829,665 B2 | 11/2010 | Blatt et al. |
| 2002/0016442 A1 | 2/2002 | Llinas-brunet et al. |
| 2002/0037998 A1 | 3/2002 | Llinas-Brunet et al. |
| 2002/0111313 A1 | 8/2002 | Campbell et al. |
| 2003/0181363 A1 | 9/2003 | Llinas-Brunet et al. |
| 2003/0186895 A1 | 10/2003 | Llinas-Brunet et al. |
| 2003/0187018 A1 | 10/2003 | Llinas-Brunet et al. |
| 2003/0191067 A1 | 10/2003 | Llinas-Brunet et al. |
| 2003/0224977 A1 | 12/2003 | Llinas-Brunet et al. |
| 2003/0232386 A1 | 12/2003 | Shah et al. |
| 2004/0002448 A1 | 1/2004 | Tsantrizos et al. |
| 2004/0038872 A1 | 2/2004 | Campbell et al. |
| 2004/0048802 A1 | 3/2004 | Ripka et al. |
| 2004/0058982 A1 | 3/2004 | Harris |
| 2004/0106559 A1 | 6/2004 | Wang et al. |
| 2004/0180815 A1 | 9/2004 | Nakajima et al. |
| 2004/0229776 A1 | 11/2004 | Chen et al. |
| 2004/0229777 A1 | 11/2004 | Cerreta et al. |
| 2004/0229818 A1 | 11/2004 | Llinas-Brunet |
| 2004/0248779 A1 | 12/2004 | Dersch et al. |
| 2004/0248806 A1 | 12/2004 | Temsamani et al. |
| 2004/0266668 A1 | 12/2004 | Nakajima et al. |
| 2005/0020503 A1 | 1/2005 | Llinas-Brunet et al. |
| 2005/0049187 A1 | 3/2005 | Brandenburg et al. |
| 2005/0065073 A1 | 3/2005 | Wu et al. |
| 2005/0075279 A1 | 4/2005 | Llinas-Brunet et al. |
| 2005/0080005 A1 | 4/2005 | Llinas-Brunet et al. |
| 2005/0090432 A1 | 4/2005 | McPhee et al. |
| 2005/0119168 A1 | 6/2005 | Venkatraman et al. |
| 2005/0143316 A1 | 6/2005 | Tu et al. |
| 2005/0148085 A1 | 7/2005 | Larsen |
| 2005/0153877 A1 | 7/2005 | Miao et al. |
| 2005/0153900 A1 | 7/2005 | Velazquez et al. |
| 2005/0164921 A1 | 7/2005 | Njoroge et al. |
| 2005/0192212 A1 | 9/2005 | Llinas-Brunet et al. |
| 2005/0209135 A1 | 9/2005 | Busacca et al. |
| 2005/0214366 A1 | 9/2005 | Harris |
| 2005/0215423 A1 | 9/2005 | Brenner et al. |
| 2005/0222045 A1 | 10/2005 | Auvin et al. |
| 2005/0267018 A1 | 12/2005 | Blatt et al. |
| 2005/0267151 A1 | 12/2005 | Busacca et al. |
| 2006/0009667 A1 | 1/2006 | Herweck et al. |
| 2006/0019905 A1 | 1/2006 | Bailey et al. |
| 2006/0046965 A1 | 3/2006 | Bailey et al. |
| 2006/0063915 A1 | 3/2006 | Gallou et al. |
| 2006/0063916 A1 | 3/2006 | Gallou |
| 2006/0068007 A1 | 3/2006 | Li et al. |
| 2006/0089300 A1 | 4/2006 | Llinas-Brunet et al. |
| 2006/0122123 A1 | 6/2006 | Chaudhary et al. |
| 2006/0166893 A1 | 7/2006 | Auvin et al. |
| 2006/0172950 A1 | 8/2006 | Wang et al. |
| 2006/0199773 A1 | 9/2006 | Sausker et al. |
| 2006/0205638 A1 | 9/2006 | Busacca et al. |
| 2006/0257980 A1 | 11/2006 | Li |
| 2006/0258868 A1 | 11/2006 | Bailey et al. |
| 2006/0275366 A1 | 12/2006 | Malcolm et al. |
| 2006/0276405 A1 | 12/2006 | Albrecht |
| 2006/0276407 A1 | 12/2006 | Albrecht et al. |
| 2006/0281688 A1 | 12/2006 | Zhang et al. |
| 2007/0004635 A1 | 1/2007 | Albrecht et al. |
| 2007/0010431 A1 | 1/2007 | Malcolm et al. |
| 2007/0010455 A1 | 1/2007 | Hewawasam et al. |
| 2007/0060510 A1 | 3/2007 | Nakajima et al. |
| 2007/0060565 A1 | 3/2007 | Meanwell et al. |
| 2007/0072809 A1 | 3/2007 | Cho et al. |
| 2007/0078081 A1 | 4/2007 | Casarez et al. |
| 2007/0078122 A1 | 4/2007 | Bergstrom et al. |
| 2007/0093414 A1 | 4/2007 | Carini et al. |
| 2007/0099825 A1 | 5/2007 | D'Andrea et al. |
| 2007/0161575 A1 | 7/2007 | Miao et al. |
| 2007/0179167 A1 | 8/2007 | Cottrell et al. |
| 2007/0184024 A1 | 8/2007 | Meanwell et al. |
| 2007/0185083 A1 | 8/2007 | Bergstrom et al. |
| 2007/0237818 A1 | 10/2007 | Malcolm et al. |
| 2007/0243166 A1 | 10/2007 | Llinas-Brunet et al. |
| 2007/0249637 A1 | 10/2007 | Collins et al. |
| 2007/0258947 A1 | 11/2007 | Njoroge et al. |
| 2007/0270405 A1 | 11/2007 | Bender et al. |
| 2007/0270406 A1 | 11/2007 | Gentles et al. |
| 2007/0275930 A1 | 11/2007 | Gentles et al. |
| 2007/0281884 A1 | 12/2007 | Sun et al. |
| 2007/0281885 A1 | 12/2007 | Sun et al. |
| 2007/0287664 A1 | 12/2007 | Ralston et al. |
| 2007/0287694 A1 | 12/2007 | Yeung et al. |
| 2007/0299078 A1 | 12/2007 | Niu et al. |
| 2008/0008681 A1 | 1/2008 | Niu et al. |
| 2008/0014173 A1 | 1/2008 | Scola et al. |
| 2008/0032936 A1 | 2/2008 | Gai et al. |
| 2008/0038225 A1 | 2/2008 | Sun et al. |
| 2008/0039375 A1 | 2/2008 | Moore et al. |
| 2008/0039470 A1 | 2/2008 | Niu et al. |
| 2008/0045536 A1 | 2/2008 | Vaccaro et al. |
| 2008/0107623 A1 | 5/2008 | D'Andrea et al. |
| 2008/0107624 A1 | 5/2008 | D'Andrea et al. |
| 2008/0107625 A1 | 5/2008 | D'Andrea et al. |
| 2008/0108632 A1 | 5/2008 | Lin et al. |
| 2008/0119461 A1 | 5/2008 | Sin et al. |
| 2008/0145334 A1 | 6/2008 | Wang et al. |
| 2008/0146537 A1 | 6/2008 | Bender et al. |
| 2008/0152619 A1 | 6/2008 | Sin et al. |
| 2008/0152622 A1 | 6/2008 | Nakajima et al. |
| 2008/0159982 A1 | 7/2008 | Wang et al. |
| 2008/0171015 A1 | 7/2008 | Bender et al. |
| 2008/0181868 A1 | 7/2008 | Sun et al. |
| 2008/0200497 A1 | 8/2008 | Bailey et al. |
| 2008/0242835 A1 | 10/2008 | Shu |
| 2008/0267916 A1 | 10/2008 | Gai et al. |
| 2008/0267917 A1 | 10/2008 | Niu et al. |
| 2008/0269228 A1 | 10/2008 | Moore et al. |
| 2008/0269502 A1 | 10/2008 | Gantz et al. |
| 2008/0279821 A1 | 11/2008 | Niu et al. |
| 2008/0311077 A1 | 12/2008 | Chaudhary et al. |
| 2009/0005387 A1 | 1/2009 | Niu et al. |
| 2009/0035271 A1 | 2/2009 | Sun et al. |
| 2009/0036708 A1 | 2/2009 | Jia et al. |
| 2009/0041721 A1 | 2/2009 | Niu et al. |
| 2009/0047252 A1 | 2/2009 | Cai et al. |
| 2009/0075869 A1 | 3/2009 | Holloway et al. |
| 2009/0093533 A1 | 4/2009 | Beigelman et al. |
| 2009/0105471 A1 | 4/2009 | Blatt et al. |
| 2009/0111757 A1 | 4/2009 | Lin et al. |
| 2009/0111969 A1 | 4/2009 | Blatt et al. |
| 2009/0111982 A1 | 4/2009 | Blatt et al. |
| 2009/0124808 A1 | 5/2009 | Busacca et al. |
| 2009/0130059 A1 | 5/2009 | Sun et al. |
| 2009/0148407 A1 | 6/2009 | Blatt et al. |
| 2009/0149491 A1 | 6/2009 | Liu et al. |
| 2009/0155209 A1 | 6/2009 | Blatt et al. |
| 2009/0162318 A1 | 6/2009 | Bender et al. |
| 2009/0163706 A1 | 6/2009 | Hildbrand et al. |
| 2009/0169510 A1 | 7/2009 | Blatt et al. |
| 2009/0175822 A1 | 7/2009 | Moore et al. |
| 2009/0176858 A1 | 7/2009 | Niu et al. |
| 2009/0180981 A1 | 7/2009 | Niu et al. |
| 2009/0186869 A1 | 7/2009 | Cottell et al. |
| 2009/0191153 A1 | 7/2009 | Sun et al. |
| 2009/0202480 A1 | 8/2009 | Parsy et al. |
| 2009/0257978 A1 | 10/2009 | Cho et al. |
| 2009/0269305 A1 | 10/2009 | Seiwert et al. |
| 2009/0274648 A1 | 11/2009 | Wang et al. |
| 2009/0274652 A1 | 11/2009 | Sin et al. |
| 2009/0281141 A1 | 11/2009 | Simmen et al. |
| 2009/0285773 A1 | 11/2009 | Sun et al. |
| 2009/0285774 A1 | 11/2009 | Sin et al. |
| 2009/0286814 A1 | 11/2009 | Lin et al. |
| 2009/0286843 A1 | 11/2009 | Blatt et al. |

(56) References Cited

U.S. PATENT DOCUMENTS

| | | | |
|---|---|---|---|
| 2009/0297472 A1 | 12/2009 | Wang et al. |
| 2009/0304626 A1 | 12/2009 | Wang et al. |
| 2009/0304629 A1 | 12/2009 | Miao et al. |
| 2009/0306085 A1 | 12/2009 | Petter et al. |
| 2009/0326194 A1 | 12/2009 | Busacca et al. |
| 2010/0015092 A1 | 1/2010 | Nakajima et al. |
| 2010/0018355 A1 | 1/2010 | Crawford |
| 2010/0022578 A1 | 1/2010 | Raboisson et al. |
| 2010/0028300 A1 | 2/2010 | Llinas-Brunet et al. |
| 2010/0036116 A1 | 2/2010 | Scalone et al. |
| 2010/0041591 A1 | 2/2010 | Niu et al. |
| 2010/0041728 A1 | 2/2010 | Antonov et al. |
| 2010/0068182 A1 | 3/2010 | Huang et al. |
| 2010/0069294 A1 | 3/2010 | Petter et al. |
| 2010/0074890 A1 | 3/2010 | Hagel et al. |
| 2010/0080770 A1 | 4/2010 | Hiebert et al. |
| 2010/0080771 A1 | 4/2010 | Hiebert et al. |
| 2010/0081700 A1 | 4/2010 | Wang et al. |
| 2010/0081713 A1 | 4/2010 | Sharma et al. |
| 2010/0093792 A1 | 4/2010 | Berkenbusch et al. |
| 2010/0099695 A1 | 4/2010 | Liverton et al. |
| 2010/0113440 A1 | 5/2010 | Belfrage et al. |
| 2010/0124545 A1 | 5/2010 | Zhang et al. |
| 2010/0144608 A1* | 6/2010 | Ku et al. ............ 514/11 |
| 2010/0150866 A1 | 6/2010 | Wang et al. |
| 2010/0160403 A1 | 6/2010 | Link et al. |
| 2010/0168384 A1 | 7/2010 | McDaniel et al. |
| 2010/0196321 A1 | 8/2010 | Cooper et al. |
| 2010/0240698 A1 | 9/2010 | Simmen et al. |
| 2010/0260710 A1 | 10/2010 | Parsy et al. |
| 2010/0272674 A1 | 10/2010 | Hiebert et al. |
| 2010/0292219 A1 | 11/2010 | Agarwal et al. |
| 2010/0297079 A1 | 11/2010 | Almond et al. |
| 2011/0020272 A1 | 1/2011 | Schubert |
| 2011/0059047 A1 | 3/2011 | Seiwert et al. |
| 2011/0065737 A1 | 3/2011 | Liu et al. |
| 2011/0178107 A1 | 7/2011 | Wang et al. |
| 2011/0312973 A1* | 12/2011 | Liepold et al. ........... 514/255.05 |

FOREIGN PATENT DOCUMENTS

| | | | |
|---|---|---|---|
| WO | 96/40751 A1 | 12/1996 |
| WO | 96/40752 A1 | 12/1996 |
| WO | 99/07733 A2 | 2/1999 |
| WO | 00/09543 A2 | 2/2000 |
| WO | 00/09558 A1 | 2/2000 |
| WO | 00/59929 A1 | 10/2000 |
| WO | 02/060926 A2 | 8/2002 |
| WO | 03/053349 A2 | 7/2003 |
| WO | 03/064416 A1 | 8/2003 |
| WO | 03/064455 A2 | 8/2003 |
| WO | 03/064456 A1 | 8/2003 |
| WO | 03/066103 A1 | 8/2003 |
| WO | 03/099274 A1 | 12/2003 |
| WO | 2004/030670 A1 | 4/2004 |
| WO | 2004/037855 A1 | 5/2004 |
| WO | 2004/039833 A1 | 5/2004 |
| WO | 2004/072243 A2 | 8/2004 |
| WO | 2004/087741 A1 | 10/2004 |
| WO | 2004/089974 A1 | 10/2004 |
| WO | 2004/092203 A2 | 10/2004 |
| WO | 2004/093798 A2 | 11/2004 |
| WO | 2004/093915 A1 | 11/2004 |
| WO | 2004/094452 A2 | 11/2004 |
| WO | 2004/103996 A1 | 12/2004 |
| WO | 2005/028501 A1 | 3/2005 |
| WO | 2005/037214 A2 | 4/2005 |
| WO | 2005/046712 A1 | 5/2005 |
| WO | 2005/051410 A1 | 6/2005 |
| WO | 2005/051980 A1 | 6/2005 |
| WO | 2005/054430 A2 | 6/2005 |
| WO | 2005/070955 A1 | 8/2005 |
| WO | 2005/075502 A1 | 8/2005 |
| WO | 2005/090383 A2 | 9/2005 |
| WO | 2005/095403 A2 | 10/2005 |
| WO | 2005/116054 A1 | 12/2005 |
| WO | 2006/000085 A1 | 1/2006 |
| WO | 2006/005479 A2 | 1/2006 |
| WO | 2006/020276 A2 | 2/2006 |
| WO | 2006/033851 A1 | 3/2006 |
| WO | 2006/033878 A1 | 3/2006 |
| WO | 2006/036614 A2 | 4/2006 |
| WO | 2006/096652 A2 | 9/2006 |
| WO | 2006/114405 A2 | 11/2006 |
| WO | 2006/119061 A2 | 11/2006 |
| WO | 2006/122188 A2 | 11/2006 |
| WO | 2006/128455 A2 | 12/2006 |
| WO | 2006/130552 A2 | 12/2006 |
| WO | 2006/130553 A2 | 12/2006 |
| WO | 2006/130607 A2 | 12/2006 |
| WO | 2006/130626 A2 | 12/2006 |
| WO | 2006/130627 A2 | 12/2006 |
| WO | 2006/130628 A2 | 12/2006 |
| WO | 2006/130666 A2 | 12/2006 |
| WO | 2006/130686 A2 | 12/2006 |
| WO | 2006/130687 A2 | 12/2006 |
| WO | 2006/130688 A2 | 12/2006 |
| WO | 2007/001406 A2 | 1/2007 |
| WO | 2007/005838 A2 | 1/2007 |
| WO | 2007/008657 A2 | 1/2007 |
| WO | 2007/009109 A2 | 1/2007 |
| WO | 2007/009227 A1 | 1/2007 |
| WO | 2007/014919 A1 | 2/2007 |
| WO | 2007/014921 A1 | 2/2007 |
| WO | 2007/014923 A1 | 2/2007 |
| WO | 2007/014924 A1 | 2/2007 |
| WO | 2007/014925 A1 | 2/2007 |
| WO | 2007/014926 A1 | 2/2007 |
| WO | 2007/015824 A2 | 2/2007 |
| WO | 2007/016441 A1 | 2/2007 |
| WO | 2007/030656 A1 | 3/2007 |
| WO | 2007/044893 A2 | 4/2007 |
| WO | 2007/044933 A1 | 4/2007 |
| WO | 2007/056120 A1 | 5/2007 |
| WO | 2007/131966 A1 | 11/2007 |
| WO | 2007/139585 A1 | 12/2007 |
| WO | 2007/143694 A2 | 12/2007 |
| WO | 2007/148135 A1 | 12/2007 |
| WO | 2008/002924 A2 | 1/2008 |
| WO | 2008/008502 A1 | 1/2008 |
| WO | 2008/008776 A2 | 1/2008 |
| WO | 2008/019289 A2 | 2/2008 |
| WO | 2008/019303 A2 | 2/2008 |
| WO | 2008/021956 A2 | 2/2008 |
| WO | 2008/021960 A2 | 2/2008 |
| WO | 2008/022006 A2 | 2/2008 |
| WO | 2008/039538 A2 | 4/2008 |
| WO | 2008/046860 A2 | 4/2008 |
| WO | 2008/051475 A2 | 5/2008 |
| WO | 2008/051514 A2 | 5/2008 |
| WO | 2008/057208 A2 | 5/2008 |
| WO | 2008/057209 A1 | 5/2008 |
| WO | 2008/057871 A2 | 5/2008 |
| WO | 2008/057873 A2 | 5/2008 |
| WO | 2008/057875 A2 | 5/2008 |
| WO | 2008/057995 A2 | 5/2008 |
| WO | 2008/059046 A1 | 5/2008 |
| WO | 2008/060927 A2 | 5/2008 |
| WO | 2008/062457 A2 | 5/2008 |
| WO | 2008/064057 A1 | 5/2008 |
| WO | 2008/064061 A1 | 5/2008 |
| WO | 2008/064066 A1 | 5/2008 |
| WO | 2008/070733 A2 | 6/2008 |
| WO | 2008/086161 A1 | 7/2008 |
| WO | 2008/092954 A2 | 8/2008 |
| WO | 2008/095058 A1 | 8/2008 |
| WO | 2008/096001 A1 | 8/2008 |
| WO | 2008/098368 A1 | 8/2008 |
| WO | 2008/101665 A1 | 8/2008 |
| WO | 2008/106130 A2 | 9/2008 |
| WO | 2008/114006 A1 | 9/2008 |
| WO | 2008/124384 A2 | 10/2008 |
| WO | 2008/128921 A1 | 10/2008 |

(56) References Cited

FOREIGN PATENT DOCUMENTS

| | | | |
|---|---|---|---|
| WO | 2008/137779 | A2 | 11/2008 |
| WO | 2008/141227 | A1 | 11/2008 |
| WO | 2009/005676 | A2 | 1/2009 |
| WO | 2009/005677 | A2 | 1/2009 |
| WO | 2009/010804 | A1 | 1/2009 |
| WO | 2009/014730 | A1 | 1/2009 |
| WO | 2009/053828 | A2 | 4/2009 |
| WO | 2009/067108 | A1 | 5/2009 |
| WO | 2009/070689 | A1 | 6/2009 |
| WO | 2009/070692 | A1 | 6/2009 |
| WO | 2009/073713 | A1 | 6/2009 |
| WO | 2009/073719 | A1 | 6/2009 |
| WO | 2009/073780 | A1 | 6/2009 |
| WO | 2009/080542 | A1 | 7/2009 |
| WO | 2009/082697 | A1 | 7/2009 |
| WO | 2009/082701 | A1 | 7/2009 |
| WO | 2009/085659 | A1 | 7/2009 |
| WO | 2009/099596 | A2 | 8/2009 |
| WO | 2009/129109 | A1 | 10/2009 |
| WO | 2009/137432 | A1 | 11/2009 |
| WO | 2009/139792 | A1 | 11/2009 |
| WO | 2009/140475 | A1 | 11/2009 |
| WO | 2009/140500 | A1 | 11/2009 |
| WO | 2009/142842 | A2 | 11/2009 |
| WO | 2009/146347 | A1 | 12/2009 |
| WO | 2009/148923 | A1 | 12/2009 |
| WO | 2009/149377 | A1 | 12/2009 |
| WO | 2010/000459 | A1 | 1/2010 |
| WO | 2010/015545 | A1 | 2/2010 |
| WO | 2010/021717 | A2 | 2/2010 |
| WO | 2010/028236 | A1 | 3/2010 |
| WO | 2010/033443 | A1 | 3/2010 |
| WO | 2010/033444 | A1 | 3/2010 |
| WO | 2010/033466 | A1 | 3/2010 |
| WO | 2010/034105 | A1 | 4/2010 |
| WO | 2010/036551 | A1 | 4/2010 |
| WO | 2010/036871 | A1 | 4/2010 |
| WO | 2010/036896 | A1 | 4/2010 |
| WO | 2010/042834 | A1 | 4/2010 |
| WO | 2010/048468 | A1 | 4/2010 |
| WO | 2010/059667 | A1 | 5/2010 |
| WO | 2010/059937 | A1 | 5/2010 |
| WO | 2010/065577 | A1 | 6/2010 |
| WO | 2010/077783 | A1 | 7/2010 |
| WO | 2010/080389 | A1 | 7/2010 |
| WO | 2010/088394 | A1 | 8/2010 |
| WO | 2010/118078 | A1 | 10/2010 |
| WO | 2010/120476 | A2 | 10/2010 |
| WO | 2010/128521 | A2 | 11/2010 |
| WO | 2010/135520 | A1 | 11/2010 |
| WO | 2010/135748 | A1 | 11/2010 |
| WO | 2011/017389 | A1 | 2/2011 |
| WO | 2011/063501 | A1 | 6/2011 |
| WO | 2011/063502 | A1 | 6/2011 |

OTHER PUBLICATIONS

J. Rancourt et al., "Peptide-Based Inhibitors of the Hepatitis C Virus NS3 Protease: Structure-Activity Relationship at the C-Terminal Position", J. Med. Chem., vol. 47, pp. 2511-2522 (2004).

B.W. Dymock et al., "Emerging therapies for hepatitis C virus infection", Emerging Drugs—Ashley Publications Ltd., 6 (1), pp. 13-42 (2001).

M. Llinás-Brunet et al., "Peptide-Based Inhibitors of the Hepatitis C Virus Serine Protease", Bioorganic & Medicinal Chemistry Letters 8, pp. 1713-1718 (1998).

Y.S. Tsantrizos et al., "Macrocyclic Inhibitors of the NS3 Protease as Potential Therapeutic Agents of Hepatitis C Virus Infection", Angew. Chem. Int. Ed., 42(12), pp. 1355-1360 (2003).

J.L. Kim et al., "Crystal Structure of the Hepatitis C Virus NS3 Protease Domain Complexed with a Synthetic NS4A Cofactor Peptide", Cell, vol. 87, pp. 343-355 (1996).

G. Barbato et al., "Inhibitor binding induces active site stabilization of the HCV NS3 protein serine protease domain", The EMBO Journal, 19(6), pp. 1195-1206 (2000).

P. Ettmayer et al., J. Med. Chem., 47(10), pp. 2393-2404 (2004).

Y. Singh et al., "Recent Trends in targeted Anticancer Prodrug and Conjugate", DesignCurr Med. Chem., 15(18), pp. 1802-1826 (2008).

C.E. Muller et al., "Prodrug Approaches for Enhancing the Bioavailability of Drugs with Low Solubility", Chemistry & Biodiversity, vol. 6, pp. 2071-2083(2009).

Beaumont et al., "Design of Ester Prodrugs to Enhance Oral Absorption of Poorly Permeable Compounds: Challenges to the Discovery Scientist", Current Drug Metabolism, vol. 4, pp. 461-485 (2003).

H.K. Han et al., AAPS Pharmsci.—Article 6, 2(1), pp. 1-11 (2000).

Testa et al., "Prodrug Research: Futile or Fertile?", Biochemical Pharmacology, pp. 2097-2106 (2004).

R. Ronn et al., "Exploration of acyl sulfonamides as carboxylic acid replacements in protease inhibitors of the hepatitis C virus full-length NS3", Bioorganic & Medicinal Chemistry, vol. 14, pp. 544-559 (2006).

* cited by examiner

PHENANTHRIDINE MACROCYCLIC HEPATITIS C SERINE PROTEASE INHIBITORS

RELATED APPLICATIONS

This application claims the benefit of U.S. Provisional application 61/428,488, filed Dec. 30, 2010, and U.S. Provisional application 61/449,331, filed Mar. 4, 2011. The entire contents of the above applications are incorporated herein by reference.

JOINT RESEARCH AGREEMENT

Inventions described in this application were made by or on behalf of Abbott Laboratories and Enanta Pharmaceuticals, Inc. whom are parties to a joint research agreement, that was in effect on or before the date such inventions were made and such inventions were made as a result of activities undertaken within the scope of the joint research agreement.

TECHNICAL FIELD

The present invention relates to novel macrocycles having activity against the hepatitis C virus (HCV) and useful in the treatment of HCV infections. More particularly, the invention relates to macrocyclic compounds, compositions containing such compounds and methods for using the same, as well as processes for making such compounds.

BACKGROUND OF THE INVENTION

HCV is the principal cause of non-A, non-B hepatitis and is an increasingly severe public health problem both in the developed and developing world. It is estimated that the virus infects over 200 million people worldwide, surpassing the number of individuals infected with the human immunodeficiency virus (HIV) by nearly five fold. HCV infected patients, due to the high percentage of individuals inflicted with chronic infections, are at an elevated risk of developing cirrhosis of the liver, subsequent hepatocellular carcinoma and terminal liver disease. HCV is the most prevalent cause of hepatocellular cancer and cause of patients requiring liver transplantations in the western world.

There are considerable barriers to the development of anti-HCV therapeutics, which include, but are not limited to, the persistence of the virus, the genetic diversity of the virus during replication in the host, the high incident rate of the virus developing drug-resistant mutants, and the lack of reproducible infectious culture systems and small-animal models for HCV replication and pathogenesis. In a majority of cases, given the mild course of the infection and the complex biology of the liver, careful consideration must be given to antiviral drugs, which are likely to have significant side effects.

SUMMARY OF THE INVENTION

The present invention relates to novel macrocyclic compounds and methods of treating a hepatitis C infection in a subject in need of such therapy with said macrocyclic compounds. The compounds of the present invention interfere with the life cycle of the hepatitis C virus and are useful as antiviral agents. The present invention further relates to pharmaceutical compositions comprising the compounds of the present invention, or pharmaceutically acceptable salts, esters or prodrugs thereof, in combination with a pharmaceutically acceptable carrier or excipient.

In one aspect, the invention provides a compound, of formula I:

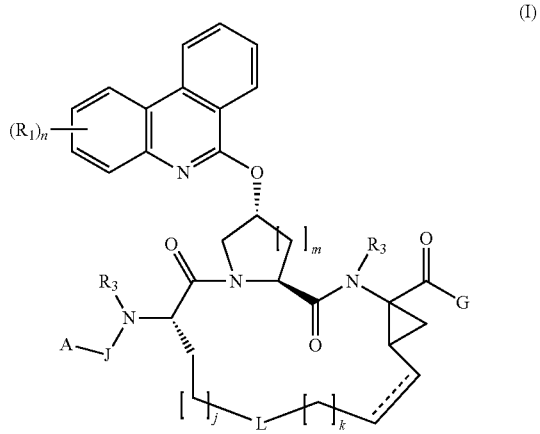

(I)

or a pharmaceutically acceptable salt, ester or prodrug thereof,
wherein:
J is absent, optionally substituted alkylene, optionally substituted alkenylene, optionally substituted alkynylene, —C(O)—, —O—C(O)—, —N(R$_3$)—C(O)—, —C(S)—, —C(=NR$_4$)—, —S(O)—, —S(O$_2$)—, or —N(R$_3$)—;
A is optionally substituted alkyl, optionally substituted alkenyl, or optionally substituted alkynyl, each containing 0, 1, 2, or 3 heteroatoms selected from O, S, or N; optionally substituted aryl, optionally substituted arylalkyl, optionally substituted alkoxy, optionally substituted heteroaryl, optionally substituted heterocyclic, or optionally substituted carbocyclic;
each R$_1$ is independently selected from
  (i) halogen, hydroxy, amino, —CN, —CF$_3$, —N$_3$, —NO$_2$, —SR$_4$, —SOR$_4$, —SO$_2$R$_4$, —N(R$_3$)S(O)$_2$—R$_4$, —N(R$_3$)(SO$_2$)NR$_3$R$_4$, —NR$_3$R$_4$, —C(O)—O_R$_4$, —C(O)R$_4$, —C(O)NR$_3$R$_4$, or —N(R$_3$)C(O)R$_4$;
  (ii) optionally substituted aryl;
  (iii) optionally substituted heteroaryl;
  (iv) optionally substituted heterocyclic;
  (v) optionally substituted carbocyclic; or
  (vi) optionally substituted alkyl, optionally substituted alkenyl, or optionally substituted alkynyl, each containing 0, 1, 2, or 3 heteroatoms selected from O, S, or N;
wherein at least one of R$_1$ is halogen or —OR$_4$;
G is -E-R$_5$;
  wherein E is absent; optionally substituted alkylene, optionally substituted alkenylene, optionally substituted alkynylene, each containing 0, 1, 2, or 3 heteroatoms selected from O, S, or N; or —O—, —S—, —N(R$_3$)—, —N(R$_3$)S(O$_p$)—, —N(R$_3$)C(O)—, —N(R$_3$)C(O)S(O$_p$)—, —OS(O$_p$)—, —C(O)S (O$_p$)—, or —C(O)N(R$_3$)S(O$_p$)—;
  each p is independently 0, 1, or 2;
  R$_5$ is H; optionally substituted alkyl, optionally substituted alkenyl, or optionally substituted alkynyl, each containing 0, 1, 2, or 3 heteroatoms selected from O, S, or N; optionally substituted carbocyclic, optionally substituted heterocyclic, optionally substituted aryl, or optionally substituted heteroaryl;

$R_3$ and $R_4$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

L is absent or is selected from optionally substituted alkylene, optionally substituted alkenylene or optionally substituted alkynylene, each containing 0, 1, 2, or 3 heteroatoms selected from O, S, or N;

j=0, 1, 2, 3, or 4;
k=0, 1, 2, or 3;
m=0, 1, or 2;
n is 1, 2, 3, or 4; and
----- denotes a carbon-carbon single bond

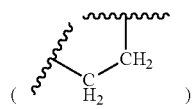

or double bond

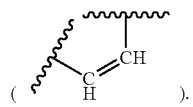 [SMILES: */C=C\*]

DETAILED DESCRIPTION OF THE INVENTION

Various compounds of the invention demonstrate substantially improved antiviral activity against HCV genotype 3a infections compared to unsubstituted phenanthridine compounds. Various compounds of the invention also demonstrate substantially improved antiviral activity against clinically relevant resistant mutants, especially genotype 1a R155K and D169V. Such compounds also exhibit improved pharmacokinetic properties, as measured preclinically in animals such as rat or dog.

It is understood that the embodiments of the invention discussed below with respect to the preferred variable selections can be taken alone or in combination with one or more of the other embodiments, or preferred variable selections, of the invention, as if each combination were explicitly listed herein.

In one aspect, the invention provides a compound of formula I:

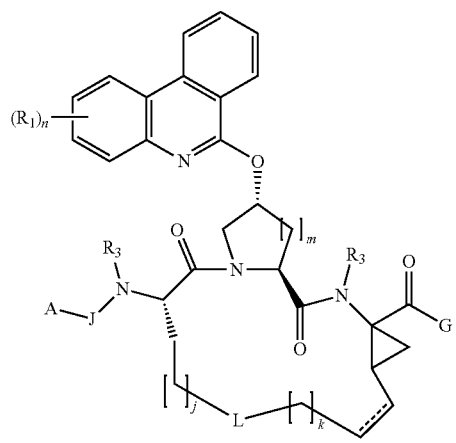

(I)

or a pharmaceutically acceptable salt, ester or prodrug thereof, wherein:

J is absent, optionally substituted alkylene, optionally substituted alkenylene, optionally substituted alkynylene, —C(O)—, —O—C(O)—, —N($R_3$)—C(O)—, —C(S)—, —C(=N$R_4$)—, —S(O)—, —S($O_2$)—, or —N($R_3$)—;

A is optionally substituted alkyl, optionally substituted alkenyl, or optionally substituted alkynyl, each containing 0, 1, 2, or 3 heteroatoms selected from O, S, or N; optionally substituted aryl, optionally substituted arylalkyl, optionally substituted alkoxy, optionally substituted heteroaryl, optionally substituted heterocyclic, or optionally substituted carbocyclic;

each $R_1$ is independently selected from
(i) halogen, hydroxy, amino, —CN, —$CF_3$, —$N_3$, —$NO_2$, —$OR_4$, —$SR_4$, —$SOR_4$, —$SO_2R_4$, —N($R_3$)S(O)$_2$—$R_4$, —N($R_3$)($SO_2$)N$R_3R_4$, —N$R_3R_4$, —C(O)—O_$R_4$, —C(O)$R_4$, —C(O)N$R_3R_4$, or —N($R_3$)C(O)$R_4$;
(ii) optionally substituted aryl;
(iii) optionally substituted heteroaryl;
(iv) optionally substituted heterocyclic;
(v) optionally substituted carbocyclic; or
(vi) optionally substituted alkyl, optionally substituted alkenyl, or optionally substituted alkynyl, each containing 0, 1, 2, or 3 heteroatoms selected from O, S, or N;
wherein at least one of $R_1$ is halogen or —$OR_4$;

G is -E-$R_5$;
wherein E is absent; optionally substituted alkylene, optionally substituted alkenylene, optionally substituted alkynylene, each containing 0, 1, 2, or 3 heteroatoms selected from O, S, or N; or —O—, —S—, —N($R_3$)—, —N($R_3$)S($O_p$)—, —N($R_3$)C(O)—, —N($R_3$)C(O)S($O_p$)—, —OS($O_p$)—, —C(O)S($O_p$)—, or —C(O)N($R_3$)S($O_p$)—;
each p is independently 0, 1, or 2;
$R_5$ is H; optionally substituted alkyl, optionally substituted alkenyl, or optionally substituted alkynyl, each containing 0, 1, 2, or 3 heteroatoms selected from O, S, or N; optionally substituted carbocyclic, optionally substituted heterocyclic, optionally substituted aryl, or optionally substituted heteroaryl;

$R_3$ and $R_4$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

L is absent or is selected from optionally substituted alkylene, optionally substituted alkenylene or optionally substituted alkynylene, each containing 0, 1, 2, or 3 heteroatoms selected from O, S, or N;

j=0, 1, 2, 3, or 4;
k=0, 1, 2, or 3;
m=0, 1, or 2;
n is 1, 2, 3, or 4; and
----- denotes a carbon-carbon single bond

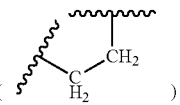

or double bond

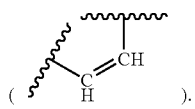

In another aspect, the invention provides a compound of formula I':

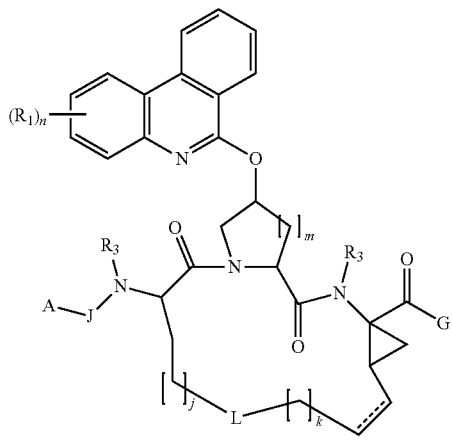

or a pharmaceutically acceptable salt, ester or prodrug thereof, wherein J, A, $R_1$, G, $R_5$, L, j, k, m, and n are as defined above.

In other embodiments, E is —NHS(O)— or —NHS$(O_2)$—, and $R_5$ is cyclopropyl, cyclobutyl, cyclopentyl, cyclohexyl, cycloheptyl, pyridinyl, pyrimidinyl, furanyl, thienyl, pyrrolyl, pyrazolyl, pyrrolidinyl, morpholinyl, piperidinyl, piperazinyl, or imidazolyl, each of which is optionally substituted.

In various embodiments, J is —C(O)— and A is optionally substituted —$C_1$-$C_8$alkyl, containing 0, 1, 2, or 3 heteroatoms selected from O, S, or N; optionally substituted aryl, optionally substituted —$C_1$-$C_8$ alkoxy, optionally substituted heteroaryl, optionally substituted —$C_3$-$C_{12}$ cycloalkyl, or optionally substituted —$C_3$-$C_{12}$ heterocycloalkyl.

In certain embodiments, k=3, j=1 and L is absent.

In various embodiments, each $R_1$ is independently selected from halogen, hydroxy, amino, —CN, —$CF_3$, —$N_3$, —$NO_2$, —$OR_4$, —$SR_4$, —$SOR_4$, —$SO_2R_4$, —$N(R_3)S(O_2)$—$R_4$, —$N(R_3)S(O_2)NR_3R_4$, —$NR_3R_4$, —$C(O)OR_4$, —$C(O)R_4$, —$C(O)NR_3R_4$, or —$N(R_3)C(O)R_4$; optionally substituted aryl; optionally substituted heteroaryl; optionally substituted heterocyclic; optionally substituted carbocyclic; or optionally substituted alkyl, optionally substituted alkenyl, or optionally substituted alkynyl, each containing 0, 1, 2, or 3 heteroatoms selected from O, S, or N; wherein at least one $R_1$ is halogen or —$OR_4$.

In a further embodiment, each $R_1$ is independently halogen, hydroxy, amino, —CN, —$CF_3$, —$N_3$, —$NO_2$, —$OR_4$, —$SR_4$, —$SOR_4$, —$SO_2R_4$, —$N(R_3)S(O_2)$—$R_4$, —$N(R_3)S(O_2)NR_3R_4$, —$NR_3R_4$, —$C(O)OR_4$, —$C(O)R_4$, —$C(O)NR_3R_4$, or —$N(R_3)C(O)R_4$.

Alternatively or additionally, $R_1$ is halogen or —$OR_4$ and n is 1, 2 or 3.

In another aspect, the invention provides a compound of formula II,

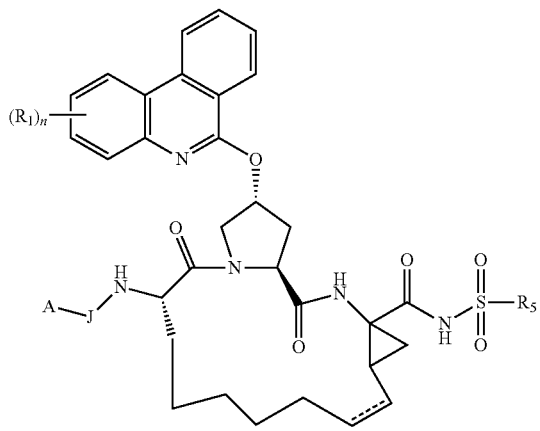

or a pharmaceutically acceptable salt, ester or prodrug thereof, wherein:

J is absent, —C(O)—, —$N(R_3)$—C(O)—, —C(S)—, or —C(=$NR_4$)—;

A is optionally substituted alkyl, optionally substituted alkenyl, or optionally substituted alkynyl, each containing 0, 1, 2, or 3 heteroatoms selected from O, S, or N; optionally substituted aryl, optionally substituted arylalkyl, optionally substituted alkoxy, optionally substituted heteroaryl, optionally substituted heterocyclic, or optionally substituted carbocyclic;

each $R_1$ is independently selected from (i) halogen, hydroxy, amino, —$OR_4$, —$N(R_3)S(O)_2$—$R_4$, —$N(R_3)(SO_2)NR_3R_4$, —$NR_3R_4$, —C(O)—O—$R_4$, —$C(O)R_4$, —$C(O)NR_3R_4$, or —$N(R_3)C(O)R_4$;

(ii) optionally substituted aryl;

(iii) optionally substituted heteroaryl;

(iv) optionally substituted heterocyclic;

(v) optionally substituted carbocyclic; or (vi) optionally substituted alkyl, optionally substituted alkenyl, or optionally substituted alkynyl, each containing 0, 1, 2, or 3 heteroatoms selected from O, S, or N;

wherein at least one of $R_1$ is halogen or —$OR_4$;

$R_5$ is H; optionally substituted alkyl, optionally substituted alkenyl, or optionally substituted alkynyl, each containing 0, 1, 2, or 3 heteroatoms selected from O, S, or N; optionally substituted carbocyclic, optionally substituted heterocyclic, optionally substituted aryl, or optionally substituted heteroaryl;

$R_3$ and $R_4$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted haloalkyl, optionally substituted aryl; optionally substituted heteroaryl; optionally substituted heterocyclic; optionally substituted carbocyclic; or hydrogen;

n is 1, 2, 3, or 4; and

==== denotes a carbon-carbon single bond

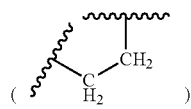

or double bond

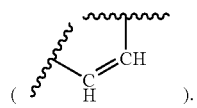

In certain embodiments, $R_5$ is cyclopropyl, cyclobutyl, cyclopentyl, cyclohexyl, cycloheptyl, pyridinyl, pyrimidinyl, furanyl, thienyl, pyrrolyl, pyrazolyl, pyrrolidinyl, morpholinyl, piperidinyl, piperazinyl, or imidazolyl, each of which is optionally substituted.

In another embodiment, J is —C(O)— and A is optionally substituted —$C_1$-$C_8$ alkyl, containing 0, 1, 2, or 3 heteroatoms selected from O, S, or N; optionally substituted aryl, optionally substituted —$C_1$-$C_8$ alkoxy, optionally substituted heteroaryl, optionally substituted —$C_3$-$C_{12}$cycloalkyl, or optionally substituted —$C_3$-$C_{12}$ heterocycloalkyl.

In another embodiment of any aspect of the invention, the invention provides a compound as described above, wherein

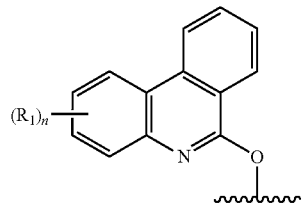

is

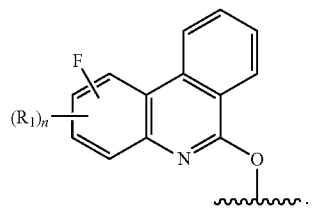

In another embodiment of any aspect of the invention, the invention provides a compound as described above, wherein

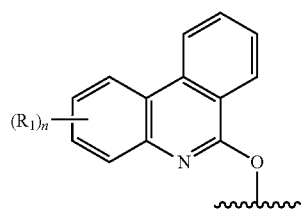

is selected from the following Table 1:

TABLE 1

[Structures of fluorinated phenanthridine derivatives]

TABLE 1-continued

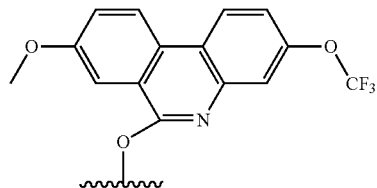 [SMILES: *Oc1nc2cc(OC(F)(F)F)ccc2c2ccc(OC)cc12]

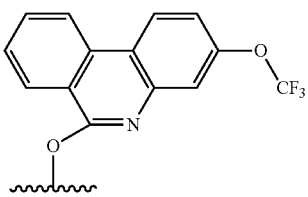 [SMILES: *Oc1nc2cc(OC(F)(F)F)ccc2c2ccccc12]

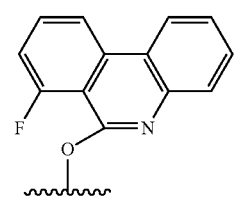 [SMILES: *Oc1nc2ccccc2c2cccc(F)c12]

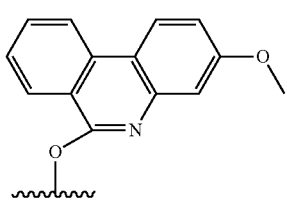 [SMILES: *Oc1nc2cc(OC)ccc2c2ccccc12]

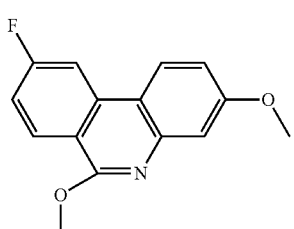

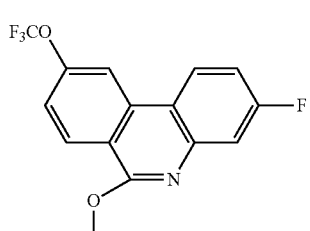

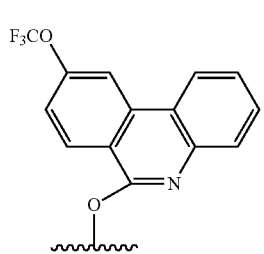 [SMILES: *Oc1nc2ccccc2c2cc(OC(F)(F)F)ccc12]

TABLE 1-continued

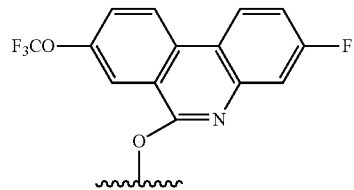 [SMILES: *Oc1nc2cc(F)ccc2c2ccc(OC(F)(F)F)cc12]

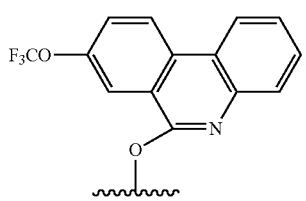 [SMILES: *Oc1nc2ccccc2c2ccc(OC(F)(F)F)cc12]

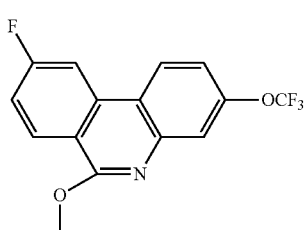

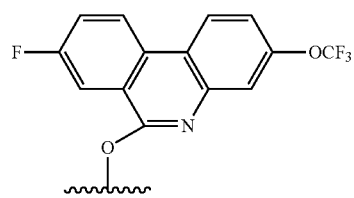 [SMILES: *Oc1nc2cc(OC(F)(F)F)ccc2c2ccc(F)cc12]

Alternatively or additionally, E is —NH—, —NHS(O)$_p$—, or —NH(CO)S(O)$_p$—, and p is 2.

Alternatively or additionally, E is —NHS(O)$_p$—, and p is 2.

Alternatively or additionally, $R_5$ is cyclopropyl, cyclobutyl, cyclopentyl, cyclohexyl, cycloheptyl, pyridinyl, pyrimidinyl, furanyl, thienyl, pyrrolyl, pyrazolyl, pyrrolidinyl, morpholinyl, piperidinyl, piperazinyl, or imidazolyl, each of which is optionally substituted. In a further embodiment, $R_5$ is optionally substituted cyclopropyl.

Alternatively or additionally, J is —C(O)— or —C(=NR$_4$)—. Preferably, J is —C(O)—.

Alternatively or additionally, m is 1.

Alternatively or additionally, A is optionally substituted —C$_1$-C$_8$ alkyl, containing 0, 1, 2, or 3 heteroatoms selected from O, S, or N; optionally substituted —C$_1$-C$_8$haloalkyl, optionally substituted —C$_1$-C$_8$ hydroxyalkyl, optionally substituted aryl, optionally substituted —C$_1$-C$_8$ alkoxy, optionally substituted heteroaryl, optionally substituted —C$_3$-C$_{12}$ cycloalkyl, or optionally substituted —C$_3$-C$_{12}$ heterocyclyl.

In certain embodiments of any aspect of the invention, A is selected from Me, Et, Pr, i-Pr, Bu, s-Bu, t-Bu,

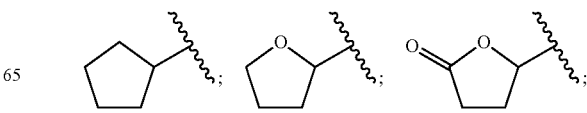

-continued

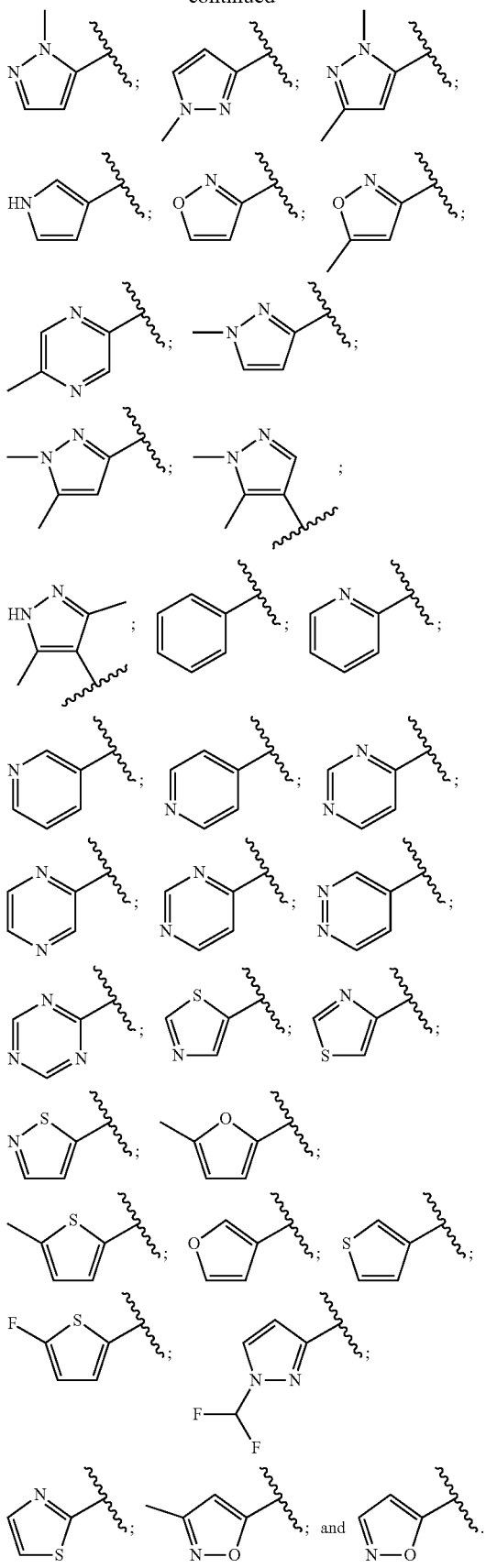

In another embodiment of any aspect of the invention, A is

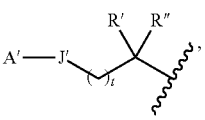

wherein:

J' is —NHC(O)—, —NHC(O)O—, —C(O)—, —C(S)—, —S(O)—, —S(O$_2$)—;

A' is optionally substituted —C$_1$-C$_8$ alkyl, containing 0, 1, 2, or 3 heteroatoms selected from O, S, or N; optionally substituted —C$_1$-C$_8$ haloalkyl, optionally substituted aryl, optionally substituted —C$_1$-C$_8$ alkoxy, optionally substituted heteroaryl, optionally substituted —C$_3$-C$_{12}$ cycloalkyl, or optionally substituted —C$_3$-C$_{12}$ heterocyclyl;

R' is H, optionally substituted —C$_1$-C$_8$ alkyl, optionally substituted —C$_3$-C$_{12}$ cycloalkyl, optionally substituted aryl, optionally substituted heteroaryl, or optionally substituted —C$_3$-C$_{12}$ heterocyclyl;

R" is H, optionally substituted —C$_1$-C$_8$ alkyl, optionally substituted —C$_3$-C$_{12}$ cycloalkyl, optionally substituted aryl, optionally substituted heteroaryl, or optionally substituted —C$_3$-C$_{12}$ heterocyclyl; and t is 0 or 1.

In further embodiments,

J' is —NHC(O)—, or —NHC(O)O—;

A' is optionally substituted —C$_1$-C$_8$ alkyl, containing 0, 1, 2, or 3 heteroatoms selected from O, S, or N; optionally substituted aryl, or optionally substituted heteroaryl;

R' is H, optionally substituted —C$_1$-C$_8$ alkyl or optionally substituted —C$_3$-C$_{12}$ cycloalkyl, R" is H, and t is 0 or 1.

In a further embodiment, A' is Me, Et, Pr, i-Pr, Bu, s-Bu, t-Bu, cyclopropyl, cyclobutyl, cyclopentyl, cyclohexyl, cycloheptyl, pyridinyl, pyrimidinyl, furanyl, thienyl, pyrrolyl, pyrazolyl, pyrrolidinyl, morpholinyl, piperidinyl, piperazinyl, imidazolyl,

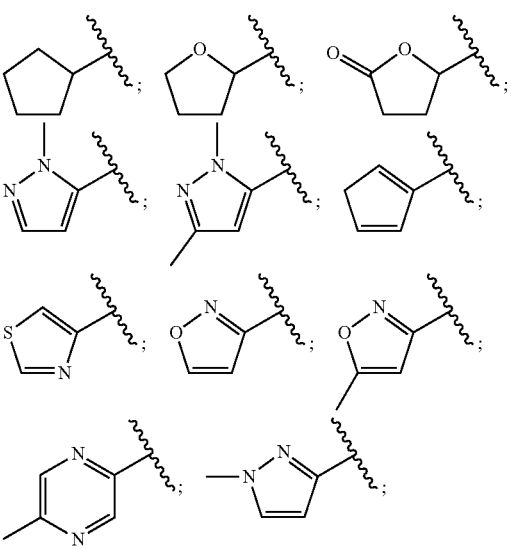

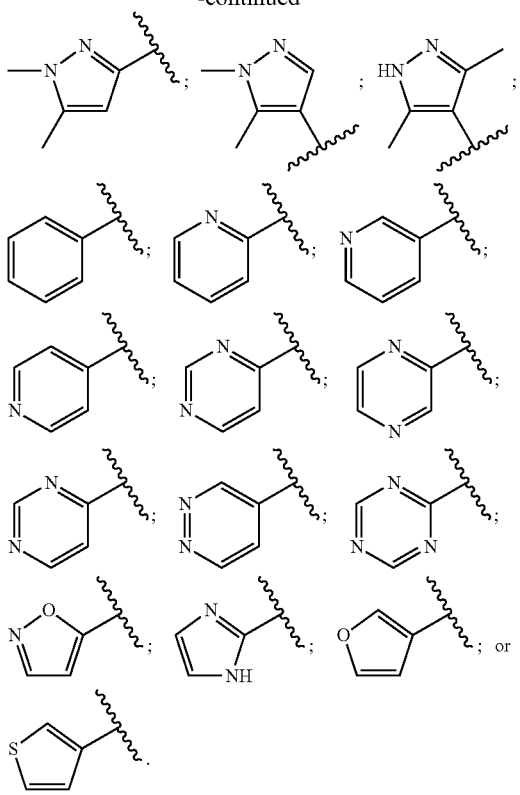

each of which is optionally substituted.

In a further embodiment, R' is Et, Pr, i-Pr, t-Bu, cyclopropyl, cyclobutyl, cyclopentyl, cyclohexyl, tetrahydropyran, CH$_2$-i-Pr, CH$_2$-t-Bu, CH$_2$-cyclopropyl, CH$_2$-cyclobutyl, CH$_2$-cyclopentyl, CH$_2$-cyclohexyl, or CH$_2$-tetrahydropyran.

In another embodiment of any aspect of the invention, A is

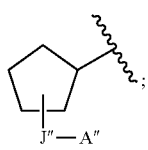

wherein J" is —NC(O)—, —NC(O)O—, —C(O)—, —O—C(O)—, —C(S)—, —C(=NR$_4$)—, —S(O)—, —S(O$_2$)—; and A" is optionally substituted —C$_1$-C$_8$ alkyl, containing 0, 1, 2, or 3 heteroatoms selected from O, S, or N; optionally substituted —C$_1$-C$_8$ haloalkyl, optionally substituted aryl, optionally substituted —C$_1$-C$_8$ alkoxy, optionally substituted heteroaryl, optionally substituted —C$_3$-C$_{12}$ cycloalkyl, or optionally substituted —C$_3$-C$_{12}$ heterocyclyl.

In a further embodiment, J" is —NC(O)— or —NC(O)O—; and A" is optionally substituted —C$_1$-C$_8$ alkyl, containing 0, 1, 2, or 3 heteroatoms selected from O, S, or N, or optionally substituted heteroaryl.

In a further embodiment, A" is t-Bu, optionally substituted pyrazine, or optionally substituted isoxazole.

In another embodiment of any aspect of the invention, A is —CHR$_Z$(OH)—, wherein R$_Z$ is cyclohexyl, i-Pr, i-Bu, t-Bu, or CF$_3$.

In another embodiment of any aspect of the invention, A is CHF$_2$—R$_Y$, wherein R$_Y$ is Ph or Et.

In certain embodiments of any aspect of the invention, E is —N(R$_3$)S(O)$_p$—; —N(R$_3$)C(O)—, —OS(O)$_p$—, or —C(O)S(O)$_p$—; and p is 2.

In a further embodiment of any aspect of the invention, R$_5$ is optionally substituted carbocyclic, optionally substituted heterocyclic, optionally substituted aryl, or optionally substituted heteroaryl. In certain embodiments, R$_5$ is carbocyclic. In a further embodiment, R$_5$ is cyclopropyl, which is optionally substituted.

In another embodiments of any aspect of the invention, J is —C(O)—.

In other embodiments of any aspect of the invention, A is an optionally substituted alkyl, an optionally substituted haloalkyl, optionally substituted cycloalkyl, optionally substituted heterocyclyl, or optionally substituted heteroaryl.

In certain embodiments of any aspect of the invention, A is methyl, ethyl, propyl, iso-propyl, butyl, i-butyl, t-butyl, pentyl, hexyl, heptyl,

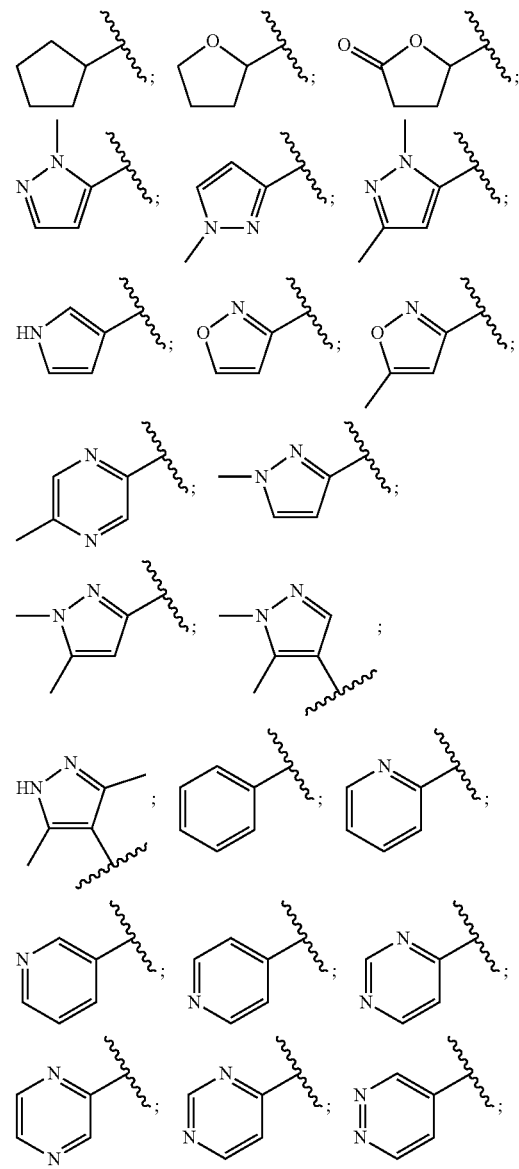

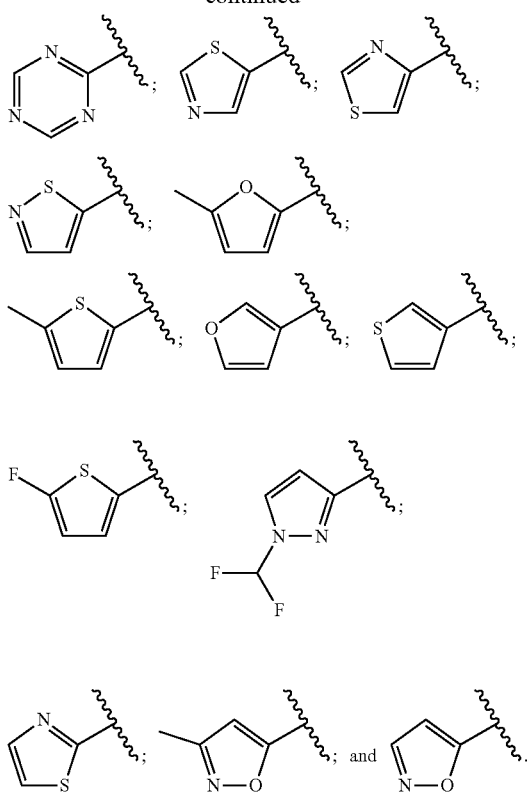

In certain embodiments of any aspect of the invention, each $R_1$ is independently selected from H, halogen, hydroxy, amino, —CN, —CF$_3$, —N$_3$, —NO$_2$, —OR$_4$, —SR$_4$, —NR$_3$R$_4$, optionally substituted aryl; optionally substituted heteroaryl; optionally substituted heterocyclic; optionally substituted carbocyclic; optionally substituted haloalkyl, or optionally substituted alkyl, optionally substituted alkenyl, optionally substituted alkynyl; wherein at least one $R_1$ is halogen or —OR$_4$—.

In various embodiments of any aspect of the invention, each $R_3$ and $R_4$ is independently selected at each occurrence from the following: optionally substituted alkyl, optionally substituted haloalkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen.

In certain embodiments of any aspect of the invention, G is E-R$_5$, wherein E is —NHS(O)$_2$— and R$_5$ is cyclopropyl, which is optionally substituted.

In another embodiment of each of the above-described aspects of the invention, A is optionally substituted cycloalkyl.

In another embodiment of each of the above-described aspects of the invention, A is optionally substituted heterocyclyl.

In another embodiment of each of the above-described aspects of the invention, A is optionally substituted alkyl.

In another embodiment of each of the above-described aspects of the invention A is optionally substituted heteroaryl.

In another embodiment of each of the above-described aspects of the invention A is

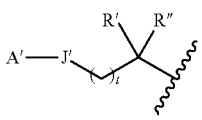

In another embodiment of each of the above-described aspects of the invention A is

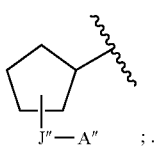

In another embodiment of each of the above-described aspects of the invention A is —CHR$_Z$(OH)—.

In another embodiment of each of the above-described aspects of the invention A is CHF$_2$—R$_Y$.

In another embodiment of each of the above-described aspects of the invention, J is —C(O)—; and A is optionally substituted cycloalkyl.

In another embodiment of each of the above-described aspects of the invention, J is —C(O)—; and A is optionally substituted heterocyclyl.

In another embodiment of each of the above-described aspects of the invention, J is —C(O)—; and A is optionally substituted alkyl.

In another embodiment of each of the above-described aspects of the invention J is —C(O)—; and A is optionally substituted heteroaryl.

In another embodiment of each of the above-described aspects of the invention J is —C(O)—; and A is

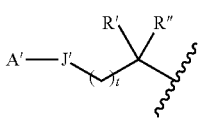

In another embodiment of each of the above-described aspects of the invention J is —C(O)—; and A is

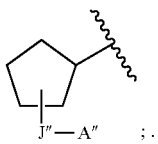

In another embodiment of each of the above-described aspects of the invention J is —C(O)—; and A is —CHR$_Z$(OH)—.

In another embodiment of each of the above-described aspects of the invention J is —C(O)—; and A is CHF$_2$—R$_Y$.

In another embodiment of each of the above-described aspects of the invention, E is —NHS(O)$_2$; R$_5$ is cyclopropyl or methyl-substituted cyclopropyl; and A is optionally substituted cycloalkyl.

In another embodiment of each of the above-described aspects of the invention, E is —NHS(O)$_2$; R$_5$ is cyclopropyl or methyl-substituted cyclopropyl; and A is optionally substituted heterocyclyl.

In another embodiment of each of the above-described aspects of the invention, E is —NHS(O)$_2$; R$_5$ is cyclopropyl or methyl-substituted cyclopropyl; and A is optionally substituted alkyl.

In another embodiment of each of the above-described aspects of the invention E is —NHS(O)$_2$; R$_5$ is cyclopropyl or methyl-substituted cyclopropyl; and A is optionally substituted heteroaryl.

In another embodiment of each of the above-described aspects of the invention E is —NHS(O)$_2$; R$_5$ is cyclopropyl or methyl-substituted cyclopropyl; and A is

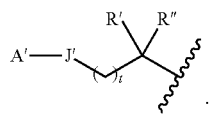

In another embodiment of each of the above-described aspects of the invention E is —NHS(O)$_2$; R$_5$ is cyclopropyl or methyl-substituted cyclopropyl; and A is

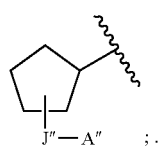

In another embodiment of each of the above-described aspects of the invention E is —NHS(O)$_2$; R$_5$ is cyclopropyl or methyl-substituted cyclopropyl; and A is —CHR$_Z$(OH)—.

In another embodiment of each of the above-described aspects of the invention E is —NHS(O)$_2$; R$_5$ is cyclopropyl or methyl-substituted cyclopropyl; and A is CHF$_2$—R$_Y$.

In another embodiment of each of the above-described aspects of the invention, E is —NHS(O)$_2$; R$_5$ is cyclopropyl or methyl-substituted cyclopropyl; J is —C(O)—; and A is optionally substituted cycloalkyl.

In another embodiment of each of the above-described aspects of the invention, E is —NHS(O)$_2$; R$_5$ is cyclopropyl or methyl-substituted cyclopropyl; J is —C(O)—; and A is optionally substituted heterocyclyl.

In another embodiment of each of the above-described aspects of the invention, E is —NHS(O)$_2$; R$_5$ is cyclopropyl or methyl-substituted cyclopropyl; J is —C(O)—; and A is optionally substituted alkyl.

In another embodiment of each of the above-described aspects of the invention E is —NHS(O)$_2$; R$_5$ is cyclopropyl or methyl-substituted cyclopropyl; J is —C(O)—; and A is optionally substituted heteroaryl.

In another embodiment of each of the above-described aspects of the invention E is —NHS(O)$_2$; R$_5$ is cyclopropyl or methyl-substituted cyclopropyl; J is —C(O)—; and A is

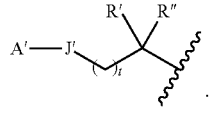

In another embodiment of each of the above-described aspects of the invention E is —NHS(O)$_2$; R$_5$ is cyclopropyl or methyl-substituted cyclopropyl; J is —C(O)—; and A is

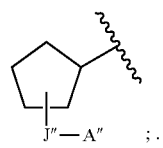

In another embodiment of each of the above-described aspects of the invention E is —NHS(O)$_2$; R$_5$ is cyclopropyl or methyl-substituted cyclopropyl; J is —C(O)—; and A is —CHR$_Z$(OH)—.

In another embodiment of each of the above-described aspects of the invention E is —NHS(O)$_2$; R$_5$ is cyclopropyl or methyl-substituted cyclopropyl; J is —C(O)—; and A is CHF$_2$—R$_Y$.

In another embodiment of each of the above-described aspects and embodiments of the invention,

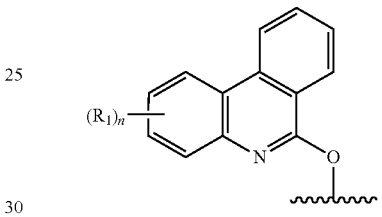

is selected from the following Table 1:

TABLE 1

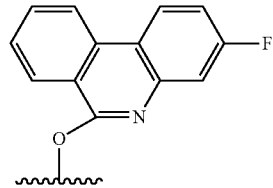 [SMILES: *Oc1nc2cc(F)ccc2c2ccccc12]

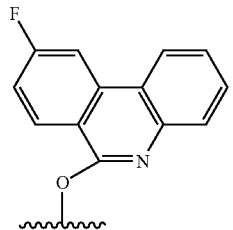 [SMILES: *Oc1nc2ccccc2c2cc(F)ccc12]

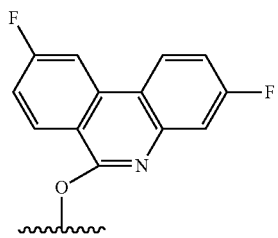 [SMILES: *Oc1nc2cc(F)ccc2c2cc(F)ccc12]

TABLE 1-continued
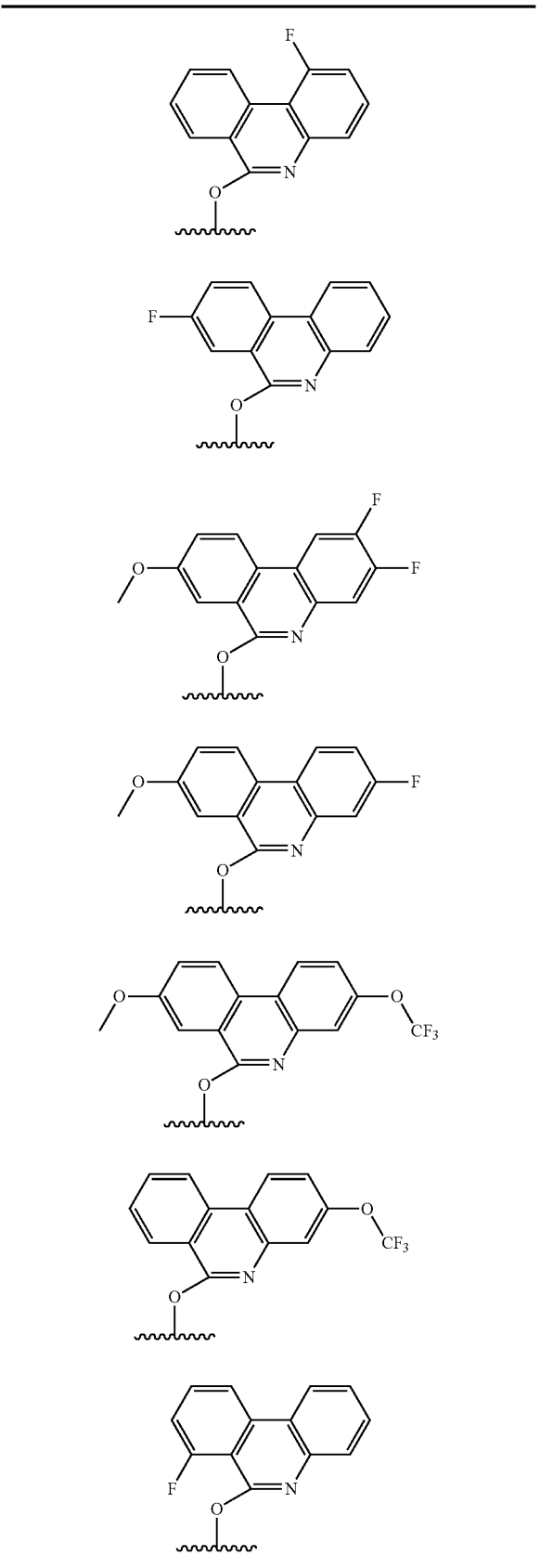
TABLE 1-continued
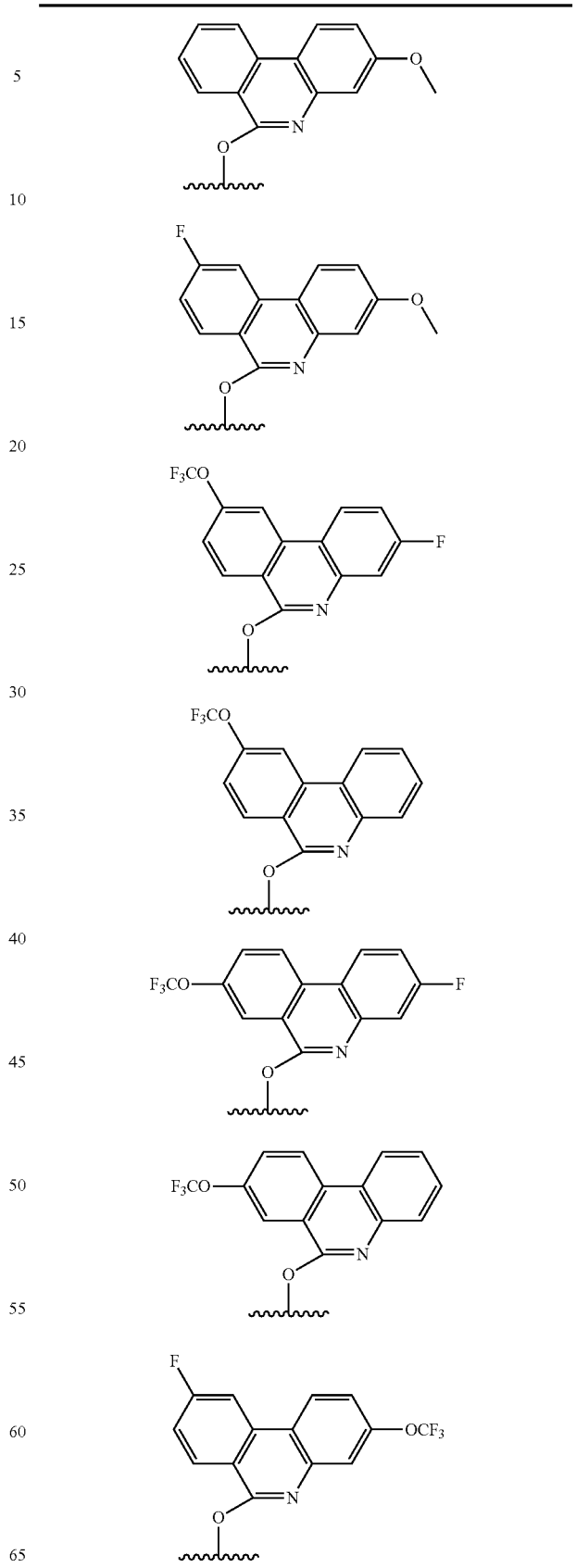

TABLE 1-continued

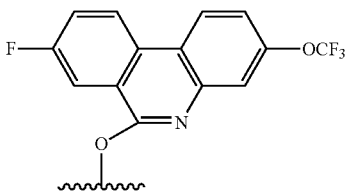 [SMILES: *Oc1nc2cc(OC(F)(F)F)ccc2c2ccc(F)cc12]

In certain embodiments, the invention provides a compound of formula III:

(III)

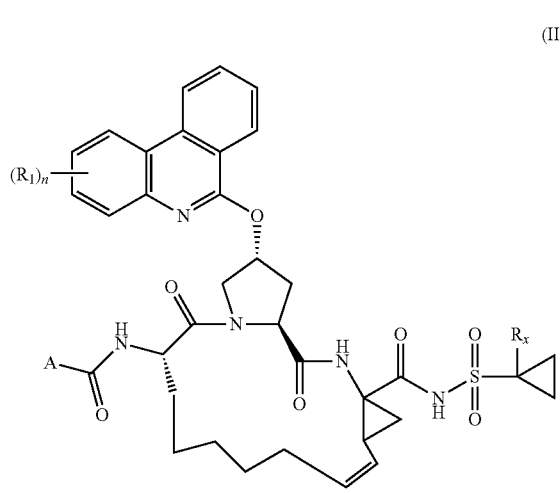

wherein:

A is optionally substituted alkyl, containing 0, 1, 2, or 3 heteroatoms selected from O, S, or N; optionally substituted aryl, or optionally substituted heteroaryl;

each $R_1$ is independently selected from halogen, hydroxy, —$OR_4$, —C(O)—O—$R_4$, —C(O)$R_4$, and —C(O)$NR_3R_4$, wherein at least one of $R_1$ is halogen or —$OR_4$;

$R_X$ is H or optionally substituted alkyl;

$R_3$ and $R_4$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted haloalkyl, optionally substituted aryl; optionally substituted heteroaryl; optionally substituted heterocyclic; optionally substituted carbocyclic; or hydrogen; and n is 1, 2, or 3.

In another embodiment, the invention provides a compound as described above, wherein

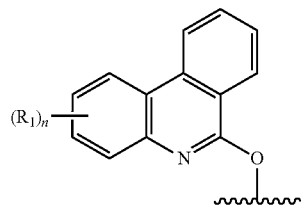

In another embodiment, the invention provides a compound as described above, wherein

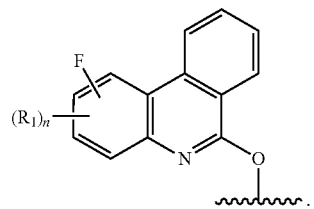

In another embodiment, the invention provides a compound as described above, wherein

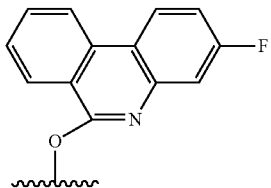 [SMILES: *Oc1nc2cc(F)ccc2c2ccccc12]

is selected from the following Table 1:

TABLE 1

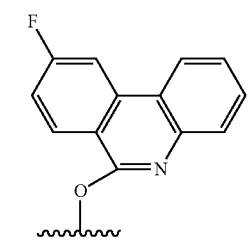 [SMILES: *Oc1nc2ccccc2c2cc(F)ccc12]

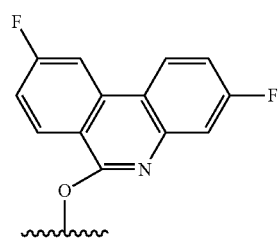 [SMILES: *Oc1nc2cc(F)ccc2c2cc(F)ccc12]

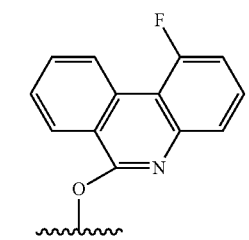 [SMILES: *Oc1nc2cccc(F)c2c2ccccc12]

TABLE 1-continued
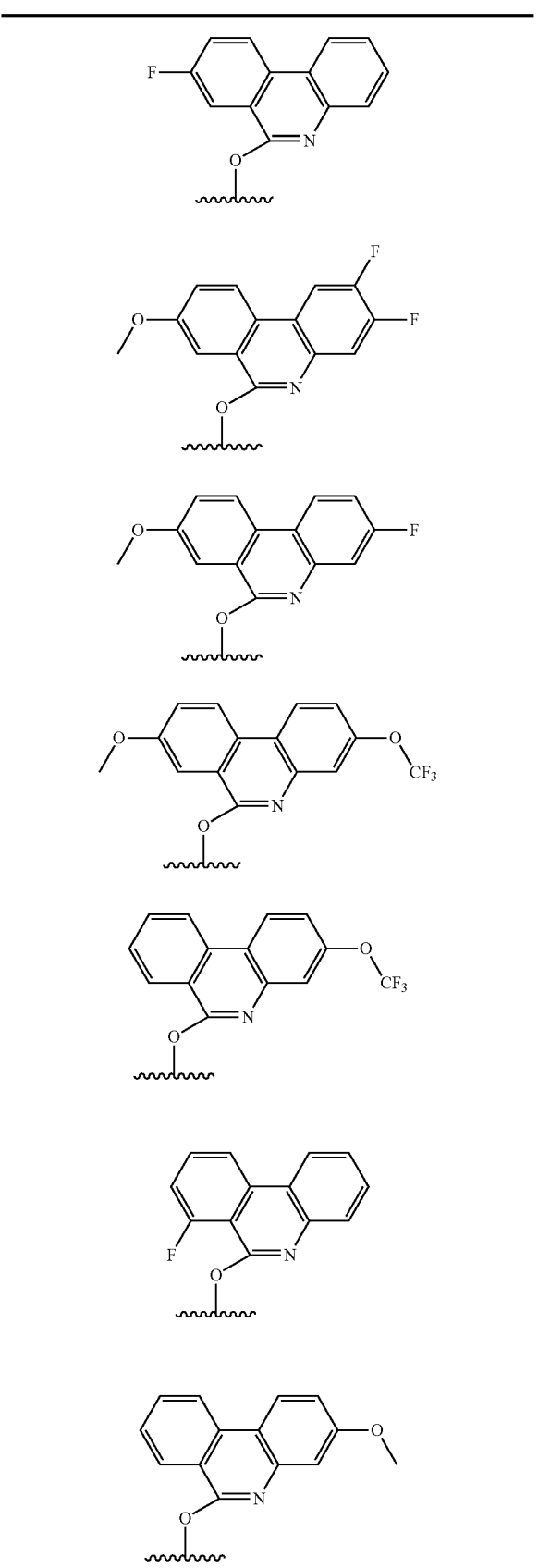
TABLE 1-continued
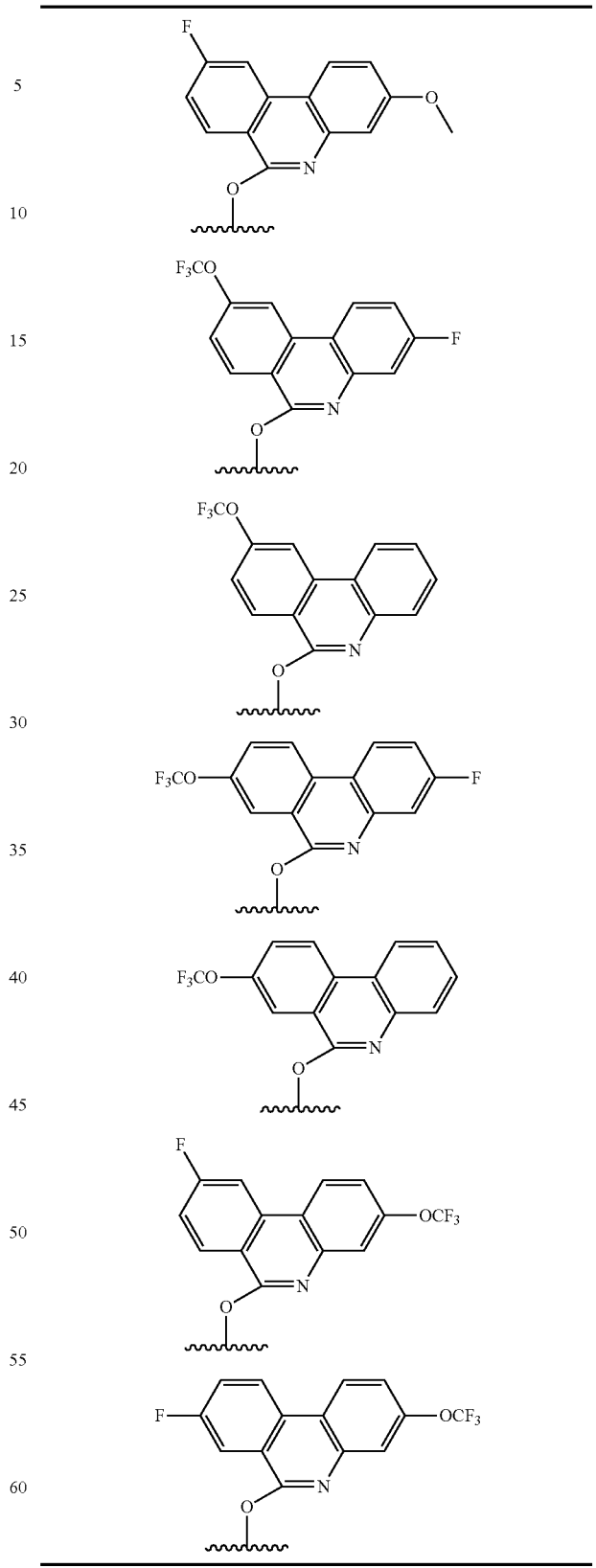
In various embodiments, A is optionally substituted —C$_1$-C$_8$ alkyl, containing 0, 1, 2, or 3 heteroatoms selected from O, S, or N; optionally substituted —C$_1$-C$_8$ haloalkyl, optionally substituted —$C_1$-$C_8$ hydroxyalkyl, optionally substituted aryl, optionally substituted —$C_1$-$C_8$ alkoxy, optionally substituted heteroaryl, optionally substituted —$C_3$-$C_{12}$ cycloalkyl, or optionally substituted —$C_3$-$C_{12}$ heterocyclyl.

In further embodiments, A is selected from Me, Et, Pr, i-Pr, Bu, s-Bu, t-Bu,

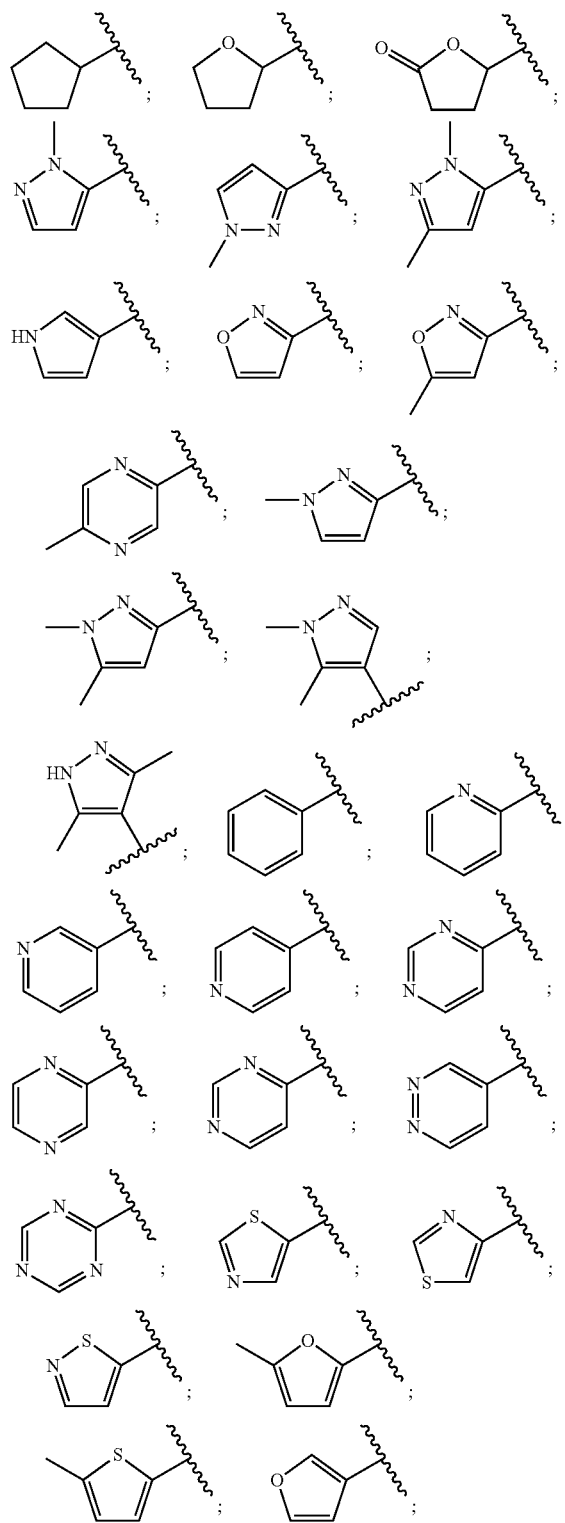

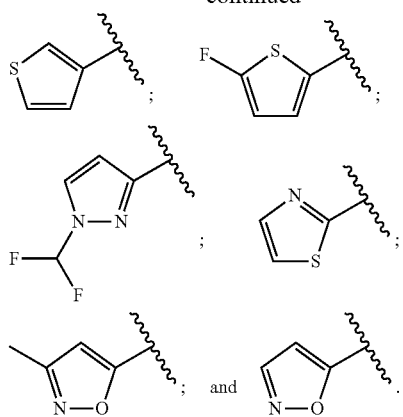

In another embodiment, A is

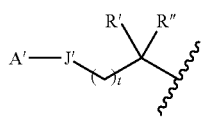

wherein:

J' is —NHC(O)—, or —NHC(O)O—;

A' is optionally substituted —$C_1$-$C_8$ alkyl, containing 0, 1, 2, or 3 heteroatoms selected from O, S, or N; optionally substituted aryl, or optionally substituted heteroaryl;

R' is H, optionally substituted —$C_1$-$C_8$ alkyl or optionally substituted —$C_3$-$C_{12}$ cycloalkyl, R'' is H, and t is 0 or 1.

In a further embodiment, A' is Me, Et, Pr, i-Pr, Bu, s-Bu, t-Bu, cyclopropyl, cyclobutyl, cyclopentyl, cyclohexyl, cycloheptyl, pyridinyl, pyrimidinyl, furanyl, thienyl, pyrrolyl, pyrazolyl, pyrrolidinyl, morpholinyl, piperidinyl, piperazinyl, imidazolyl,

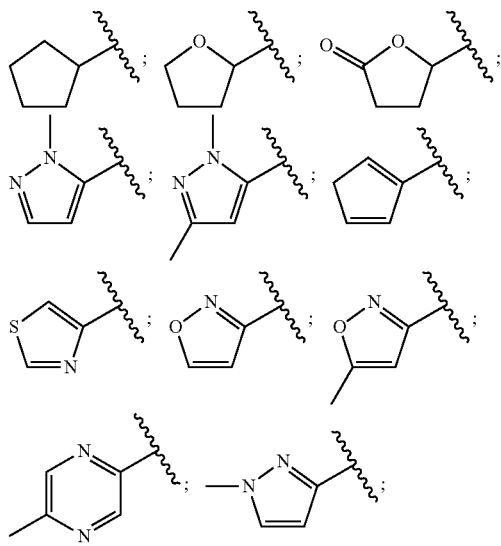

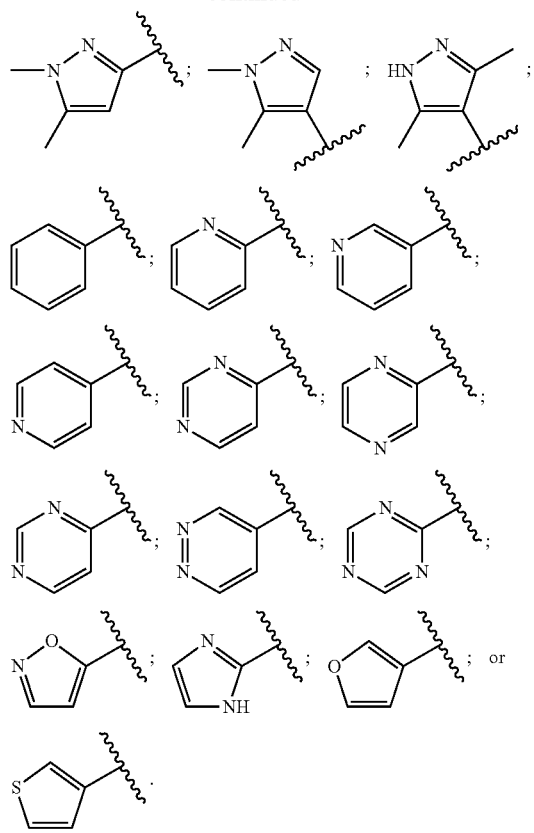

each of which is optionally substituted.

In a further embodiment, R' is Et, Pr, i-Pr, t-Bu, cyclopropyl, cyclobutyl, cyclopentyl, cyclohexyl, tetrahydropyran, $CH_2$-i-Pr, $CH_2$-t-Bu, $CH_2$-cyclopropyl, $CH_2$-cyclobutyl, $CH_2$-cyclopentyl, $CH_2$-cyclohexyl, or $CH_2$-tetrahydropyran.

In another embodiment, A is

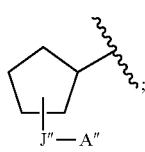

wherein, J" is —NC(O)— or —NC(O)O—; and A" is optionally substituted —$C_1$-$C_8$alkyl, containing 0, 1, 2, or 3 heteroatoms selected from O, S, or N, or optionally substituted heteroaryl.

In a further embodiment, A" is t-Bu, optionally substituted pyrazine, or optionally substituted isoxazole.

In another embodiment, A is —$CHR_Z(OH)$—, wherein $R_Z$ is cyclohexyl, i-Pr, i-Bu, t-Bu, or $CF_3$.

In another embodiment, A is $CHF_2$—$R_Y$, wherein $R_Y$ is Ph or Et.

In another embodiment, A is optionally substituted cycloalkyl. In another embodiment, A is optionally substituted heterocyclyl. In another embodiment, A is optionally substituted alkyl. In another embodiment, A is optionally substituted heteroaryl.

In one embodiment, A is selected from

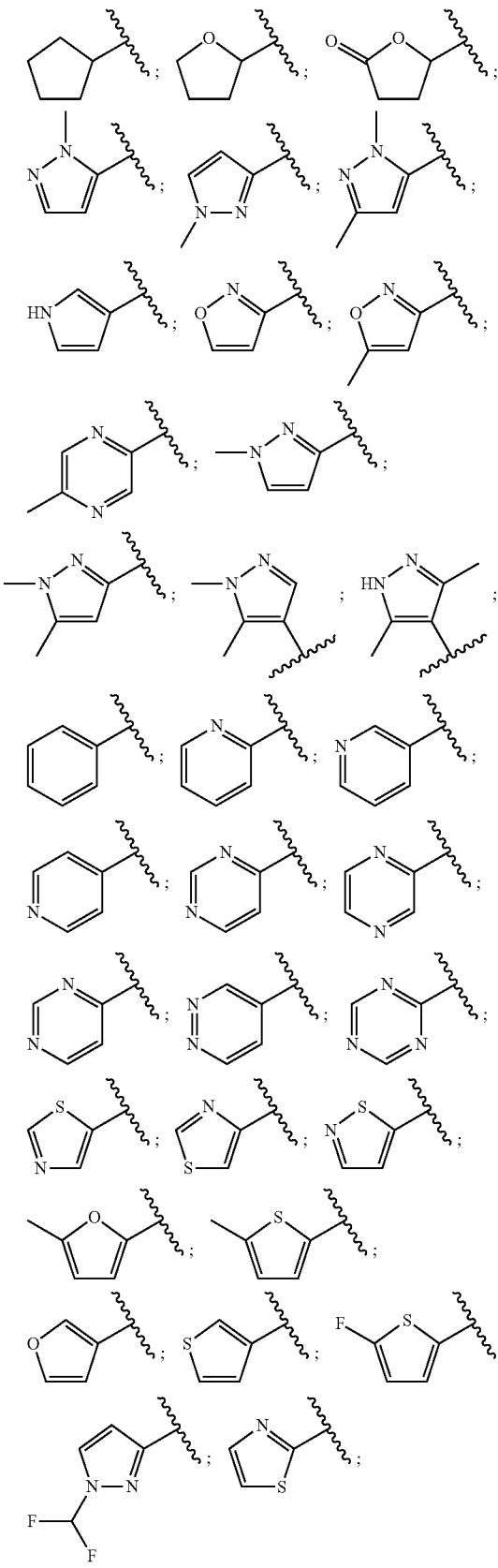

-continued

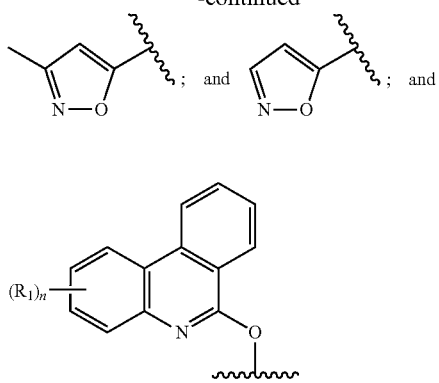; and

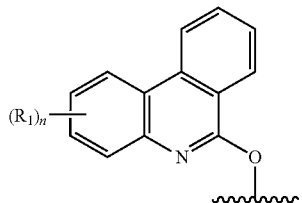

is selected from Table 1.

In another embodiment, A is

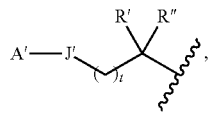

wherein A', J', R' R" and t are as defined previously, and

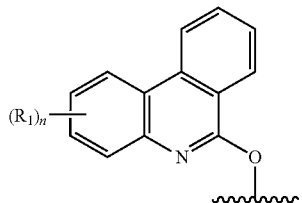

is selected from Table 1.

In another embodiment, A is

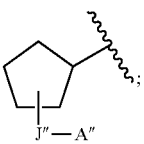

wherein, J" and A" are previously defined; and

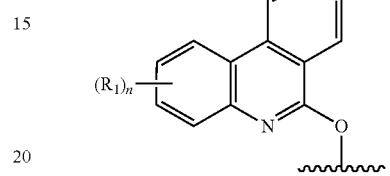

is selected from Table 1.

In another embodiment, A is —CHR$_Z$(OH)—, wherein R$_Z$ is cyclohexyl, i-Pr, i-Bu, t-Bu, or CF$_3$; and

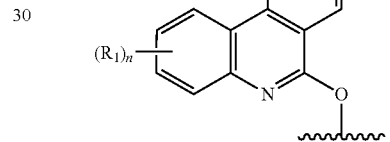

is selected from Table 1.

Representative compounds include, but are not limited to, the following compounds:

| Compound | nMI | Assay |
|---|---|---|
| | 0.1-0.5 | 1a stable replicon (nM) |
| | 0.1-0.5 | 1b stable replicon (nM) |
| | 0.1-0.5 | 1a transient replicon (nM) |
| | 0.1-0.5 | 1b transient replicon (nM) |
| | >1.0 | 3a transient replicon (nM) |

-continued

| Compound | nMI | Assay |
|---|---|---|
| | 0.1-0.5<br>0.1-0.5<br><0.1<br>0.1-0.5<br>>1.0 | 1a stable replicon (nM)<br>1b stable replicon (nM)<br>1a transient replicon (nM)<br>1b transient replicon (nM)<br>3a transient replicon (nM) |
| | 0.1-0.5<br>0.1-0.5<br><0.1<br>0.1-0.5<br>>1.0 | 1a stable replicon (nM)<br>1b stable replicon (nM)<br>1a transient replicon (nM)<br>1b transient replicon (nM)<br>3a transient replicon (nM) |
| | 0.1-0.5<br>0.1-0.5<br><0.1<br>0.1-0.5<br>>1.0 | 1a stable replicon (nM)<br>1b stable replicon (nM)<br>1a transient replicon (nM)<br>1b transient replicon (nM)<br>3a transient replicon (nM) |

-continued

| Compound | nMI | Assay |
|---|---|---|
| 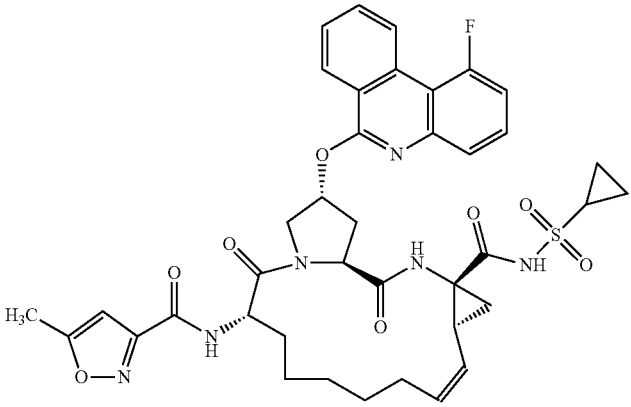 [SMILES: Cc1cc(C(=O)N[C@H]2CCCCC/C=C\[C@@H]3C[C@@]3(C(=O)NS(=O)(=O)C3CC3)NC(=O)[C@@H]3C[C@@H](Oc4nc5cccc(F)c5c5ccccc45)CN3C2=O)no1] | 0.5-1.0<br>0.1-0.5<br><0.1<br>0.1-0.5<br>>1.0 | 1a stable replicon (nM)<br>1b stable replicon (nM)<br>1a transient replicon (nM)<br>1b transient replicon (nM)<br>3a transient replicon (nM) |
| 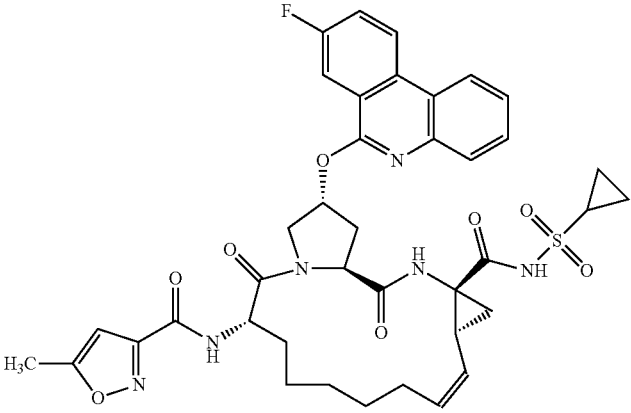 [SMILES: Cc1cc(C(=O)N[C@H]2CCCCC/C=C\[C@@H]3C[C@@]3(C(=O)NS(=O)(=O)C3CC3)NC(=O)[C@@H]3C[C@@H](Oc4nc5ccccc5c5ccc(F)cc45)CN3C2=O)no1] | 0.1-0.5<br>0.1-0.5<br><0.1<br>0.1-0.5<br>>1.0 | 1a stable replicon (nM)<br>1b stable replicon (nM)<br>1a transient replicon (nM)<br>1b transient replicon (nM)<br>3a transient replicon (nM) |
| 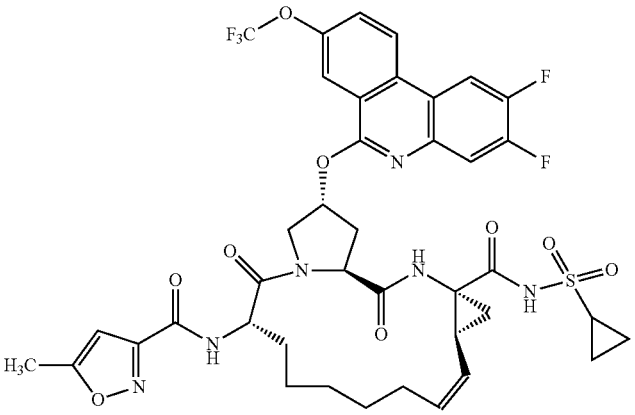 [SMILES: Cc1cc(C(=O)N[C@H]2CCCCC/C=C\[C@@H]3C[C@@]3(C(=O)NS(=O)(=O)C3CC3)NC(=O)[C@@H]3C[C@@H](Oc4nc5cc(F)c(F)cc5c5ccc(OC(F)(F)F)cc45)CN3C2=O)no1] | 0.5-1.0<br>0.5-1.0<br><0.1<br><0.1<br>>1.0 | 1a stable replicon (nM)<br>1b stable replicon (nM)<br>1a transient replicon (nM)<br>1b transient replicon (nM)<br>3a transient replicon (nM) |

-continued

| Compound | nMI | Assay |
|---|---|---|
| | 0.1-0.5<br>0.1-0.5<br><0.1<br><0.1<br>>1.0 | 1a stable replicon (nM)<br>1b stable replicon (nM)<br>1a transient replicon (nM)<br>1b transient replicon (nM)<br>3a transient replicon (nM) |
| | 0.5-1.0<br>0.5-1.0<br><0.1<br>0.1-0.5<br>>1.0 | 1a stable replicon (nM)<br>1b stable replicon (nM)<br>1a transient replicon (nM)<br>1b transient replicon (nM)<br>3a transient replicon (nM) |
| | 0.5-1.0<br>0.1-0.5<br>0.1-0.5<br>0.1-0.5<br>0.1-0.5 | 1a stable replicon (nM)<br>1b stable replicon (nM)<br>1a transient replicon (nM)<br>1b transient replicon (nM)<br>3a transient replicon (nM) |

-continued

| Compound | nMI | Assay |
|---|---|---|
| (structure with fluorophenanthridine, pyrrolidine, methylisoxazole, methylcyclopropylsulfonamide macrocycle) | 0.5-1.0<br>0.1-0.5<br><br><br>>1.0 | 1a stable replicon (nM)<br>1b stable replicon (nM)<br>1a transient replicon (nM)<br>1b transient replicon (nM)<br>3a transient replicon (nM) |
| (structure with methoxyphenanthridine, pyrrolidine, methylisoxazole, cyclopropylsulfonamide macrocycle) | 0.1-0.5<br>0.5-1.0<br><0.1<br>0.1-0.5<br>>1.0 | 1a stable replicon (nM)<br>1b stable replicon (nM)<br>1a transient replicon (nM)<br>1b transient replicon (nM)<br>3a transient replicon (nM) |
| (structure with fluorophenanthridine, pyrrolidine, methylpyrazole, methylcyclopropylsulfonamide macrocycle) | 0.1-0.5<br><0.1<br>0.1-0.5<br>0.1-0.5<br>0.5-1.0 | 1a stable replicon (nM)<br>1b stable replicon (nM)<br>1a transient replicon (nM)<br>1b transient replicon (nM)<br>3a transient replicon (nM) |

-continued

| Compound | nMI | Assay |
|---|---|---|
| (structure) | 0.5-1.0<br>0.1-0.5<br>0.1-0.5<br>0.1-0.5<br>0.5-1.0 | 1a stable replicon (nM)<br>1b stable replicon (nM)<br>1a transient replicon (nM)<br>1b transient replicon (nM)<br>3a transient replicon (nM) |
| (structure) | 0.5-1.0<br>0.5-1.0<br><0.1<br>0.1-0.5<br>>1.0 | 1a stable replicon (nM)<br>1b stable replicon (nM)<br>1a transient replicon (nM)<br>1b transient replicon (nM)<br>3a transient replicon (nM) |
| (structure) | 0.5-1.0<br>0.5-1.0<br><br><br>>1.0 | 1a stable replicon (nM)<br>1b stable replicon (nM)<br>1a transient replicon (nM)<br>1b transient replicon (nM)<br>3a transient replicon (nM) |

-continued

| Compound | nMI | Assay |
|---|---|---|
| (structure) | 0.5-1.0<br>0.1-0.5<br><0.1<br><0.1<br>0.5-1.0 | 1a stable replicon (nM)<br>1b stable replicon (nM)<br>1a transient replicon (nM)<br>1b transient replicon (nM)<br>3a transient replicon (nM) |
| (structure) | 0.5-1.0<br>0.1-0.5<br><0.1<br><0.1<br>0.5-1.0 | 1a stable replicon (nM)<br>1b stable replicon (nM)<br>1a transient replicon (nM)<br>1b transient replicon (nM)<br>3a transient replicon (nM) |
| (structure) | 0.5-1.0<br>0.1-0.5<br>0.1-0.5<br>0.1-0.5<br>>1.0 | 1a stable replicon (nM)<br>1b stable replicon (nM)<br>1a transient replicon (nM)<br>1b transient replicon (nM)<br>3a transient replicon (nM) |

-continued

| Compound | nMI | Assay |
|---|---|---|
| 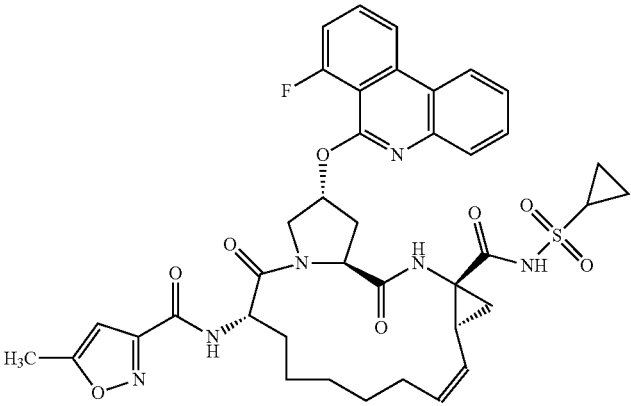 [SMILES: Cc1cc(C(=O)N[C@H]2CCCCC/C=C\[C@@H]3C[C@@]3(C(=O)NS(=O)(=O)C3CC3)NC(=O)[C@@H]3C[C@@H](Oc4nc5ccccc5c5cccc(F)c45)CN3C2=O)no1] | 0.1-0.5<br>0.1-0.5<br><0.1<br>0.1-0.5<br>>1.0 | 1a stable replicon (nM)<br>1b stable replicon (nM)<br>1a transient replicon (nM)<br>1b transient replicon (nM)<br>3a transient replicon (nM) |
| 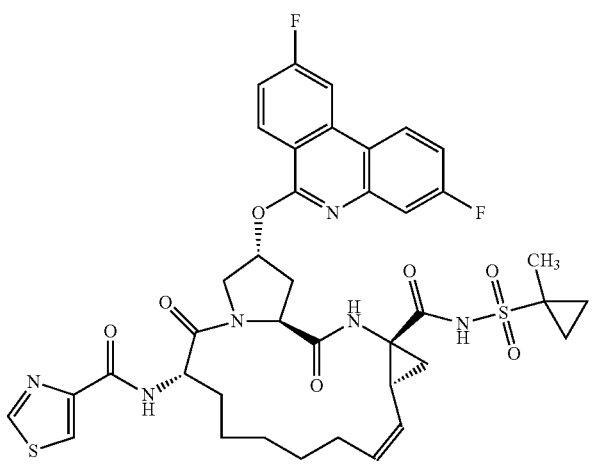 | 0.5-1.0<br>0.1-0.5<br><0.1<br>0.1-0.5<br>>1.0 | 1a stable replicon (nM)<br>1b stable replicon (nM)<br>1a transient replicon (nM)<br>1b transient replicon (nM)<br>3a transient replicon (nM) |
| 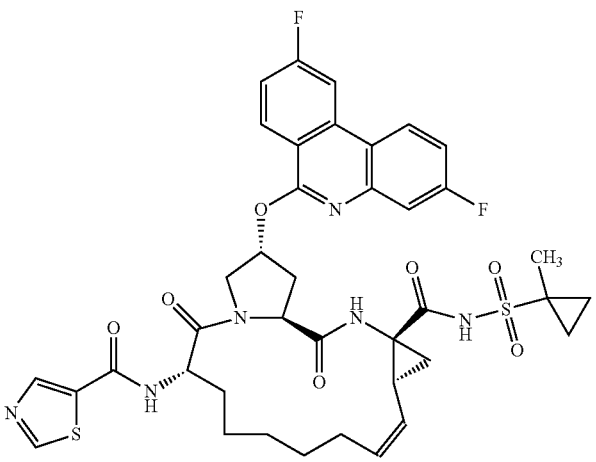 [SMILES: CC1(S(=O)(=O)NC(=O)[C@@]23C[C@H]2/C=C\CCCCC[C@H](NC(=O)c2cncs2)C(=O)N2C[C@H](Oc4nc5cc(F)ccc5c5cc(F)ccc45)C[C@H]2C(=O)N3)CC1] | >1.0<br>0.1-0.5<br><0.1<br>0.1-0.5<br>>1.0 | 1a stable replicon (nM)<br>1b stable replicon (nM)<br>1a transient replicon (nM)<br>1b transient replicon (nM)<br>3a transient replicon (nM) |

-continued

| Compound | nMI | Assay |
|---|---|---|
| | 0.5-1.0<br>0.1-0.5<br>0.1-0.5<br>0.1-0.5<br>>1.0 | 1a stable replicon (nM)<br>1b stable replicon (nM)<br>1a transient replicon (nM)<br>1b transient replicon (nM)<br>3a transient replicon (nM) |
| | 0.5-1.0<br><0.1<br><0.1<br>0.1-0.5<br>>1.0 | 1a stable replicon (nM)<br>1b stable replicon (nM)<br>1a transient replicon (nM)<br>1b transient replicon (nM)<br>3a transient replicon (nM) |
| | 0.5-1.0<br>0.1-0.5<br><0.1<br>0.1-0.5<br>>1.0 | 1a stable replicon (nM)<br>1b stable replicon (nM)<br>1a transient replicon (nM)<br>1b transient replicon (nM)<br>3a transient replicon (nM) |

-continued

| Compound | nMI | Assay |
|---|---|---|
| | 0.1-0.5<br>0.1-0.5<br><0.1<br>0.1-0.5<br>0.5-1.0 | 1a stable replicon (nM)<br>1b stable replicon (nM)<br>1a transient replicon (nM)<br>1b transient replicon (nM)<br>3a transient replicon (nM) |
| | 0.5-1.0<br>0.1-0.5<br>0.1-0.5<br>0.1-0.5<br>>1.0 | 1a stable replicon (nM)<br>1b stable replicon (nM)<br>1a transient replicon (nM)<br>1b transient replicon (nM)<br>3a transient replicon (nM) |
| | >1.0<br>0.1-0.5<br>0.1-0.5<br>0.1-0.5<br>>1.0 | 1a stable replicon (nM)<br>1b stable replicon (nM)<br>1a transient replicon (nM)<br>1b transient replicon (nM)<br>3a transient replicon (nM) |

-continued

| Compound | nMI | Assay |
|---|---|---|
| 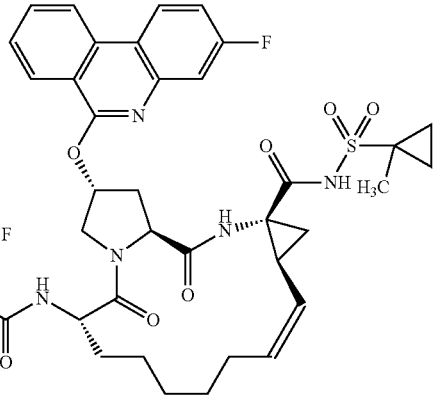 | 0.5-1.0<br>0.1-0.5<br><0.1<br>0.1-0.5<br>>1.0 | 1a stable replicon (nM)<br>1b stable replicon (nM)<br>1a transient replicon (nM)<br>1b transient replicon (nM)<br>3a transient replicon (nM) |
| 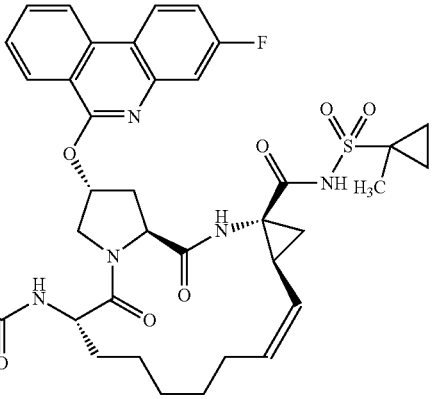 | 0.5-1.0<br>0.1-0.5<br>0.1-0.5<br>0.1-0.5<br><1.0 | 1a stable replicon (nM)<br>1b stable replicon (nM)<br>1a transient replicon (nM)<br>1b transient replicon (nM)<br>3a transient replicon (nM) |
| 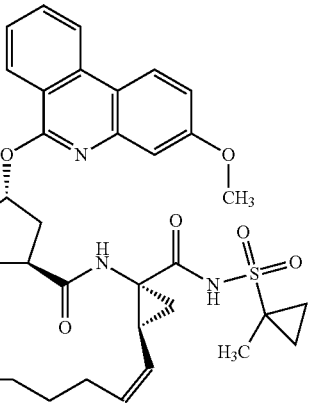 | 0.1-0.5<br>0.1-0.5<br><0.1<br>0.1-0.5<br>>1.0 | 1a stable replicon (nM)<br>1b stable replicon (nM)<br>1a transient replicon (nM)<br>1b transient replicon (nM)<br>3a transient replicon (nM) |

-continued

| Compound | nMI | Assay |
|---|---|---|
| | 0.5-1.0 | 1a stable replicon (nM) |
| | 0.1-0.5 | 1b stable replicon (nM) |
| | 0.1-0.5 | 1a transient replicon (nM) |
| | 0.1-0.5 | 1b transient replicon (nM) |
| | <1.0 | 3a transient replicon (nM) |
| | 0.1-0.5 | 1a stable replicon (nM) |
| | 0.1-0.5 | 1b stable replicon (nM) |
| | | 1a transient replicon (nM) |
| | | 1b transient replicon (nM) |
| | >1.0 | 3a transient replicon (nM) |
| | 0.5-1.0 | 1a stable replicon (nM) |
| | 0.1-0.5 | 1b stable replicon (nM) |
| | <0.1 | 1a transient replicon (nM) |
| | 0.1-0.5 | 1b transient replicon (nM) |
| | >1.0 | 3a transient replicon (nM) |

-continued

| Compound | nMI | Assay |
|---|---|---|
| | 0.1-0.5<br>0.1-0.5<br><0.1<br><0.1<br>>1.0 | 1a stable replicon (nM)<br>1b stable replicon (nM)<br>1a transient replicon (nM)<br>1b transient replicon (nM).<br>3a transient replicon (nM) |
| | 0.5-1.0<br>0.1-0.5<br>0.1-0.5<br>0.1-0.5<br>>1.0 | 1a stable replicon (nM)<br>1b stable replicon (nM)<br>1a transient replicon (nM)<br>1b transient replicon (nM)<br>3a transient replicon (nM) |
| | 0.1-0.5<br><0.1<br>0.1-0.5<br>0.1-0.5<br> | 1a stable replicon (nM)<br>1b stable replicon (nM)<br>1a transient replicon (nM)<br>1b transient replicon (nM)<br>3a transient replicon (nM) |

| Compound | nMI | Assay |
|---|---|---|
| 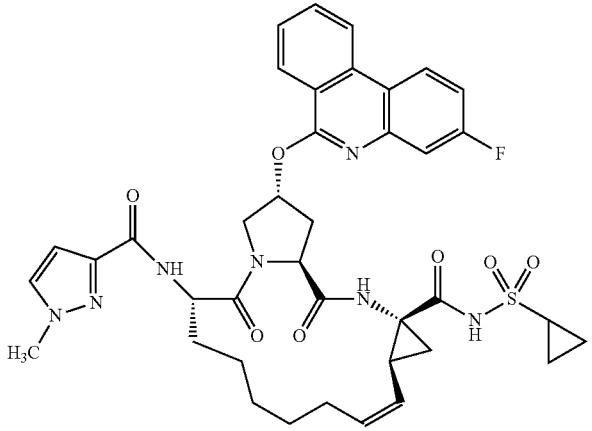 [SMILES: Cn1ccc(C(=O)N[C@H]2CCCCC/C=C\[C@@H]3C[C@@]3(C(=O)NS(=O)(=O)C3CC3)NC(=O)[C@@H]3C[C@@H](Oc4nc5cc(F)ccc5c5ccccc45)CN3C2=O)n1] | 0.1-0.5<br><0.1<br>0.1-0.5<br>0.1-0.5 | 1a stable replicon (nM)<br>1b stable replicon (nM)<br>1a transient replicon (nM)<br>1b transient replicon (nM)<br>3a transient replicon (nM) |
| 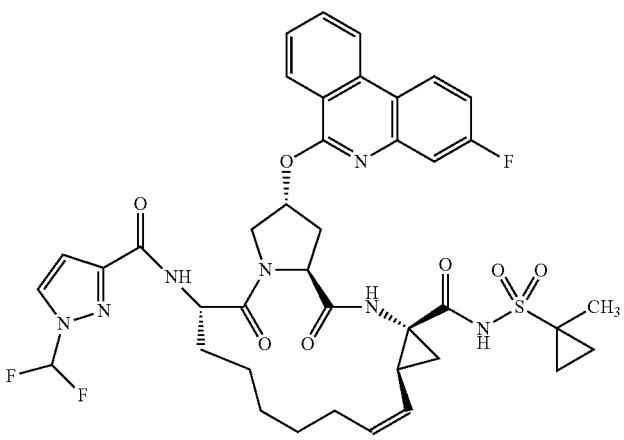 [SMILES: CC1(S(=O)(=O)NC(=O)[C@@]23C[C@H]2/C=C\CCCCC[C@H](NC(=O)c2ccn(C(F)F)n2)C(=O)N2C[C@H](Oc4nc5cc(F)ccc5c5ccccc45)C[C@H]2C(=O)N3)CC1] | 0.5-1.0<br>0.1-0.5<br>0.1-0.5<br>0.1-0.5 | 1a stable replicon (nM)<br>1b stable replicon (nM)<br>1a transient replicon (nM)<br>1b transient replicon (nM)<br>3a transient replicon (nM) |
| 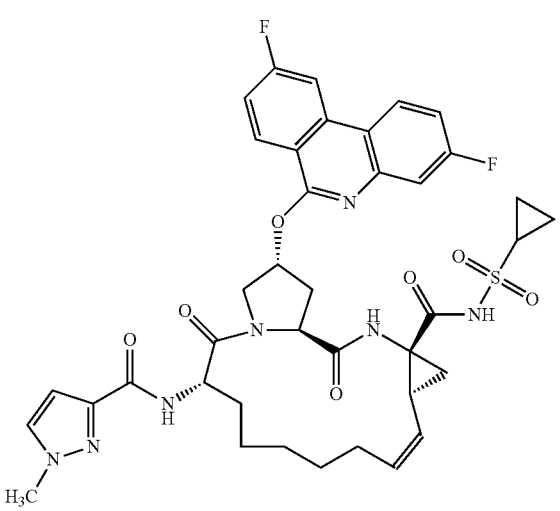 [SMILES: Cn1ccc(C(=O)N[C@H]2CCCCC/C=C\[C@@H]3C[C@@]3(C(=O)NS(=O)(=O)C3CC3)NC(=O)[C@@H]3C[C@@H](Oc4nc5cc(F)ccc5c5cc(F)ccc45)CN3C2=O)n1] | 0.5-1.0<br><0.1<br>0.1-0.5<br>0.1-0.5 | 1a stable replicon (nM)<br>1b stable replicon (nM)<br>1a transient replicon (nM)<br>1b transient replicon (nM)<br>3a transient replicon (nM) |

-continued

| Compound | nMI | Assay |
|---|---|---|
| 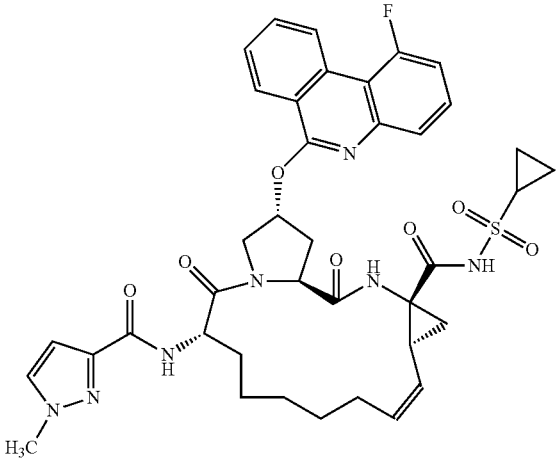 [SMILES: Cn1ccc(C(=O)N[C@H]2CCCCC/C=C\[C@@H]3C[C@@]3(C(=O)NS(=O)(=O)C3CC3)NC(=O)[C@@H]3C[C@@H](Oc4nc5cccc(F)c5c5ccccc45)CN3C2=O)n1] | 0.5-1.0<br><0.1<br>0.5-1.0<br>0.1-0.5 | 1a stable replicon (nM)<br>1b stable replicon (nM)<br>1a transient replicon (nM)<br>1b transient replicon (nM)<br>3a transient replicon (nM) |
| 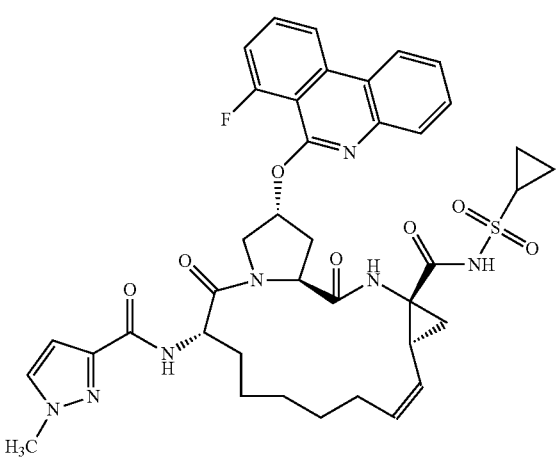 [SMILES: Cn1ccc(C(=O)N[C@H]2CCCCC/C=C\[C@@H]3C[C@@]3(C(=O)NS(=O)(=O)C3CC3)NC(=O)[C@@H]3C[C@@H](Oc4nc5ccccc5c5cccc(F)c45)CN3C2=O)n1] | 0.5-1.0<br><0.1<br>0.1-0.5<br>0.5-1.0 | 1a stable replicon (nM)<br>1b stable replicon (nM)<br>1a transient replicon (nM)<br>1b transient replicon (nM)<br>3a transient replicon (nM) |
| 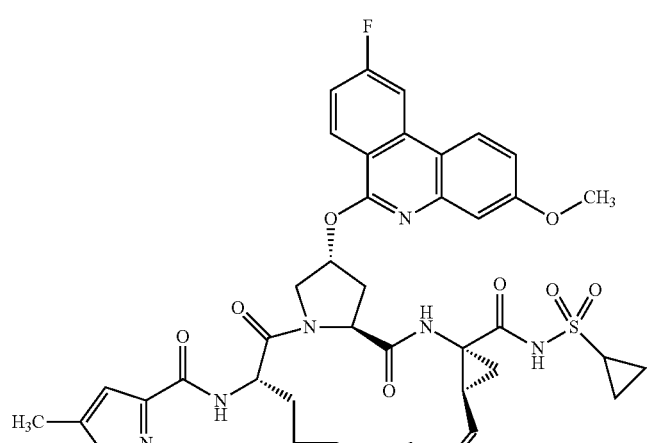 | 0.1-0.5<br>0.1-0.5<br>>1.0 | 1a stable replicon (nM)<br>1b stable replicon (nM)<br>1a transient replicon (nM)<br>1b transient replicon (nM)<br>3a transient replicon (nM) |

-continued

| Compound | nMI | Assay |
|---|---|---|
| | 0.1-0.5 | 1a stable replicon (nM) |
| | 0.1-0.5 | 1b stable replicon (nM) |
| | 0.1-0.5 | 1a transient replicon (nM) |
| | 0.5-1.0 | 1b transient replicon (nM) |
| | 0.5-1.0 | 3a transient replicon (nM) |
| | 0.1-0.5 | 1a stable replicon (nM) |
| | <0.1 | 1b stable replicon (nM) |
| | <0.1 | 1a transient replicon (nM) |
| | 0.1-0.5 | 1b transient replicon (nM) |
| | 0.1-0.5 | 3a transient replicon (nM) |
| | 0.5-1.0 | 1a stable replicon (nM) |
| | <0.1 | 1b stable replicon (nM) |
| | 0.1-0.5 | 1a transient replicon (nM) |
| | 0.1-0.5 | 1b transient replicon (nM) |
| | >1.0 | 3a transient replicon (nM) |

| Compound | nMI | Assay |
|---|---|---|
| 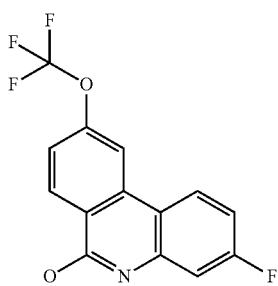 | <0.1<br>0.1-0.5<br>>1.0 | 1a stable replicon (nM)<br>1b stable replicon (nM)<br>1a transient replicon (nM)<br>1b transient replicon (nM)<br>3a transient replicon (nM) |
| 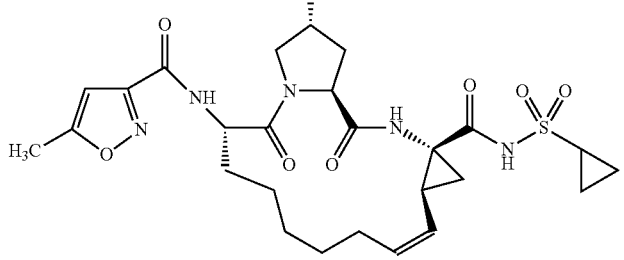 | <0.1<br>0.1-0.5<br>>1.0 | 1a stable replicon (nM)<br>1b stable replicon (nM)<br>1a transient replicon (nM)<br>1b transient replicon (nM)<br>3a transient replicon (nM) |
| 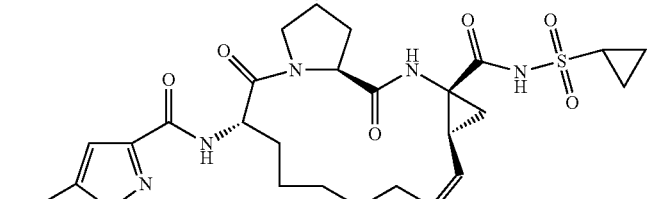 | 0.1-0.5<br>0.1-0.5<br>>1.0 | 1a stable replicon (nM)<br>1b stable replicon (nM)<br>1a transient replicon (nM)<br>1b transient replicon (nM)<br>3a transient replicon (nM) |

-continued
| Compound | nMI | Assay |
|---|---|---|
| 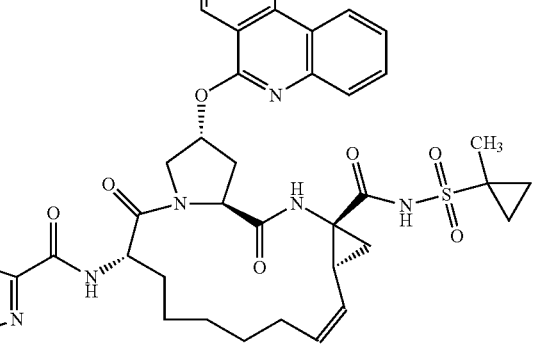 | <0.1<br>0.1-0.5<br>0.5-1.0 | 1a stable replicon (nM)<br>1b stable replicon (nM)<br>1a transient replicon (nM)<br>1b transient replicon (nM)<br>3a transient replicon (nM) |
| 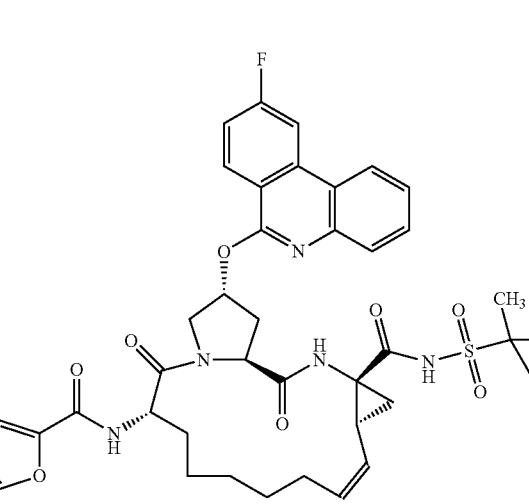 | 0.1-0.5<br>0.1-0.5<br>0.1-0.5 | 1a stable replicon (nM)<br>1b stable replicon (nM)<br>1a transient replicon (nM)<br>1b transient replicon (nM)<br>3a transient replicon (nM) |
| 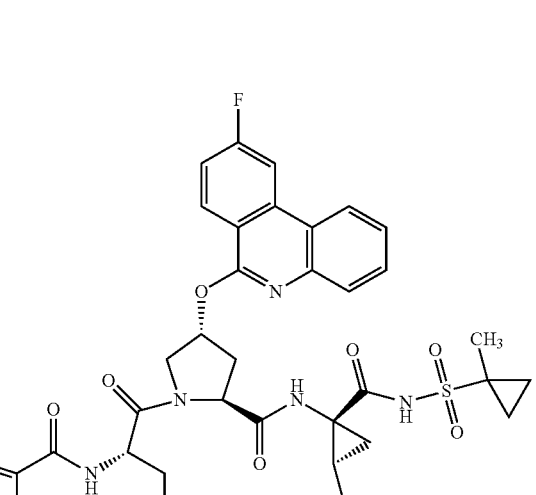 | | |

| Compound | nM | Assay |
|---|---|---|
| | <0.1<br>0.1-0.5<br>0.1-0.5<br>0.1-0.5 | 1a stable replicon (nM)<br>1b stable replicon (nM)<br>1a transient replicon (nM)<br>1b transient replicon (nM)<br>3a transient replicon (nM) |
| | <0.1<br><0.1<br><0.1<br>0.1-0.5 | 1a stable replicon (nM)<br>1b stable replicon (nM)<br>1a transient replicon (nM)<br>1b transient replicon (nM)<br>3a transient replicon (nM) |

| Compound | nMI Assay |
|----------|-----------|

| Compound | nMI | Assay |
|---|---|---|
| | 0.1–0.5 | 1a stable replicon (nM) |
| | 0.1–0.5 | 1b stable replicon (nM) |
| | >1.0 | 1a transient replicon (nM) |
| | | 1b transient replicon (nM) |
| | | 3a transient replicon (nM) |

| Compound | nMI Assay |
|---|---|

0.1-0.5  1a transient replicon (nM)
0.1-0.5  1b transient replicon (nM)
>1.0    3a transient replicon (nM)

1a stable replicon (nM)
1b stable replicon (nM)

| Compound | nMI | Assay |
|---|---|---|
| 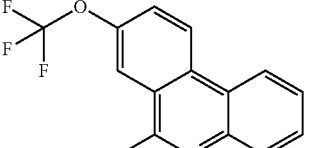 | 0.1-0.5<br>0.1-0.5<br>0.1-0.5 | 1a stable replicon (nM)<br>1b stable replicon (nM)<br>1a transient replicon (nM)<br>1b transient replicon (nM)<br>3a transient replicon (nM) |
| 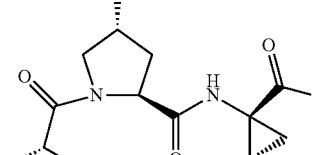 | | |
| 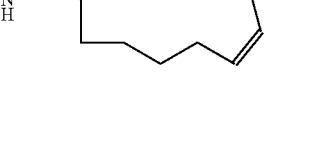 | | |

-continued

| Compound | nMI Assay |
|---|---|

| Compound | nMI Assay |
|---|---|
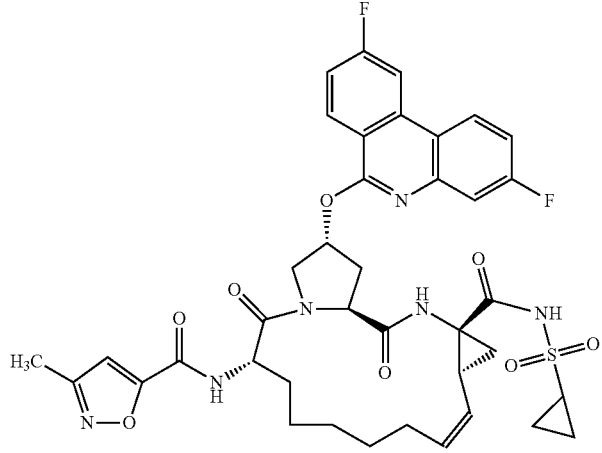 [SMILES: Cc1cc(C(=O)N[C@H]2CCCCC/C=C\[C@@H]3C[C@@]3(C(=O)NS(=O)(=O)C3CC3)NC(=O)[C@@H]3C[C@@H](Oc4nc5cc(F)ccc5c5cc(F)ccc45)CN3C2=O)on1]
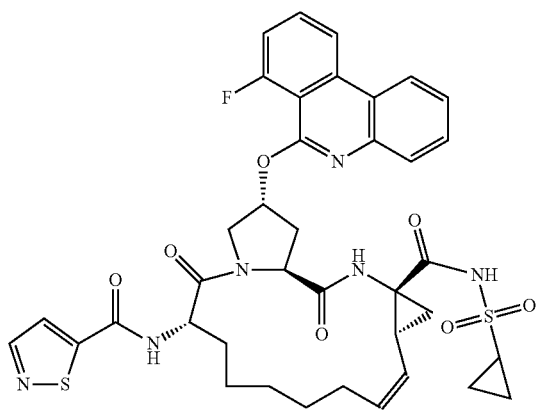 [SMILES: O=C(N[C@H]1CCCCC/C=C\[C@@H]2C[C@@]2(C(=O)NS(=O)(=O)C2CC2)NC(=O)[C@@H]2C[C@@H](Oc3nc4ccccc4c4cccc(F)c34)CN2C1=O)c1ccns1]
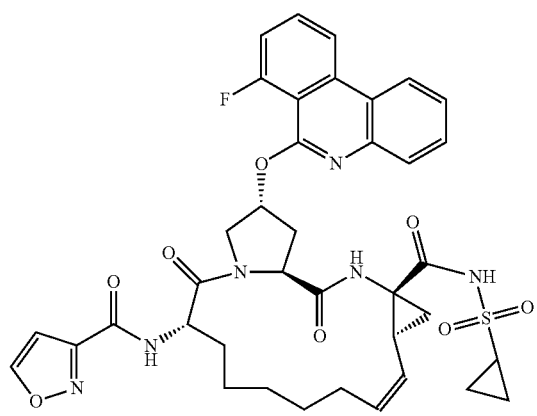 [SMILES: O=C(N[C@H]1CCCCC/C=C\[C@@H]2C[C@@]2(C(=O)NS(=O)(=O)C2CC2)NC(=O)[C@@H]2C[C@@H](Oc3nc4ccccc4c4cccc(F)c34)CN2C1=O)c1ccon1]

| Compound | nM[1] Assay |
|---|---|
| 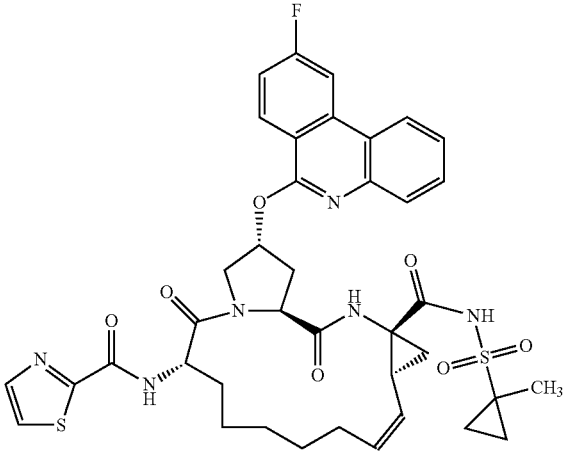 [SMILES: CC1(S(=O)(=O)NC(=O)[C@@]23C[C@H]2/C=C\CCCCC[C@H](NC(=O)c2nccs2)C(=O)N2C[C@H](Oc4nc5ccccc5c5cc(F)ccc45)C[C@H]2C(=O)N3)CC1] | |
| 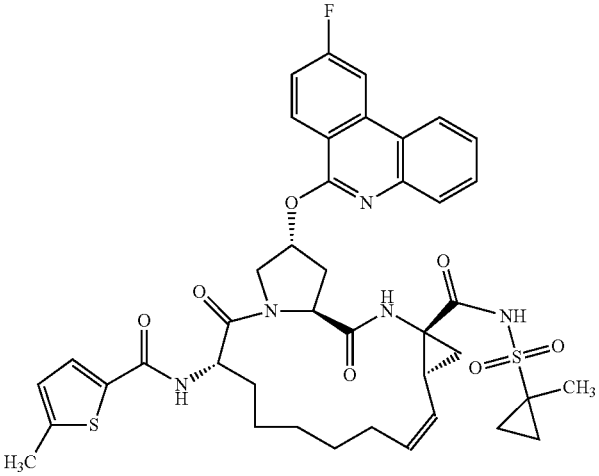 | 1a stable replicon (nM)<br>1b stable replicon (nM)<br>0.1-0.5 1a transient replicon (nM)<br>0.1-0.5 1b transient replicon (nM)<br>>1.0 3a transient replicon (nM) |
| 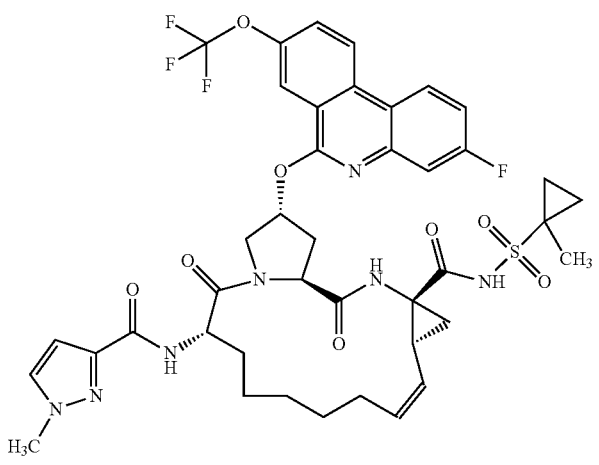 [SMILES: Cn1ccc(C(=O)N[C@H]2CCCCC/C=C\[C@@H]3C[C@@]3(C(=O)NS(=O)(=O)C3(C)CC3)NC(=O)[C@@H]3C[C@@H](Oc4nc5cc(F)ccc5c5ccc(OC(F)(F)F)cc45)CN3C2=O)n1] | 1a stable replicon (nM)<br>1b stable replicon (nM)<br><0.1 1a transient replicon (nM)<br>0.1-0.5 1b transient replicon (nM)<br>0.1-0.5 3a transient replicon (nM) |

-continued

| Compound | nMI | Assay |
|---|---|---|
| (structure) | <0.1<br>0.1-0.5<br>>1.0 | 1a stable replicon (nM)<br>1b stable replicon (nM)<br>1a transient replicon (nM)<br>1b transient replicon (nM)<br>3a transient replicon (nM) |
| (structure) | 0.1-0.5<br>0.1-0.5<br>>1.0 | 1a stable replicon (nM)<br>1b stable replicon (nM)<br>1a transient replicon (nM)<br>1b transient replicon (nM)<br>3a transient replicon (nM) |
| (structure) | <0.1<br>0.1-0.5<br>>1.0 | 1a stable replicon (nM)<br>1b stable replicon (nM)<br>1a transient replicon (nM)<br>1b transient replicon (nM)<br>3a transient replicon (nM) |

-continued

| Compound | nMI | Assay |
|---|---|---|
| | | 1a stable replicon (nM) |
| | | 1b stable replicon (nM) |
| | 0.1-0.5 | 1a transient replicon (nM) |
| | 0.1-0.5 | 1b transient replicon (nM) |
| | <0.1 | 3a transient replicon (nM) |
| | | 1a stable replicon (nM) |
| | | 1b stable replicon (nM) |
| | <0.1 | 1a transient replicon (nM) |
| | <0.1 | 1b transient replicon (nM) |
| | >1.0 | 3a transient replicon (nM) |
| | | 1a stable replicon (nM) |
| | | 1b stable replicon (nM) |
| | <0.1 | 1a transient replicon (nM) |
| | <0.1 | 1b transient replicon (nM) |
| | 0.1-0.5 | 3a transient replicon (nM) |

-continued

| Compound | nMI | Assay |
|---|---|---|
| (structure) | 0.1-0.5<br>0.1-0.5<br>0.1-0.5 | 1a stable replicon (nM)<br>1b stable replicon (nM)<br>1a transient replicon (nM)<br>1b transient replicon (nM)<br>3a transient replicon (nM) |
| (structure) | 0.5-1.0<br>0.1-0.5<br>0.1-0.5 | 1a stable replicon (nM)<br>1b stable replicon (nM)<br>1a transient replicon (nM)<br>1b transient replicon (nM)<br>3a transient replicon (nM) |
| (structure) | <0.1<br><0.1<br>0.5-1.0 | 1a stable replicon (nM)<br>1b stable replicon (nM)<br>1a transient replicon (nM)<br>1b transient replicon (nM)<br>3a transient replicon (nM) |

US 8,951,964 B2

87 88

-continued

| Compound | nMI | Assay |
|---|---|---|
| 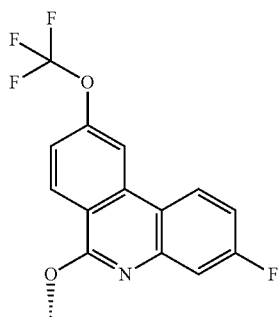 | 0.1-0.5<br>0.1-0.5<br>>1.0 | 1a stable replicon (nM)<br>1b stable replicon (nM)<br>1a transient replicon (nM)<br>1b transient replicon (nM)<br>3a transient replicon (nM) |
| 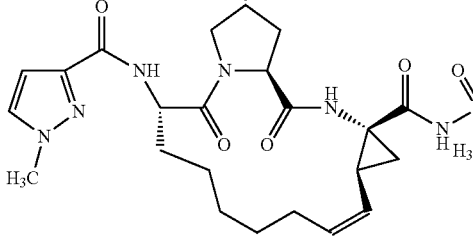 | <0.1<br>0.1-0.5<br>>1.0 | 1a stable replicon (nM)<br>1b stable replicon (nM)<br>1a transient replicon (nM)<br>1b transient replicon (nM)<br>3a transient replicon (nM) |
| 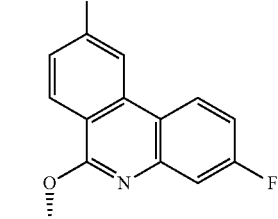 | 0.1-0.5<br>0.1-0.5<br>>1.0 | 1a stable replicon (nM)<br>1b stable replicon (nM)<br>1a transient replicon (nM)<br>1b transient replicon (nM)<br>3a transient replicon (nM) |

| Compound | nMI | Assay |
|---|---|---|
| (structure) | 0.1-0.5<br>0.1-0.5<br>0.1-0.5 | 1a stable replicon (nM)<br>1b stable replicon (nM)<br>1a transient replicon (nM)<br>1b transient replicon (nM)<br>3a transient replicon (nM) |
| (structure) | <0.1<br>0.1-0.5<br>0.1-0.5 | 1a stable replicon (nM)<br>1b stable replicon (nM)<br>1a transient replicon (nM)<br>1b transient replicon (nM)<br>3a transient replicon (nM) |
| (structure) | 0.1-0.5<br>0.1-0.5<br>0.5-1.0 | 1a stable replicon (nM)<br>1b stable replicon (nM)<br>1a transient replicon (nM)<br>1b transient replicon (nM)<br>3a transient replicon (nM) |

-continued

| Compound | nMI | Assay |
|---|---|---|
| (structure) | <0.1<br><0.1<br>>1.0 | 1a stable replicon (nM)<br>1b stable replicon (nM)<br>1b transient replicon (nM)<br>1a transient replicon (nM)<br>3a transient replicon (nM) |
| (structure) | 0.1-0.5<br>0.1-0.5<br>>1.0 | 1a stable replicon (nM)<br>1b stable replicon (nM)<br>1a transient replicon (nM)<br>1b transient replicon (nM)<br>3a transient replicon (nM) |
| (structure) | <0.1<br><0.1<br>0.5-1.0 | 1a stable replicon (nM)<br>1b stable replicon (nM)<br>1a transient replicon (nM)<br>1b transient replicon (nM)<br>3a transient replicon (nM) |

-continued

| Compound | nMI | Assay |
|---|---|---|
| (structure) | 0.1-0.5<br>0.1-0.5<br>>1.0 | 1a stable replicon (nM)<br>1b stable replicon (nM)<br>1a transient replicon (nM)<br>1b transient replicon (nM)<br>3a transient replicon (nM) |
| (structure) | 0.1-0.5<br>0.1-0.5<br>>1.0 | 1a stable replicon (nM)<br>1b stable replicon (nM)<br>1a transient replicon (nM)<br>1b transient replicon (nM)<br>3a transient replicon (nM) |
| (structure) | <0.1<br><0.1<br>0.1-0.5 | 1a stable replicon (nM)<br>1b stable replicon (nM)<br>1a transient replicon (nM)<br>1b transient replicon (nM)<br>3a transient replicon (nM) |

| Compound | nMI Assay |
|---|---|
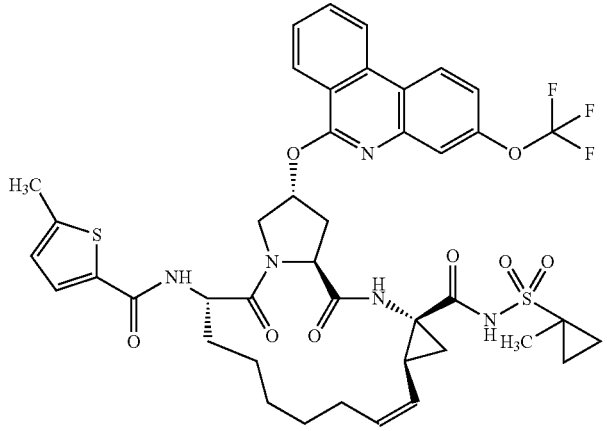 [SMILES: Cc1ccc(C(=O)N[C@H]2CCCCC/C=C\[C@@H]3C[C@@]3(C(=O)NS(=O)(=O)C3(C)CC3)NC(=O)[C@@H]3C[C@@H](Oc4nc5cc(OC(F)(F)F)ccc5c5ccccc45)CN3C2=O)s1]
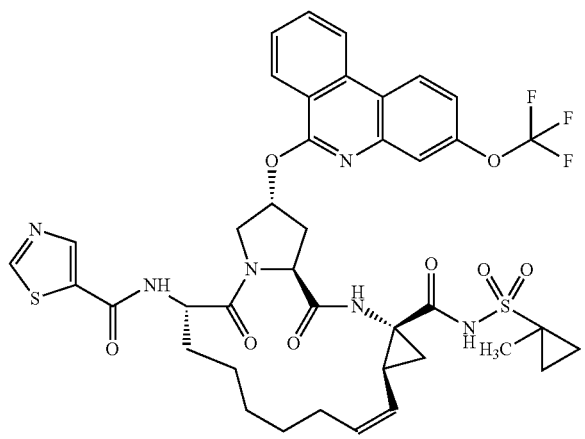 [SMILES: CC1(S(=O)(=O)NC(=O)[C@@]23C[C@H]2/C=C\CCCCC[C@H](NC(=O)c2cncs2)C(=O)N2C[C@H](Oc4nc5cc(OC(F)(F)F)ccc5c5ccccc45)C[C@H]2C(=O)N3)CC1]
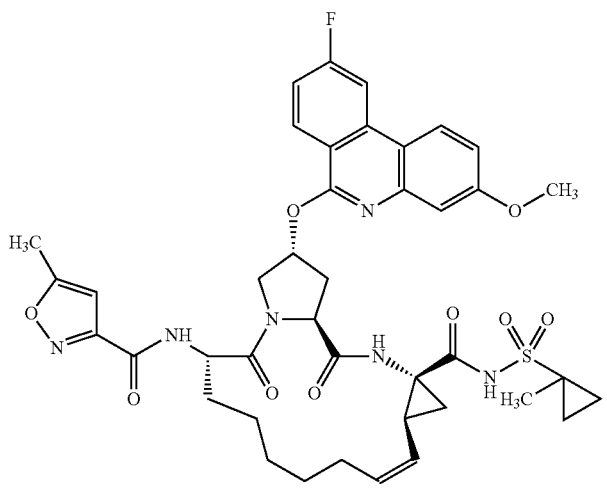 [SMILES: COc1ccc2c(c1)nc(O[C@@H]1C[C@H]3C(=O)N[C@]4(C(=O)NS(=O)(=O)C5(C)CC5)C[C@H]4/C=C\CCCCC[C@H](NC(=O)c4cc(C)on4)C(=O)N3C1)c1ccc(F)cc12]

-continued

| Compound | nMI Assay |
|---|---|

| Compound | nMI | Assay |
|---|---|---|
| | <0.1<br><0.1<br>>1.0 | 1a stable replicon (nM)<br>1b stable replicon (nM)<br>1a transient replicon (nM)<br>1b transient replicon (nM)<br>3a transient replicon (nM) |

| Compound | nMI Assay |
|----------|-----------|
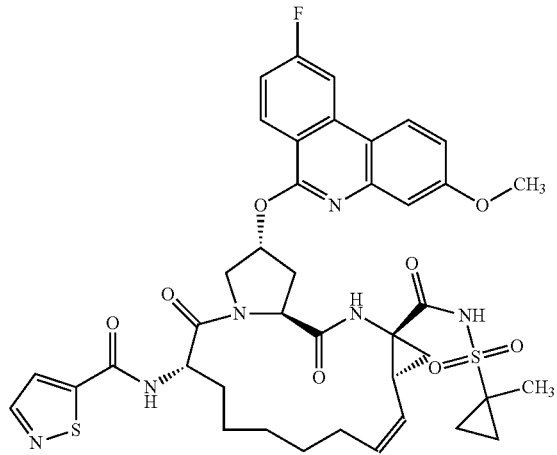 [SMILES: COc1ccc2c(c1)nc(O[C@@H]1C[C@H]3C(=O)N[C@]4(C(=O)NS(=O)(=O)C5(C)CC5)C[C@H]4/C=C\CCCCC[C@H](NC(=O)c4ccns4)C(=O)N3C1)c1ccc(F)cc12]
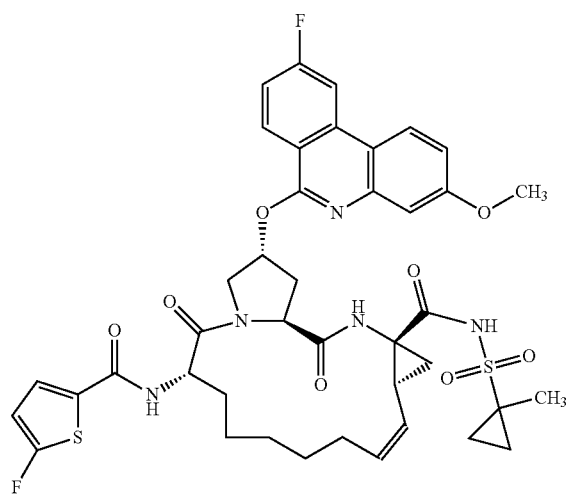 [SMILES: COc1ccc2c(c1)nc(O[C@@H]1C[C@H]3C(=O)N[C@]4(C(=O)NS(=O)(=O)C5(C)CC5)C[C@H]4/C=C\CCCCC[C@H](NC(=O)c4ccc(F)s4)C(=O)N3C1)c1ccc(F)cc12]
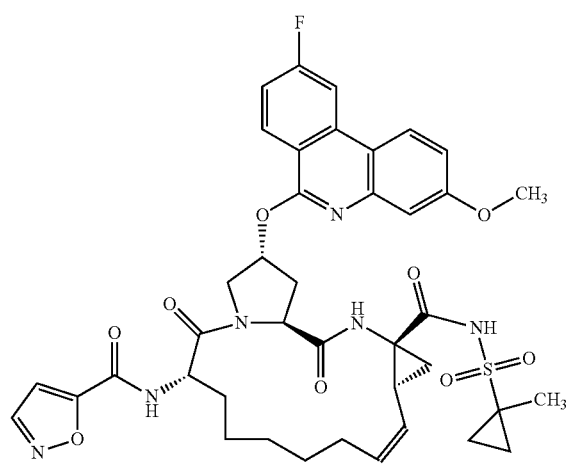 [SMILES: COc1ccc2c(c1)nc(O[C@@H]1C[C@H]3C(=O)N[C@]4(C(=O)NS(=O)(=O)C5(C)CC5)C[C@H]4/C=C\CCCCC[C@H](NC(=O)c4ccno4)C(=O)N3C1)c1ccc(F)cc12]

| Compound | nMI Assay |
|---|---|

-continued
| Compound | nMI Assay |
|---|---|
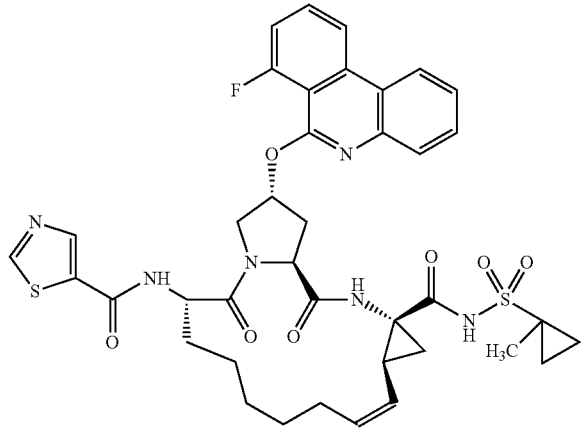 [SMILES: CC1(S(=O)(=O)NC(=O)[C@@]23C[C@H]2/C=C\CCCCC[C@H](NC(=O)c2cncs2)C(=O)N2C[C@H](Oc4nc5ccccc5c5cccc(F)c45)C[C@H]2C(=O)N3)CC1]
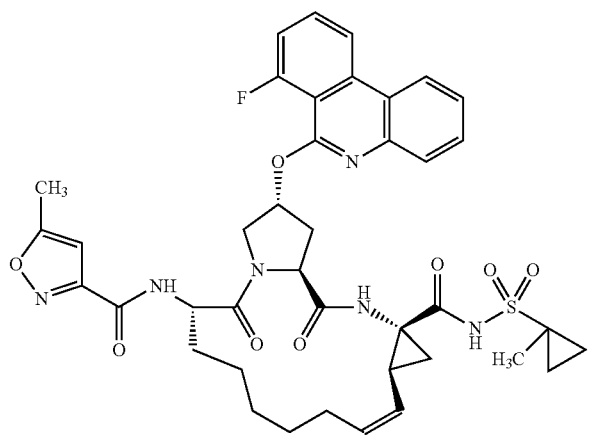 [SMILES: Cc1cc(C(=O)N[C@H]2CCCCC/C=C\[C@@H]3C[C@@]3(C(=O)NS(=O)(=O)C3(C)CC3)NC(=O)[C@@H]3C[C@@H](Oc4nc5ccccc5c5cccc(F)c45)CN3C2=O)no1]
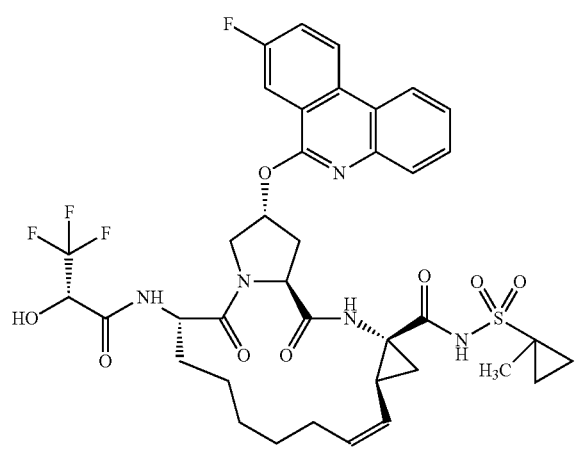 [SMILES: CC1(S(=O)(=O)NC(=O)[C@@]23C[C@H]2/C=C\CCCCC[C@H](NC(=O)[C@H](O)C(F)(F)F)C(=O)N2C[C@H](Oc4nc5ccccc5c5ccc(F)cc45)C[C@H]2C(=O)N3)CC1]

| Compound | nMI Assay |
|---|---|
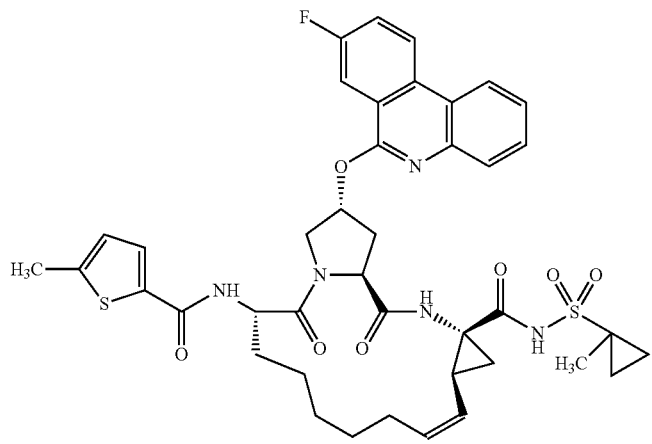 [SMILES: Cc1ccc(C(=O)N[C@H]2CCCCC/C=C\[C@@H]3C[C@@]3(C(=O)NS(=O)(=O)C3(C)CC3)NC(=O)[C@@H]3C[C@@H](Oc4nc5ccccc5c5ccc(F)cc45)CN3C2=O)s1]
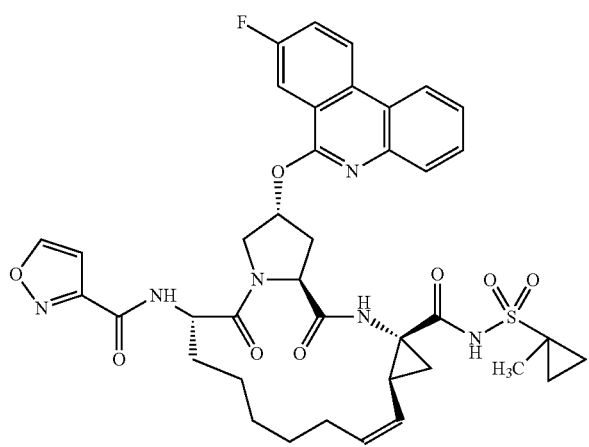 [SMILES: CC1(S(=O)(=O)NC(=O)[C@@]23C[C@H]2/C=C\CCCCC[C@H](NC(=O)c2ccon2)C(=O)N2C[C@H](Oc4nc5ccccc5c5ccc(F)cc45)C[C@H]2C(=O)N3)CC1]
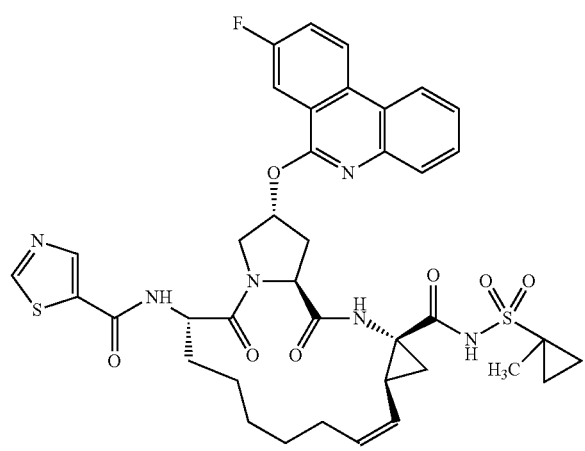 [SMILES: CC1(S(=O)(=O)NC(=O)[C@@]23C[C@H]2/C=C\CCCCC[C@H](NC(=O)c2cncs2)C(=O)N2C[C@H](Oc4nc5ccccc5c5ccc(F)cc45)C[C@H]2C(=O)N3)CC1]

-continued
| Compound | nMI Assay |
|---|---|
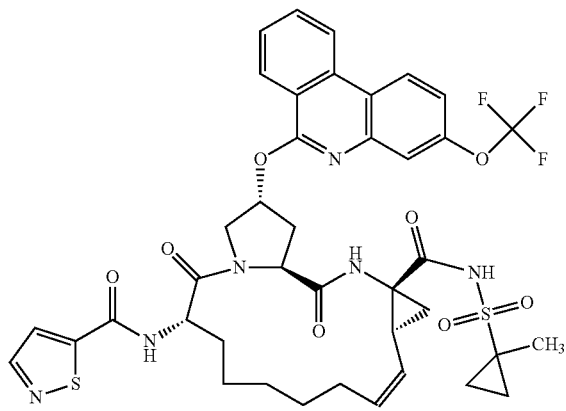 [SMILES: CC1(S(=O)(=O)NC(=O)[C@@]23C[C@H]2/C=C\CCCCC[C@H](NC(=O)c2ccns2)C(=O)N2C[C@H](Oc4nc5cc(OC(F)(F)F)ccc5c5ccccc45)C[C@H]2C(=O)N3)CC1]
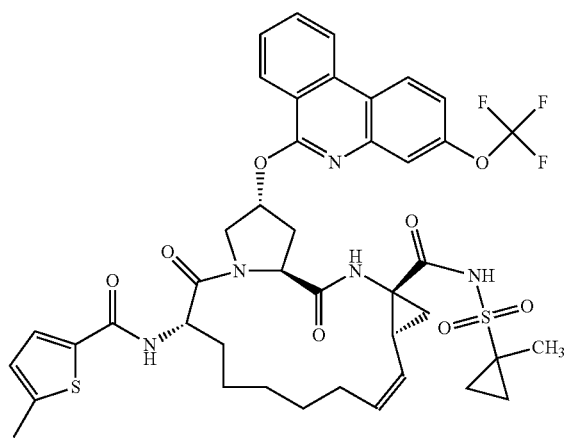 [SMILES: Cc1ccc(C(=O)N[C@H]2CCCCC/C=C\[C@@H]3C[C@@]3(C(=O)NS(=O)(=O)C3(C)CC3)NC(=O)[C@@H]3C[C@@H](Oc4nc5cc(OC(F)(F)F)ccc5c5ccccc45)CN3C2=O)s1]
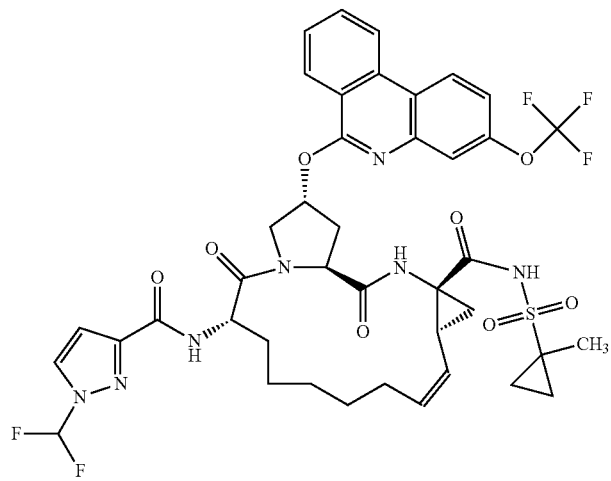 [SMILES: CC1(S(=O)(=O)NC(=O)[C@@]23C[C@H]2/C=C\CCCCC[C@H](NC(=O)c2ccn(C(F)F)n2)C(=O)N2C[C@H](Oc4nc5cc(OC(F)(F)F)ccc5c5ccccc45)C[C@H]2C(=O)N3)CC1]

| Compound | nMI Assay |
|----------|-----------|

-continued
| Compound | nMI Assay |
|---|---|
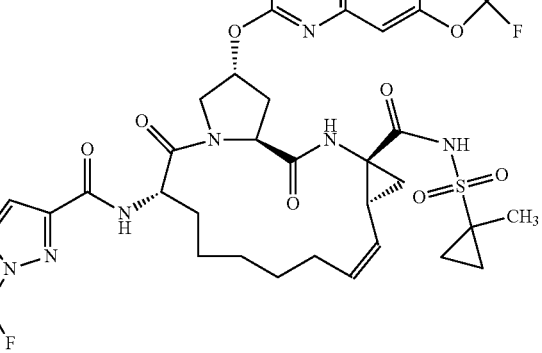
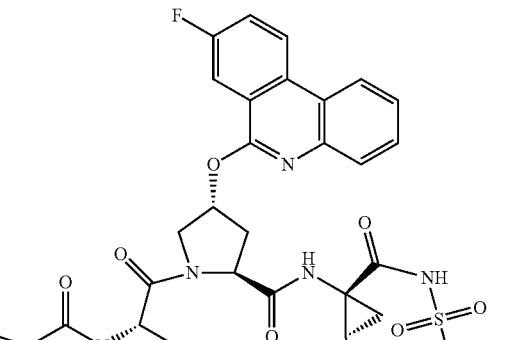
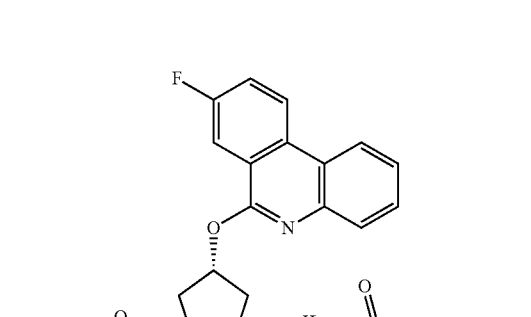

| Compound | nMI Assay |
|---|---|
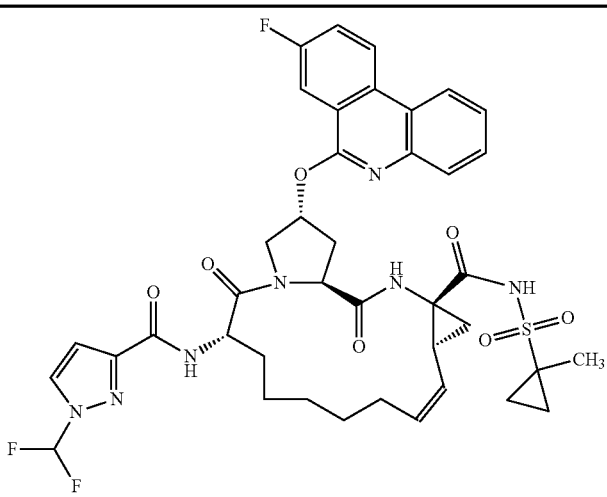
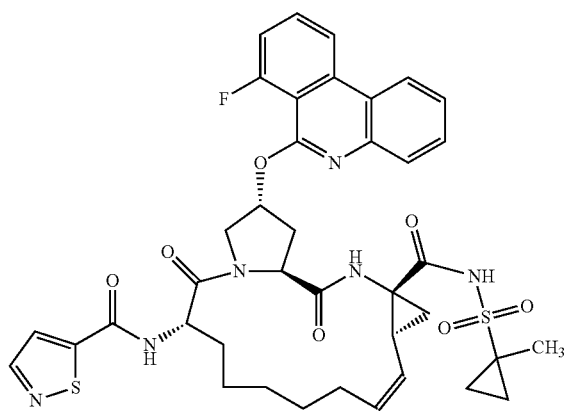 [SMILES: CC1(S(=O)(=O)NC(=O)[C@@]23C[C@H]2/C=C\CCCCC[C@H](NC(=O)c2ccns2)C(=O)N2C[C@H](Oc4nc5ccccc5c5cccc(F)c45)C[C@H]2C(=O)N3)CC1]
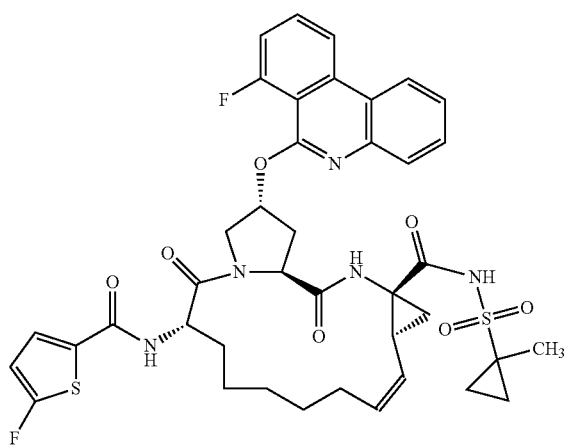 [SMILES: CC1(S(=O)(=O)NC(=O)[C@@]23C[C@H]2/C=C\CCCCC[C@H](NC(=O)c2ccc(F)s2)C(=O)N2C[C@H](Oc4nc5ccccc5c5cccc(F)c45)C[C@H]2C(=O)N3)CC1]

| Compound | nMI Assay |
|---|---|
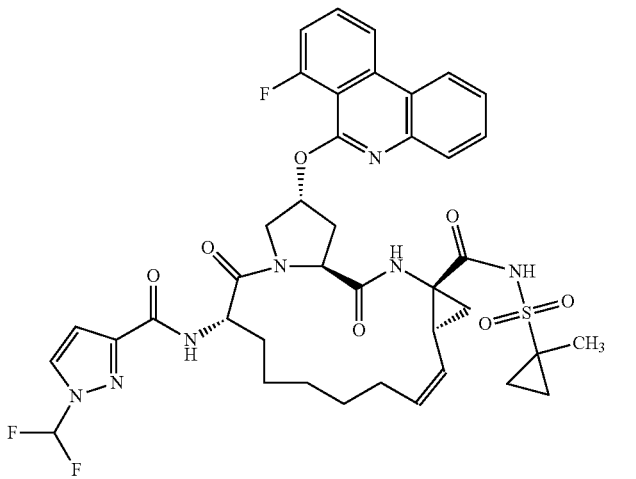 [SMILES: CC1(S(=O)(=O)NC(=O)[C@@]23C[C@H]2/C=C\CCCCC[C@H](NC(=O)c2ccn(C(F)F)n2)C(=O)N2C[C@H](Oc4nc5ccccc5c5cccc(F)c45)C[C@H]2C(=O)N3)CC1]
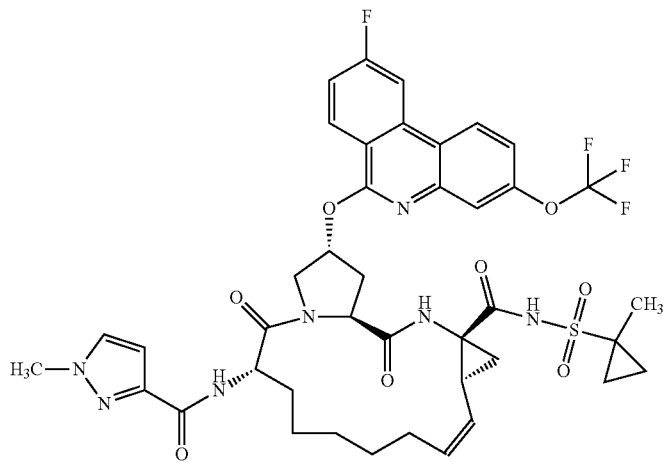 [SMILES: Cn1ccc(C(=O)N[C@H]2CCCCC/C=C\[C@@H]3C[C@@]3(C(=O)NS(=O)(=O)C3(C)CC3)NC(=O)[C@@H]3C[C@@H](Oc4nc5cc(OC(F)(F)F)ccc5c5cc(F)ccc45)CN3C2=O)n1]
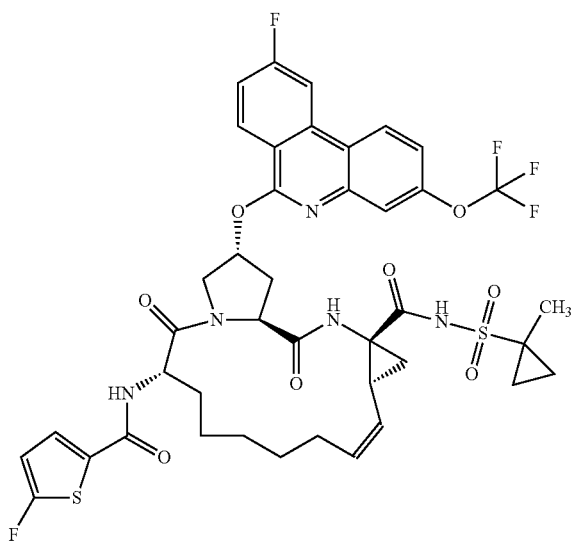 [SMILES: CC1(S(=O)(=O)NC(=O)[C@@]23C[C@H]2/C=C\CCCCC[C@H](NC(=O)c2ccc(F)s2)C(=O)N2C[C@H](Oc4nc5cc(OC(F)(F)F)ccc5c5cc(F)ccc45)C[C@H]2C(=O)N3)CC1]

| Compound | nMI Assay |
|---|---|

| Compound | nMI Assay |
|---|---|
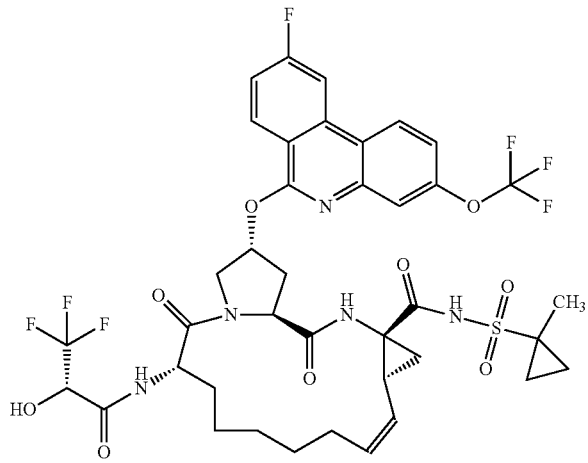 [SMILES: CC1(S(=O)(=O)NC(=O)[C@@]23C[C@H]2/C=C\CCCCC[C@H](NC(=O)[C@H](O)C(F)(F)F)C(=O)N2C[C@H](Oc4nc5cc(OC(F)(F)F)ccc5c5cc(F)ccc45)C[C@H]2C(=O)N3)CC1]
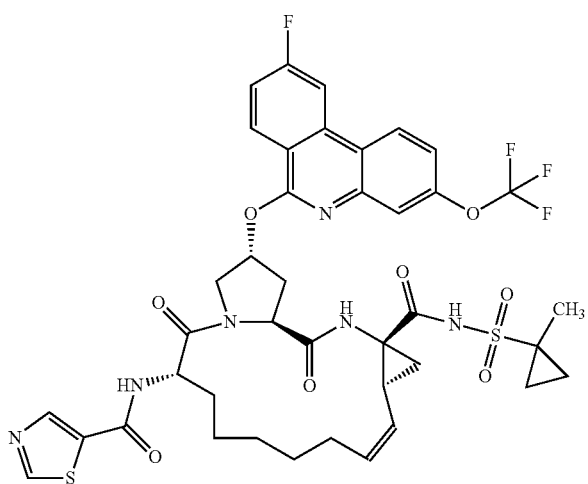 [SMILES: CC1(S(=O)(=O)NC(=O)[C@@]23C[C@H]2/C=C\CCCCC[C@H](NC(=O)c2cncs2)C(=O)N2C[C@H](Oc4nc5cc(OC(F)(F)F)ccc5c5cc(F)ccc45)C[C@H]2C(=O)N3)CC1]
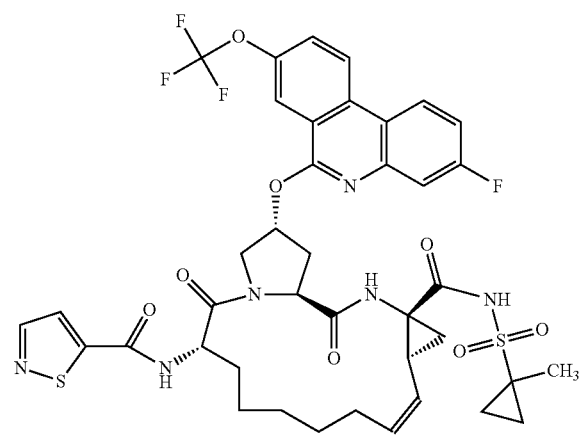 [SMILES: CC1(S(=O)(=O)NC(=O)[C@@]23C[C@H]2/C=C\CCCCC[C@H](NC(=O)c2ccns2)C(=O)N2C[C@H](Oc4nc5cc(F)ccc5c5ccc(OC(F)(F)F)cc45)C[C@H]2C(=O)N3)CC1]

| Compound | nMI Assay |
|---|---|

| Compound | nMI Assay |
|---|---|
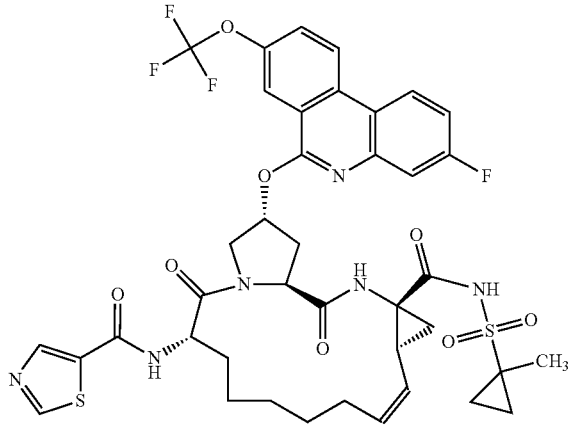 [SMILES: CC1(S(=O)(=O)NC(=O)[C@@]23C[C@H]2/C=C\CCCCC[C@H](NC(=O)c2cncs2)C(=O)N2C[C@H](Oc4nc5cc(F)ccc5c5ccc(OC(F)(F)F)cc45)C[C@H]2C(=O)N3)CC1]
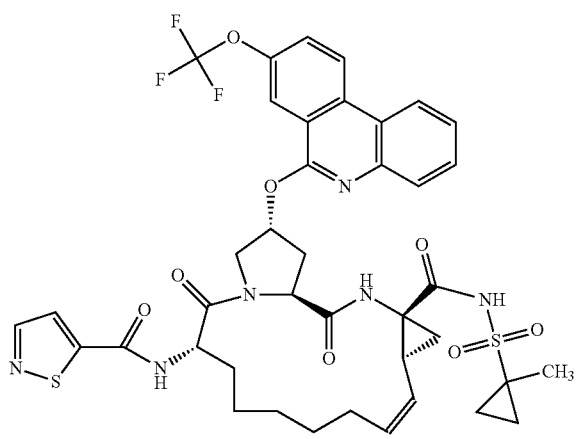 [SMILES: CC1(S(=O)(=O)NC(=O)[C@@]23C[C@H]2/C=C\CCCCC[C@H](NC(=O)c2ccns2)C(=O)N2C[C@H](Oc4nc5ccccc5c5ccc(OC(F)(F)F)cc45)C[C@H]2C(=O)N3)CC1]
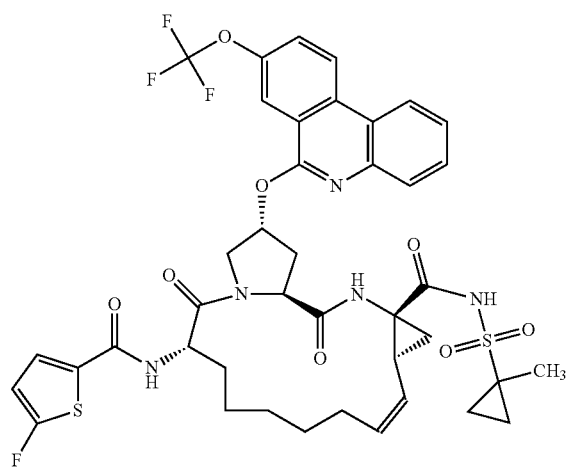 [SMILES: CC1(S(=O)(=O)NC(=O)[C@@]23C[C@H]2/C=C\CCCCC[C@H](NC(=O)c2ccc(F)s2)C(=O)N2C[C@H](Oc4nc5ccccc5c5ccc(OC(F)(F)F)cc45)C[C@H]2C(=O)N3)CC1]

| Compound | nMI Assay |
|---|---|
| +get,271 | 1a stable replicon (nM)<br>1b stable replicon (nM)<br>0.1-0.5 1a transient replicon (nM)<br>0.1-0.5 1b transient replicon (nM)<br>>1.0 3a transient replicon (nM) |
| +get,272 | 1a stable replicon (nM)<br>1b stable replicon (nM)<br>0.1-0.5 1a transient replicon (nM)<br>0.1-0.5 1b transient replicon (nM)<br>>1.0 3a transient replicon (nM) |

| Compound | nMI Assay |
|---|---|

Each compound's anti-HCV activity can be determined by measuring the activity of the luciferase reporter gene in the replicon in the presence of 5% FBS. The luciferase reporter gene, and selectable marker gene for replicons stably maintained in cell lines, is placed under the translational control of the poliovirus IRES instead of the HCV IRES, and HuH-7 cells are used to support the replication of the replicon.

The inhibitory activities of the compounds of the present invention can be evaluated using a variety of assays known in the art. For instance, stable subgenomic replicon cell lines can be used for compound characterization in cell culture, including those derived from genotypes 1a-H77, 1b-N and 1b-Con1, obtained from University of Texas Medical Branch, Galveston, Tex. (1a-H77 and 1b-N) or Apath, LLC, St. Louis, Mo. (1b-Con1). Chimeric replicons using the genotype 1a or 1b replicons with insertion of NS3 genes from isolates from humans infected with genotypes 1a or 1b can be used to measure inhitory activity against a panel of the target protein from natural isolates. Chimeric replicons using the genotype 1a or 1b replicons with insertion of NS3 genes from isolates from humans infected with genotypes 3a, 4 or 6 can be used to measure inhitory activity against representatives of those genotypes. The genotype 1a replicon construct contains the NS3-NS5B coding region derived from the H77 strain of HCV (1a-H77). The replicon also has a firefly luciferase reporter and a neomycin phosphotransferase (Neo) selectable marker. These two coding regions, separated by the FMDV 2a protease, comprise the first cistron of the bicistronic replicon construct, with the second cistron containing the NS3-NS5B coding region with addition of adaptive mutations E1202G, K1691R, K2040R and S2204I. The 1b-Con1 and 1b-N replicon constructs are identical to the 1a-H77 replicon, except that the HCV 5' UTR, 3' UTR, and NS3-NS5B coding region are derived from the 1b-Con1 or 1b-N strain, and the adaptive mutations are K1609E, K1846T and Y3005C for 1b-Con1 or A1098T, E1202G, and S2204I for 1b-N. In addition, the 1b-Con1 replicon construct contains a poliovirus IRES between the HCV IRES and the luciferase gene. Replicon cell lines can be maintained in Dulbecco's modified Eagles medium (DMEM) containing 10% (v/v) fetal bovine serum (FBS), 100 IU/ml penicillin, 100 mg/ml streptomycin (Invitrogen), and 200 mg/ml G418 (Invitrogen).

The inhibitory effects of the compounds of the invention on HCV replication can also be determined by measuring activity of the luciferase reporter gene encoded by subgenomic replicons not containing the Neo selectable marker, that are transiently expressed in cells. The adaptive mutations encoded by the 1a-H77, 1b-N and 1b-Con-1 replicons are the same as listed above. The 1b-Con1 replicon used for these transient assays contains the NS2-NS5B coding region rather than the NS3-5B coding region. These replicons may encode target NS3 genes as described for stable subgenomic replicons or they may encode amino acid variants that confer varying degrees of susceptibility to the drug. For example, variants could include R155K, D168E or D168V in a genotype 1a NS3 gene; R155K, A156T or D168V in a genotype 1b NS3 gene; S138T, A166T or Q168R in a genotype 3a NS3 gene. For example, cells can be transfected with the replicon by electroporation and seeded into 96 well plates at a density of 5000 cells per well in 100 µl DMEM containing 5% FBS. Compounds diluted in dimethyl sulfoxide (DMSO) to generate a 200× stock in a series of eight half-log dilutions can then be further diluted 100-fold in the medium containing 5% FBS and added to the cell culture plates already containing 100 µl of DMEM with 5% FBS. After an incubation period of either 3 or 4 days, 30 µl of Passive Lysis buffer (Promega) can be added to each well, with incubation for 15 minutes with rocking to lyse the cells. Luciferin solution (100 µl, Promega) can be added to each well, and luciferase activity can be measured with a luminometer. The percent inhibition of HCV RNA replication can be calculated for each compound concentration and the $EC_{50}$ value can be calculated using nonlinear regression curve fitting to the 4-parameter logistic equation and GraphPad Prism 4 software. Using the above-described assays or similar cell-based replicon assays, representative compounds of the present invention showed significantly inhibitory activities against HCV replication.

In another aspect, the invention provides a pharmaceutical composition comprising a therapeutically effective amount of a compound provided herein (e.g. formula D, or a pharmaceutically acceptable salt, ester, or prodrug thereof, in combination with a pharmaceutically acceptable carrier or excipient.

According to another embodiment, the pharmaceutical compositions of the present invention may further contain one or more other anti-HCV agents. Examples of anti-HCV agents include, but are not limited to, α-interferon; β-interferon; pegylated interferon-α; pegylated interferon-lambda; ribavirin; viramidine; R-5158; nitazoxanide; amantadine; Debio-025, NIM-811; HCV polymerase inhibitors such as R7128, R1626, R4048, T-1106, PSI-7851, PF-00868554, ANA-598, IDX184, IDX102, IDX375, GS-9190, VCH-759, VCH-916, MK-3281, BCX-4678, MK-3281, VBY708, ANA598, GL59728 or GL60667; BMS-790052; BMS-791325; BMS-650032; HCV entry, helicase or internal ribosome entry site inhibitors; or other HCV replication inhibitors such as GS-9132, ACH-1095, AP-H005, A-831, A-689, AZD2836. For further details see S. Tan, A. Pause, Y. Shi, N. Sonenberg, Hepatitis C Therapeutics: Current Status and Emerging Strategies, *Nature Rev. Drug Discov.*, 1, 867-881 (2002); WO 00/59929 (2000); WO 99/07733 (1999); WO 00/09543 (2000); WO 99/50230 (1999); U.S. Pat. No. 5,861,297 (1999); and US2002/0037998 (2002).

According to an additional embodiment, the pharmaceutical compositions of the present invention may further contain another HCV protease inhibitor, such as telaprevir, boceprevir, ITMN-191, BI-201335, TMC-435, MK-7009, VBY-376, VX-500, VX-813, PHX-B, ACH-1625, IDX136, or IDX316.

In other embodiments, the invention provides a pharmaceutical composition further comprising pegylated interferon, another anti-viral, anti-bacterial, anti-fungal or anti-cancer agent, or an immune modulator, and/or further comprising a cytochrome P450 monooxygenase inhibitor or a pharmaceutically acceptable salt thereof. In certain embodiments, the cytochrome P450 monooxygenase inhibitor is ritonavir.

In another aspect, the invention provides for the use of a compound of the invention to manufacture an agent for preventing or treating viral infection. In another aspect, the invention provides for the use of a compound of the invention to manufacture an agent for preventing or treating hepatitis C infection. The present invention also contemplates the use of a solvate (e.g., hydrate) of a compound of the invention to manufacture pharmaceutical compositions for preventing or treating hepatitis C infection. As used herein, "solvate" refers to the physical association of a compound of the invention with one or more solvent molecule, whether organic or inorganic. This physical association often includes hydrogen bonding. In certain instances, the solvate is capable of isolation, for example, when one or more solvate molecules are incorporated in the crystal lattice of the crystalline solid.

In another embodiment, the compounds or pharmaceutical compositions of the invention are administered with ritonavir, either simultaneously or sequentially. In certain embodiments, a compound or a pharmaceutical composition of the invention is administered in the same composition as ritonavir. In another embodiment, a compound or a pharmaceutical composition thereof of the invention is administered in a different composition than ritonavir.

According to yet another embodiment, the pharmaceutical compositions of the present invention may further comprise inhibitor(s) of other targets in the HCV life cycle, including, but not limited to, helicase, polymerase, metalloprotease, CD81, NS5A, cyclophilin, and internal ribosome entry site (IRES).

In one aspect, the invention provides a method of treating a viral infection in a subject, comprising administering to the subject a therapeutically effective amount of a compound of the invention described herein (e.g. formula I), or a pharmaceutically acceptable salt, ester or prodrug thereof, or a pharmaceutical composition comprising the same.

According to a further embodiment, the present invention includes methods of treating hepatitis C infections in a subject in need of such treatment by administering to said subject an anti-HCV virally effective amount or an inhibitory amount of the compounds or pharmaceutical compositions of the present invention.

According to another embodiment, the present invention includes methods of treating hepatitis C infections in a subject in need of such treatment by administering to said subject a compound or a pharmaceutical composition of the present invention. The methods can further include administration of an additional therapeutic agent, including another antiviral agent or an anti-HCV agent as described hereinabove. The additional agent can be co-administered (such as concurrently administered or sequentially administered) with a compound (a pharmaceutically acceptable salt, ester or prodrug thereof) or a pharmaceutical composition of the present invention. The additional agent(s) and a compound (or a pharmaceutically acceptable salt, ester or prodrug thereof) of the present invention can be formulated in the same composition, or in different compositions but co-administered concurrently or sequentially. The methods herein can further include the step of identifying that the subject is in need of treatment for hepatitis C infection. The identification can be by subjective (e.g., health care provider determination) or objective (e.g., diagnostic test) means.

In one aspect, the invention provides a method of inhibiting the replication of hepatitis C virus, the method comprising contacting a hepatitis C virus with an effective amount of a compound or pharmaceutical composition of the invention.

In another embodiment, the invention provides a method as described above, further comprising administering an additional anti-hepatitis C virus agent. Examples of anti-hepatitis C virus agents include, but are not limited to, α-interferon; β-interferon; pegylated interferon-α; pegylated interferon-lambda; ribavirin; viramidine; R-5158; nitazoxanide; amantadine; Debio-025, NIM-811; HCV polymerase inhibitors such as R7128, R1626, R4048, T-1106, PSI-7851, PF-00868554, ANA-598, IDX184, IDX102, IDX375, GS-9190, VCH-759, VCH-916, MK-3281, BCX-4678, MK-3281, VBY708, ANA598, GL59728 or GL60667; BMS-790052; BMS-791325; BMS-650032; HCV entry, helicase or internal ribosome entry site inhibitors; or other HCV replication inhibitors such as GS-9132, ACH-1095, AP-H005, A-831, A-689, AZD2836. For further details see S. Tan, A. Pause, Y. Shi, N. Sonenberg, Hepatitis C Therapeutics: Current Status and Emerging Strategies, *Nature Rev. Drug Discov.*, 1, 867-881 (2002); WO 00/59929 (2000); WO 99/07733 (1999); WO 00/09543 (2000); WO 99/50230 (1999); U.S. Pat. No. 5,861,297 (1999); and US2002/0037998 (2002). Preferably, a compound or a pharmaceutical composition of the present invention is co-administered with, or used in combination with, pegylated interferon (e.g., pegylated interferon alpha-2a or 2b) and ribavirin. Ritonavir or another cytochrome P450 monooxygenase inhibitor can also be used to enhance the pharmacokinetics of the compound of the present invention. The patient being treated is preferably infected with HCV genotype-1 (e.g., genotype 1a or 1b). Patients infected with other HCV genotypes, such as genotypes 2, 3, 4, 5 or 6, can also be treated with a compound or a pharmaceutical composition of the present invention.

In another embodiment, the invention provides a method as described above, further comprising administering another HCV protease inhibitor, an HCV polymerase inhibitor, an HCV helicase inhibitor, or an internal ribosome entry site (IRES) inhibitor, such as telaprevir, boceprevir, ITMN-191, BI-201335, TMC-435, MK-7009, VBY-376, VX-500, VX-813, PHX-B, ACH-1625, IDX136, IDX316, pegylated interferon, another anti-viral, anti-bacterial, anti-fungal or anti-cancer agent, or an immune modulator, and/or further comprising a cytochrome P450 monooxygenase inhibitor or a pharmaceutically acceptable salt thereof. In certain embodiments, the cytochrome P450 monooxygenase inhibitor is ritonavir.

An additional embodiment of the present invention includes methods of treating biological samples by contacting the biological samples with the compounds of the present invention.

Yet another aspect of the present invention is a process of making any of the compounds delineated herein employing any of the synthetic means delineated herein.

Definitions

Listed below are definitions of various terms used to describe this invention. These definitions apply to the terms as they are used throughout this specification and claims, unless otherwise limited in specific instances, either individually or as part of a larger group. The number of carbon atoms in a hydrocarbyl substituent can be indicated by the prefix "$C_x$-$C_y$," where x is the minimum and y is the maximum number of carbon atoms in the substituent.

The prefix "halo" indicates that the substituent to which the prefix is attached is substituted with one or more independently selected halogen radicals. For example, "haloalkyl" means an alkyl substituent wherein at least one hydrogen radical is replaced with a halogen radical.

If a linking element in a depicted structure is "absent", then the left element in the depicted structure is directly linked to the right element in the depicted structure. For example, if a chemical structure is depicted as X-L-Y wherein L is absent, then the chemical structure is X-Y.

The term "alkyl" as used herein, refers to a saturated, straight- or branched-chain hydrocarbon radical typically containing from 1 to 20 carbon atoms. For example, "$C_1$-$C_8$ alkyl" contains from one to eight carbon atoms. Examples of alkyl radicals include, but are not limited to, methyl, ethyl, propyl, isopropyl, n-butyl, tert-butyl, neopentyl, n-hexyl, heptyl, octyl radicals and the like.

The term "alkenyl" as used herein, denotes a straight- or branched-chain hydrocarbon radical containing one or more double bonds and typically from 2 to 20 carbon atoms. For example, "$C_2$-$C_8$ alkenyl" contains from two to eight carbon atoms. Alkenyl groups include, but are not limited to, for example, ethenyl, propenyl, butenyl, 1-methyl-2-buten-1-yl, heptenyl, octenyl and the like.

The term "alkynyl" as used herein, denotes a straight- or branched-chain hydrocarbon radical containing one or more triple bonds and typically from 2 to 20 carbon atoms. For example, "$C_2$-$C_8$ alkynyl" contains from two to eight carbon atoms. Representative alkynyl groups include, but are not limited to, for example, ethynyl, 1-propynyl, 1-butynyl, heptynyl, octynyl and the like.

The term "alkylene" refers to a divalent group derived from a straight or branched saturated hydrocarbyl chain typically containing from 1 to 20 carbon atoms, more typically from 1 to 8 carbon atoms. Representative examples of alkylene include, but are not limited to, —$CH_2$—, —$CH_2CH_2$—, —$CH_2CH_2CH_2$—, —$CH_2CH_2CH_2CH_2$—, and —$CH_2CH(CH_3)CH_2$—.

The term "alkenylene" refers to a divalent unsaturated hydrocarbyl group which may be linear or branched and which has at least one carbon-carbon double bond. An alkenylene group typically contains 2 to 20 carbon atoms, more typically from 2 to 8 carbon atoms. Non-limiting examples of alkenylene groups include —C(H)=C(H)—, —C(H)=C(H)—$CH_2$—, —C(H)=C(H)—$CH_2$—$CH_2$—, —$CH_2$—C(H)=C(H)—$CH_2$—, —C(H)=C(H)—CH($CH_3$)—, and —$CH_2$—C(H)=C(H)—CH($CH_2CH_3$)—.

The term "alkynylene" refers to a divalent unsaturated hydrocarbon group which may be linear or branched and which has at least one carbon-carbon triple bond. Representative alkynylene groups include, by way of example, —C≡C—, —C≡C—$CH_2$—, —C≡$CH_2$—$CH_2$—, —$CH_2$—C≡C—$CH_2$—, —C≡C—CH($CH_3$)—, and —$CH_2$—C≡C—CH($CH_2CH_3$)—.

The terms "cycloalkyl," "carbocycle," "carbocyclic" or "carbocyclyl" refer to a) a monovalent group derived from a monocyclic or polycyclic saturated carbocyclic ring compound; or b) a saturated, partially saturated or completely unsaturated ring system containing zero heteroatom ring atom and typically from 3 to 18 carbon ring atoms. A carbocyclyl may be, without limitation, a single ring, or two or more fused rings, or bridged or Spiro rings. A carbocyclyl may contain, for example, from 3 to 14 ring members, from 3 to 10 ring members, from 3 to 8 ring members, or from 3 to 6 ring members. A substituted carbocyclyl may have either cis or trans geometry. Representative examples of carbocyclyl groups include, but are not limited to, cyclopropyl, cyclobutyl, cyclopentyl, cyclohexyl, bicyclo[2.2.1]heptyl, bicyclo[2.2.2]octyl cyclopropyl, cycloheptyl, cyclooctyl, cyclopentenyl, cyclopentadienyl, cyclohexadienyl, adamantyl, decahydro-naphthalenyl, octahydro-indenyl, cyclohexenyl, phenyl, naphthyl, fluorenyl, indanyl, 1,2,3,4-tetrahydronaphthyl, indenyl, isoindenyl, bicyclodecanyl, anthracenyl, phenanthrene, benzonaphthenyl (also known as "phenalenyl"), decalinyl, and norpinanyl and the like. A carbocyclyl group can be attached to the parent molecular moiety through any substitutable carbon atom of the group.

The term "aryl" refers to an aromatic carbocyclyl containing from 6 to 14 carbon ring atoms. Non-limiting examples of aryls include phenyl, naphthalenyl, anthracenyl, and indenyl and the like. An aryl group can be connected to the parent molecular moiety through any substitutable carbon atom of the group.

The term "aralkyl" or "arylalkyl" refers to an alkyl residue attached to an aryl ring. Examples of aralkyl include, but are not limited to, benzyl, phenethyl and the like.

The term "heteroaryl" means an aromatic heterocyclyl typically containing from 5 to 18 ring atoms. A heteroaryl may be a single ring, or two or more fused rings. Non-limiting examples of five-membered heteroaryls include imidazolyl; furanyl; thiophenyl (or thienyl or thiofuranyl); pyrazolyl; oxazolyl; isoxazolyl; thiazolyl; 1,2,3-, 1,2,4-, 1,2,5-, and 1,3,4-oxadiazolyl; and isothiazolyl. Non-limiting examples of six-membered heteroaryls include pyridinyl; pyrazinyl; pyrimidinyl; pyridazinyl; and 1,3,5-, 1,2,4-, and 1,2,3-triazinyl. Non-limiting examples of 6/5-membered fused ring heteroaryls include benzothiofuranyl, isobenzothiofuranyl, benzisoxazolyl, benzoxazolyl, purinyl, and anthranilyl. Non-limiting examples of 6/6-membered fused ring heteroaryls include quinolinyl; isoquinolinyl; and benzoxazinyl (including cinnolinyl and quinazolinyl).

The term "heteroaralkyl" or "heteroarylalkyl" refers to an alkyl residue attached to a heteroaryl ring. Examples include, but are not limited to, pyridinylmethyl, pyrimidinylethyl and the like.

The term "heterocycloalkyl" refers to a non-aromatic 3-, 4-, 5-, 6- or 7-membered ring or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, and (iv) any of the above rings may be fused to a benzene ring.

Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl and the like.

The terms "heterocyclic" or "heterocyclo" or "heterocyclyl" refer to a saturated (e.g., "heterocycloalkyl"), partially unsaturated (e.g., "heterocycloalkenyl" or "heterocycloalkynyl") or completely unsaturated (e.g., "heteroaryl") ring system typically containing from 3 to 18 ring atoms, where at least one of the ring atoms is a heteroatom (i.e., nitrogen, oxygen or sulfur), with the remaining ring atoms being independently selected from the group consisting of carbon, nitrogen, oxygen and sulfur. A heterocyclyl group can be linked to the parent molecular moiety via any substitutable carbon or nitrogen atom in the group, provided that a stable molecule results. A heterocyclyl may be, without limitation, a single ring, which typically contains from 3 to 14 ring atoms, from 3 to 8 ring atoms, from 3 to 6 ring atoms, or from 5 to 6 ring atoms. Non-limiting examples of single-ring heterocyclyls include furanyl, dihydrofuranyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiodiazolyl, oxathiazolyl, oxadiazoly, pyranyl, dihydropyranyl, pyridinyl, piperidinyl, pyridazinyl, pyrimidinyl, pyrazinyl, piperazinyl, triazinyl, isoxazinyl, oxazolidinyl, isoxazolidinyl, oxathiazinyl, oxadiazinyl, morpholinyl, azepinyl, oxepinyl, thiepinyl, or diazepinyl. A heterocyclyl may also include, without limitation, two or more rings fused together, such as, for example, naphthyridinyl, thiazolpyrimidinyl, thienopyrimidinyl, pyrimidopyrimidinyl, or pyridopyrimidinyl. A heterocyclyl may comprise one or more sulfur atoms as ring members; and in some cases, the sulfur atom(s) is oxidized to SO or $SO_2$. The nitrogen heteroatom(s) in a heterocyclyl may or may not be quaternized, and may or may not be oxidized to N-oxide. In addition, the nitrogen heteroatom(s) may or may not be N-protected.

The terms "optionally substituted", "optionally substituted alkyl," "optionally substituted alkenyl," "optionally substituted alkynyl", "optionally substituted carbocyclic," "optionally substituted aryl", "optionally substituted heteroaryl," "optionally substituted heterocyclic," and any other optionally substituted group as used herein, refer to groups that are substituted or unsubstituted by independent replacement of one, two, or three or more of the hydrogen atoms thereon with substituents including, but not limited to:

—F, —Cl, —Br, —I,

—OH, protected hydroxy, alkoxy, oxo, thiooxo,

—$NO_2$, —CN, $CF_3$, $N_3$,

—$NH_2$, protected amino, —NH alkyl, —NH alkenyl, —NH alkynyl, —NH cycloalkyl, —NH-aryl, —NH-heteroaryl, —NH-heterocyclic, -dialkylamino, -diarylamino, -diheteroarylamino, —O-alkyl, —O-alkenyl, —O-alkynyl, —O-cycloalkyl, —O-aryl, —O-heteroaryl, —O-heterocyclic, —C(O)-alkyl, —C(O)-alkenyl, —C(O)-alkynyl, —C(O)-cycloalkyl, —C(O)-aryl, —C(O)-heteroaryl, —C(O)-heterocycloalkyl, —$CONH_2$, —CONH-alkyl, —CONH-alkenyl, —CONH-alkynyl, —CONH-cycloalkyl, —CONH-aryl, —CONH-heteroaryl, —CONH-heterocycloalkyl, —$OCO_2$-alkyl, —$OCO_2$-alkenyl, —$OCO_2$-alkynyl, —$OCO_2$-cycloalkyl, —$OCO_2$-aryl, —$OCO_2$-heteroaryl, —$OCO_2$-heterocycloalkyl, —$OCONH_2$, —OCONH-alkyl, —OCONH-alkenyl, —OCONH-alkynyl, —OCONH-cycloalkyl, —OCONH-aryl, —OCONH-heteroaryl, —OCONH-heterocycloalkyl, —NHC(O)-alkyl, —NHC(O)-alkenyl, —NHC(O)-alkynyl, —NHC(O)-cycloalkyl, —NHC(O)-aryl, —NHC(O)-heteroaryl, —NHC(O)-heterocycloalkyl, —$NHCO_2$-alkyl, —$NHCO_2$-alkenyl, —$NHCO_2$-alkynyl, —$NHCO_2$-cycloalkyl, —$NHCO_2$-aryl, —$NHCO_2$-heteroaryl, —$NHCO_2$-heterocycloalkyl, —$NHC(O)NH_2$, —NHC(O)NH-alkyl, —NHC(O)NH-alkenyl, —NHC(O)NH-alkenyl, —NHC(O)NH-cycloalkyl, —NHC(O)NH-aryl, —NHC(O)NH-heteroaryl, —NHC(O)NH-heterocycloalkyl, $NHC(S)NH_2$, —NHC(S)NH-alkyl, —NHC(S)NH-alkenyl, —NHC(S)NH-alkynyl, —NHC(S)NH-cycloalkyl, —NHC(S)NH-aryl, —NHC(S)NH-heteroaryl, —NHC(S)NH-heterocycloalkyl, —$NHC(NH)NH_2$, —NHC(NH)NH-alkyl, —NHC(NH)NH--alkenyl, —NHC(NH)NH-alkenyl, —NHC(NH)NH-cycloalkyl, —NHC(NH)NH-aryl, —NHC(NH)NH-heteroaryl, —NHC(NH)NH-heterocycloalkyl, —NHC(NH)-alkyl, —NHC(NH)-alkenyl, —NHC(NH)-alkenyl, —NHC(NH)-cycloalkyl, —NHC(NH)-aryl, —NHC(NH)-heteroaryl, —NHC(NH)-heterocycloalkyl, —C(NH)NH-alkyl, —C(NH)NH-alkenyl, —C(NH)NH-alkynyl, —C(NH)NH-cycloalkyl, —C(NH)NH-aryl, —C(NH)NH-heteroaryl, —C(NH)NH-heterocycloalkyl, S(O)-alkyl, —S(O)-alkenyl, —S(O)-alkynyl, —S(O)-cycloalkyl, —S(O)-aryl, —S(O)-heteroaryl, —S(O)-heterocycloalkyl —$SO_2NH_2$, —$SO_2$NH-alkyl, —$SO_2$NH-alkenyl, —$SO_2$NH-alkynyl, —$SO_2$NH-cycloalkyl, —$SO_2$NH-aryl, —$SO_2$NH-heteroaryl, —$SO_2$NH-heterocycloalkyl, —$NHSO_2$-alkyl, —$NHSO_2$-alkenyl, —$NHSO_2$-alkynyl, —$NHSO_2$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -alkyl, -alkenyl, -alkynyl, -aryl, -arylalkyl, -heteroaryl, -heteroarylalkyl, -heterocycloalkyl, -cycloalkyl, -carbocyclic, -heterocyclic, polyalkoxyalkyl, polyalkoxy, -methoxymethoxy, -methoxyethoxy, —SH, —S-alkyl, —S-alkenyl, —S-alkynyl, —S-cycloalkyl, —S-aryl, —S-heteroaryl, —S-heterocycloalkyl, or methylthiomethyl.

It is understood that the aryls, heteroaryls, carbocyclics, heterocyclics, alkyls, and the like can be further substituted.

The terms "halo" and "halogen," as used herein, refer to an atom selected from fluorine, chlorine, bromine and iodine.

The term "subject" as used herein refers to a mammal. A subject therefore refers to, for example, dogs, cats, horses, cows, pigs, guinea pigs, and the like. Preferably the subject is a human. When the subject is a human, the subject may be either a patient or a healthy human.

The term "hydroxy activating group", as used herein, refers to a labile chemical moiety which is known in the art to activate a hydroxy group so that it will depart during synthetic procedures such as in a substitution or elimination reactions. Examples of hydroxy activating group include, but not limited to, mesylate, tosylate, triflate, p-nitrobenzoate, phosphonate and the like.

The term "leaving group," or "LG", as used herein, refers to any group that leaves in the course of a chemical reaction involving the group and includes but is not limited to halogen, brosylate, mesylate, tosylate, triflate, p-nitrobenzoate, phosphonate groups, for example.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy protecting group," as used herein, refers to a labile chemical moiety which is known in the art to protect a hydroxy group against undesired reactions during synthetic procedures. After said synthetic procedure(s) the hydroxy protecting group as described herein may be selectively removed. Hydroxy protecting groups as known in the are described generally in T. H. Greene and P. G. M. Wuts, Protective Groups in Organic Synthesis, 3rd edition, John Wiley & Sons, New York (1999). Examples of hydroxy protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl(trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxy protecting groups for the present invention are acetyl (Ac or —C(O)CH$_3$), benzoyl (Bz or —C(O)C$_6$H$_5$), and trimethylsilyl (TMS or —Si(CH$_3$)$_3$).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, Protective Groups in Organic Synthesis, 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "protected amino," as used herein, refers to an amino group protected with an amino protecting group as defined above.

The term "alkylamino" refers to a group having the structure —N(R$_a$R$_b$), where R$_a$ and R$_b$ are independent H or alkyl.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates. Examples of aliphatic carbonyls include, but are not limited to, acetyl, propionyl, 2-fluoroacetyl, butyryl, 2-hydroxy acetyl, and the like.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts, or salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, or magnesium salts, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to afford any compound delineated by the formulae of the instant invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development", Chapter 5, 113-191 (1991); Bundgaard, et al., Journal of Drug Deliver Reviews, 8:1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

This invention also encompasses pharmaceutical compositions containing, and methods of treating viral infections through administering, pharmaceutically acceptable prodrugs of compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxyysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxy carbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups, and elixirs. In addition to the active compounds, the liquid dosage forms may contain inert diluents commonly used in the art such as, for example, water, alcohol or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, polysorbate, dimethylformamide, oils (in particular, cottonseed, groundnut, corn, germ, olive, castor, and sesame oils), mono- or di-glycerides, glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, antioxidants, sweetening, flavoring, and perfuming agents. The liquid dosage form can also be encapsulated in a gelatin capsule, wherein a compound of the present invention can be dissolved in a pharmaceutically acceptable carrier containing, for example, one or more solubilizating agents (e.g., polysorbate 80 and mono and diglycerides), and other suitable excipients (e.g., an antioxidants such as ascorbyl palmitate, or a sweetening or flavoring agent).

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Immediate release forms are also contemplated by the present invention.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, viral infections are treated or prevented in a subject, such as a human or another animal, by administering to the subject a therapeutically effective amount of a compound of the invention (or a pharmaceutically acceptable salt, ester or prodrug thereof), in such amounts and for such time as is necessary to achieve the desired result. The term "therapeutically effective amount" of a compound of the invention, as used herein, means a sufficient amount of the compound so as to decrease the viral load in a subject and/or decrease the subject's HCV symptoms. As is well understood in the medical arts a therapeutically effective amount of a compound of this invention will be at a reasonable benefit/risk ratio applicable to any medical treatment.

Antiviral Activity

An inhibitory amount or dose of the compounds of the present invention may range from about 0.1 mg/Kg to about 500 mg/Kg, alternatively from about 1 to about 50 mg/Kg. Inhibitory amounts or doses will also vary depending on route of administration, as well as the possibility of co-usage with other agents.

According to the methods of treatment of the present invention, viral infections are treated or prevented in a subject such as a human or lower mammal by administering to the subject an anti-hepatitis C virally effective amount or an inhibitory amount of a compound of the present invention, in such amounts and for such time as is necessary to achieve the desired result. An additional method of the present invention is the treatment of biological samples with an inhibitory amount of a compound of composition of the present invention in such amounts and for such time as is necessary to achieve the desired result.

The term "anti-hepatitis C virally effective amount" of a compound of the invention, as used herein, means a sufficient amount of the compound so as to decrease the viral load in a biological sample or in a subject. As well understood in the medical arts, an anti-hepatitis C virally effective amount of a compound of this invention will be at a reasonable benefit/risk ratio applicable to any medical treatment.

The term "inhibitory amount" of a compound of the present invention means a sufficient amount to decrease the hepatitis C viral load in a biological sample or a subject. It is understood that when said inhibitory amount of a compound of the present invention is administered to a subject it will be at a reasonable benefit/risk ratio applicable to any medical treatment as determined by a physician. The term "biological sample(s)," as used herein, means a substance of biological origin intended for administration to a subject. Examples of biological samples include, but are not limited to, blood and components thereof such as plasma, platelets, subpopulations of blood cells and the like; organs such as kidney, liver, heart, lung, and the like; sperm and ova; bone marrow and components thereof; or stem cells. Thus, another embodiment of the present invention is a method of treating a biological sample by contacting said biological sample with an inhibitory amount of a compound or pharmaceutical composition of the present invention.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily inhibitory dose of the compounds of this invention administered to a subject in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In one embodiment, treatment regimens according to the present invention comprise administration to a patient in need of such treatment from about 10 mg to about 1000 mg of the compound(s) of this invention per day in single or multiple doses. In another embodiment, the treatment regimen comprises administration to a patient in need of such treatment from about 25 mg to about 6000 mg of a compound(s) of this invention per day in single or multiple doses, either with or without a cytochrome P450 monooxygenase inhibitor such as ritonavir. The suitable daily dose for the co-administered cytochrome P450 monooxygenase inhibitor (e.g., ritonavir) can range, without limitation, from 10 to 200 mg. Preferably, a compound(s) of the present invention, or a combination of a compound(s) of the invention and ritonavir, is administered once daily or twice daily to achieve the desired daily dose amount. For instance, when used without ritonavir, a compound of the present invention can be administered to a patient twice a day with a total daily dose of 4000, 4200, 4400, 4600, 4800 or 5000 mg. For another instance, when used in combination with ritonavir, a compound of the present invention can be administered to a patient once or twice a day with a total daily dose of 200, 400, 600 or 800 mg, where the amount of ritonavir can be 25, 50 or 100 mg per administration.

Synthetic Methods

The compounds and processes of the present invention will be better understood in connection with the following synthetic schemes that illustrate the methods by which the compounds of the invention may be prepared.

Definitions of variables in the structures in the schemes herein are commensurate with those of corresponding positions in the formulae delineated herein.

A method of producing a compound of formula I, or a pharmaceutically acceptable salt, ester or prodrug thereof, comprising the step of reacting a compound of formula X:

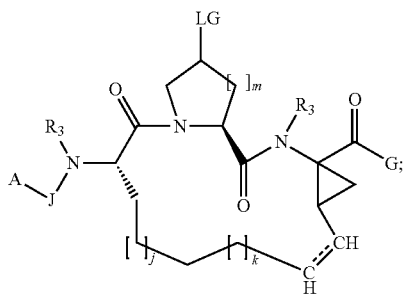

(X)

wherein,

J is absent, optionally substituted alkylene, optionally substituted alkenylene, optionally substituted alkynylene, —C(O)—, —O—C(O)—, —N(R$_3$)—C(O)—, —C(S)—, —C(=NR$_4$)—, —S(O)—, —S(O$_2$)—, or —N(R$_3$)—;

A is optionally substituted alkyl, optionally substituted alkenyl, or optionally substituted alkynyl, each containing 0, 1, 2, or 3 heteroatoms selected from O, S, or N; optionally substituted aryl, optionally substituted arylalkyl, optionally substituted alkoxy, optionally substituted heteroaryl, optionally substituted heterocyclic, or optionally substituted carbocyclic;

G is -E-R$_5$;

wherein E is absent; optionally substituted alkylene, optionally substituted alkenylene, optionally substituted alkynylene, each containing 0, 1, 2, or 3 heteroatoms selected from O, S, or N; or —O—, —S—, —N(R$_3$)—, —N(R$_3$)S(O$_P$)—, —N(R$_3$)C(O)—, —N(R$_3$)C(O)S(O$_P$)—, —OS(O$_p$)—, —C(O)S(O$_p$)—, or —C(O)N(R$_3$)S(O$_p$)—;

each p is independently 0, 1, or 2;

R$_5$ is H; optionally substituted alkyl, optionally substituted alkenyl, or optionally substituted alkynyl, each containing 0, 1, 2, or 3 heteroatoms selected from O, S, or N; optionally substituted carbocyclic, optionally substituted heterocyclic, optionally substituted aryl, or optionally substituted heteroaryl;

R$_3$ and R$_4$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

L is absent or is selected from optionally substituted alkylene, optionally substituted alkenylene or optionally substituted alkynylene, each containing 0, 1, 2, or 3 heteroatoms selected from O, S, or N;

j=0, 1, 2, 3, or 4;

k=0, 1, 2, or 3;

m=0, 1, or 2;

---- denotes a carbon-carbon single bond

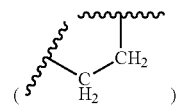

or double bond

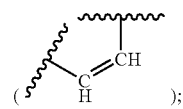

and

LG is a leaving group;

with a compound of formula XI:

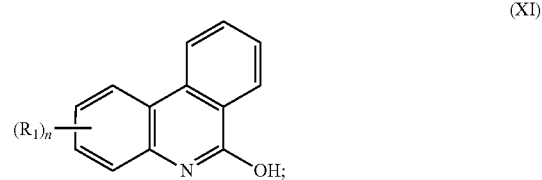

(XI)

wherein:

each R$_1$ is independently selected from (vi) halogen, hydroxy, amino, —CN, —CF$_3$, —N$_3$, —NO$_2$, —SR$_4$, —SOR$_4$, —SO$_2$R$_4$, —N(R$_3$)S(O)$_2$—R$_4$, —N(R$_3$)(SO$_2$)NR$_3$R$_4$, —NR$_3$R$_4$, —C(O)—O_R$_4$, —C(O)R$_4$, —C(O)NR$_3$R$_4$, or —N(R$_3$)C(O)R$_4$;

(vii) optionally substituted aryl;

(viii) optionally substituted heteroaryl;

(ix) optionally substituted heterocyclic;

(x) optionally substituted carbocyclic; or (vi) optionally substituted alkyl, optionally substituted alkenyl, or optionally substituted alkynyl, each containing 0, 1, 2, or 3 heteroatoms selected from O, S, or N;

wherein at least one of R$_1$ is halogen or —OR$_4$—; and n is 1, 2, 3, or 4;

to thereby produce a compound of formula I.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present invention. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds of this invention may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

EXAMPLES

The compounds and processes of the present invention will be better understood in connection with the following examples, which are intended as an illustration only and not to limit the scope of the invention. The following examples can be prepared according to either Scheme 1 or Scheme 2 as described above. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

N-((2R,6S,13aS,14aR,16aS,Z)-2-(3-fluorophenanthridin-6-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide

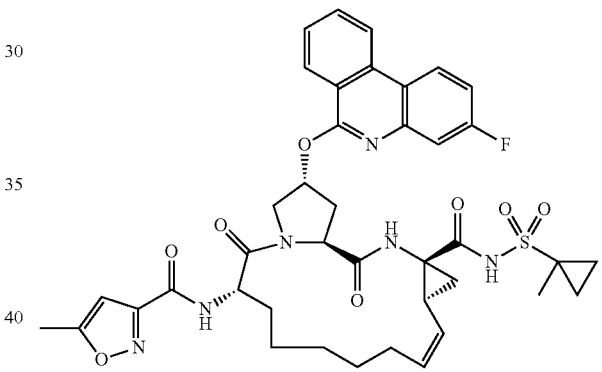

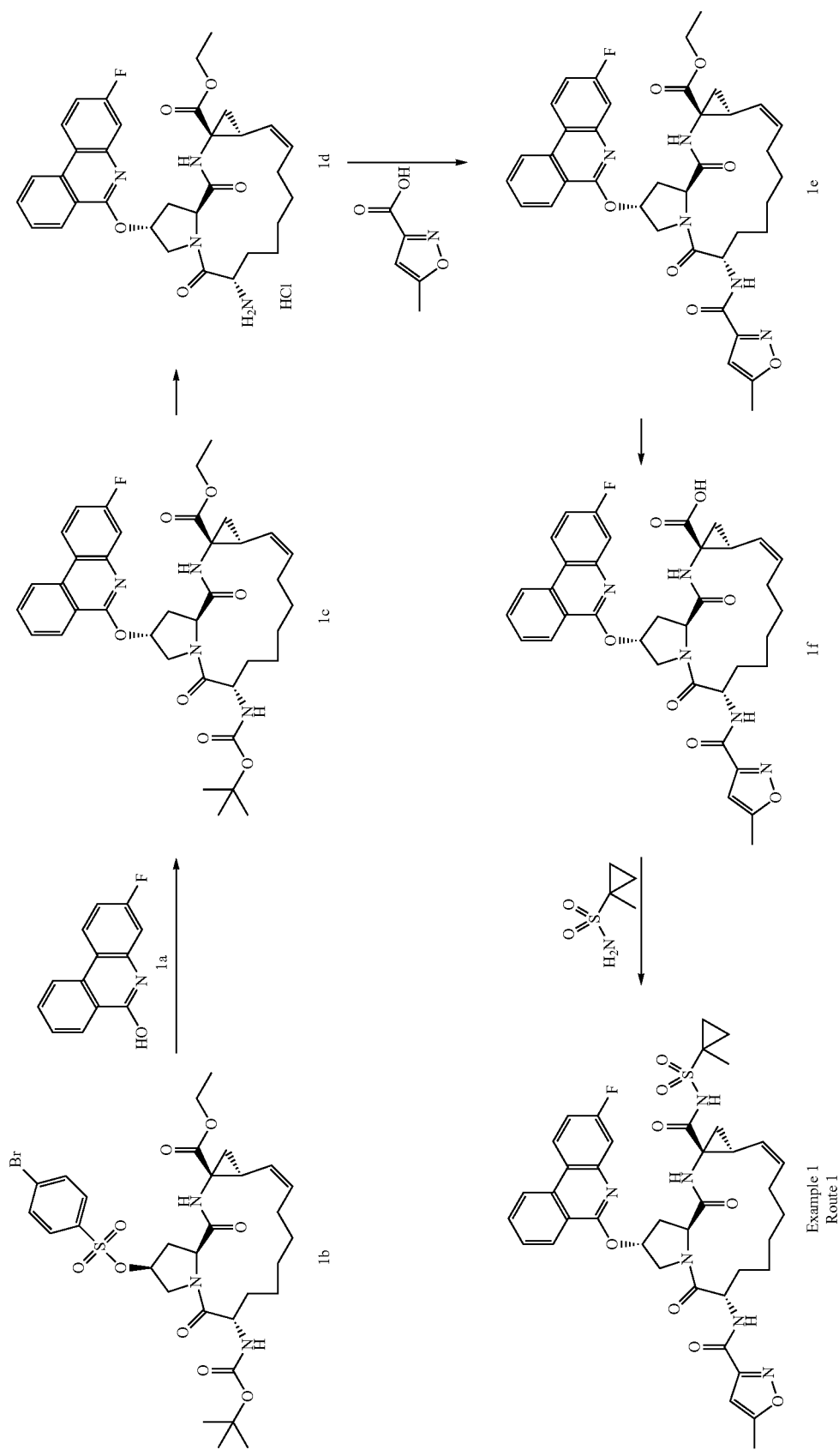

Example 1a

3-Fluorophenanthridin-6-ol

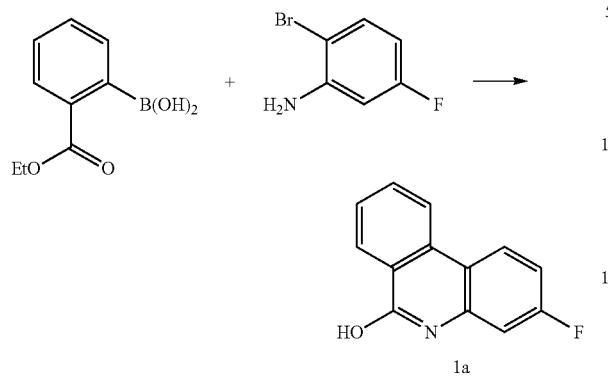

A mixture of 2-(ethoxycarbonyl)phenylboronic acid (7.0 g, 39 mmol), 2-bromo-5-fluoroaniline (7.4 g, 39 mmol), dicyclohexyl(2',6'-dimethoxybiphenyl-2-yl)phosphine (S-Phos, 0.32 g, 0.78 mmol), sodium acetate (4.1 g, 39 mmol), and palladium acetate (0.087 g, 0.39 mmol) in 18 ml. of ethanol was heated with stirring at 80° C. for 18 h. Additional 2-(ethoxycarbonyl)phenylboronic acid (2.0 g), S-Phos (0.095 g), palladium acetate (0.020 g), and sodium carbonate (1.2 g) was added and the mixture was stirred for 18 h. The solvent was removed by evaporation under reduced pressure, and the resulting solid was isolated by vacuum filtration, washing the remaining solid with water and then hexane. The remaining solid and dried in vacuo @50° C. to provide the title compound (4.39 g, 53% yield) which was used without further purification.

Example 1c (2R,6S,13aS,14aR,16aS,Z)-ethyl 6-(tert-butoxycarbonylamino)-2-(3-fluorophenanthridin-6-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate

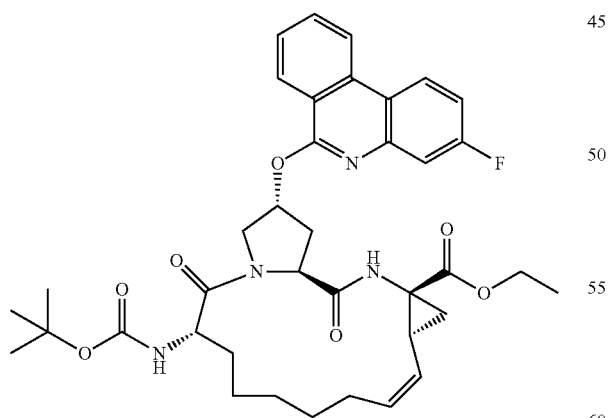

A mixture of (2R,6S,13aS,14aR,16aS,Z)-ethyl 2-(4-bromophenylsulfonyloxy)-6-(tert-butoxycarbonylamino)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate (1b, 2.3 g, 3.2 mmol), 3-fluorophenanthridin-6-ol (Example 1a, 0.688 g, 3.23 mmol) and cesium carbonate (1.2 g, 3.6 mmol) in dimethylformamide (32 ml) was heated @80° C. for 5 h. The reaction mixture was cooled to room temperature and partitioned between ethyl acetate and 2 N HCl. The organic phase was washed with water and then saturated aqueous sodium chloride, dried over anhydrous magnesium sulfate, filtered, and evaporated. The resulting solid was purified by flash chromatography on silica gel, eluting with acetone/hexane, to provide the title compound (1.3 g, 60% yield).

Example 1d (2R,6S,13aS,14aR,16aS,Z)-ethyl 6-amino-2-(3-fluorophenanthridin-6-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate hydrochloride

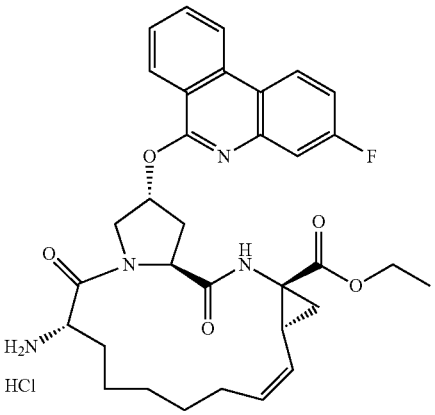 [SMILES: Cl ; CCOC(=O)[C@@]12C[C@H]1/C=C\CCCCC[C@H](N)C(=O)N1C[C@H](Oc3nc4cc(F)ccc4c4ccccc34)C[C@H]1C(=O)N2]

A solution of (2R,6S,13aS,14aR,16aS,Z)-ethyl 6-(tert-butoxycarbonylamino)-2-(3-fluorophenanthridin-6-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate (Example 1c, 1.3 g, 1.9 mmol) in 1 N HCl (4.7 ml, 19 mmol) was stirred at room temperature for 2 h. The reaction mixture was diluted with chloroform and toluene and evaporated to provide the title compound (1.11 g, quantitative yield) as a colorless solid. This material was used without further purification.

Example 1e (2R,6S,13aS,14aR,16aS,Z)-ethyl 2-(3-fluorophenanthridin-6-yloxy)-6-(5-methylisoxazole-3-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate

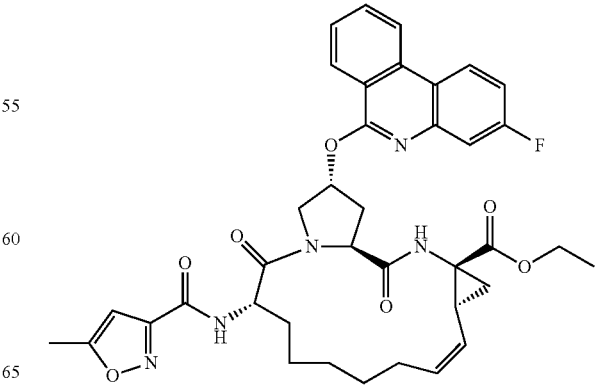

A mixture of (2R,6S,13aS,14aR,16aS,Z)-ethyl 6-amino-2-(3-fluorophenanthridin-6-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate (Example 1d, 1.11 g, 1.89 mmol) was dissolved in dimethylformamide (19 mL) and treated with N-methylmorpholine (0.73 ml, 6.6 mmol) followed by 5-methylisoxazole-3-carboxylic acid (0.264 g, 2.074 mmol) and HATU (0.860 g, 2.263 mmol). The reaction mixture was stirred at room temperature for 1 h, diluted with 2 N HCl and extracted with ethyl acetate. The organic layer was washed with water, dried over anhydrous magnesium sulfate, filtered, and evaporated under reduced pressure. The residue was purified by flash chromatography on silica gel, eluting with acetone/hexane, to provide the title compound (0.94 g, 72% yield).

Example 1f (2R,6S,13aS,14aR,16aS,Z)-2-(3-fluorophenanthridin-6-yloxy)-6-(5-methylisoxazole-3-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylic acid

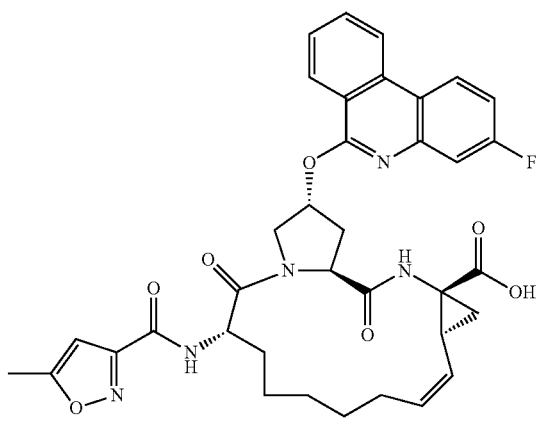 [SMILES: Cc1cc(C(=O)N[C@H]2CCCCC/C=C\[C@@H]3C[C@@]3(C(=O)O)NC(=O)[C@@H]3C[C@@H](Oc4nc5cc(F)ccc5c5ccccc45)CN3C2=O)no1]

(2R,6S,13aS,14aR,16aS,Z)-ethyl 2-(3-fluorophenanthridin-6-yloxy)-6-(5-methylisoxazole-3-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate (846 mg, 1.21 mmol) was dissolved in tetrahydrofuran (6 mL), methanol (3 mL), and water (3 mL) and lithium hydroxide monohydrate (76 mg, 1.8 mmol) was added. The reaction mixture was heated at 40° C. for 4 h. The mixture was cooled to rt and partitioned between 2 N HCl and dichloromethane. The organic layer was concentrated under reduced pressure and then azeoptroped with toluene and chloroform to provide the title compound (0.812 g, quantitative yield) as a colorless solid that was used without further purification.

Example 1

N-((2R,6S,13aS,14aR,16aS,Z)-2-(3-fluorophenanthridin-6-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide The product of Example 1f, (2R,6S,13aS,14aR,16aS,Z)-2-(3-fluorophenanthridin-6-yloxy)-6-(5-methylisoxazole-3-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylic acid (0.812 g, 1.21 mmol) was dissolved in dichloroethane (12 mL) and 4A sieves were added to the flask. To this mixture was added carbonyldiimidazole (505 mg, 3.11 mmol) and the reaction mixture was heated at 40° C. for 2 h. The reaction mixture was cooled to room temperature and 1-methylcyclopropane-1-sulfonamide (426 mg, 3.15 mmol) was added followed by 1,8-diazabicycloundecene (0.548 ml, 3.64 mmol). The reaction mixture was stirred at room temperature for 3 h. and then cooled to 0° C. and 4 N HCl in dioxane (2.5 mL, 10 mmol) was added. The resulting solid was washed copiously with dichloromethane and the filtrate was washed with 2 N HCl and then water. The organic layer was dried over anhydrous magnesium sulfate, filtered, and evaporated under reduced pressure. The residue was purified by flash chromatography on silica gel eluting with acetone/hexane followed by acetone/chloroform to provide the title compound (0.45 g, 47% yield) as a white solid. MS (ESI): m/z=787.2 [M+H]$^+$.

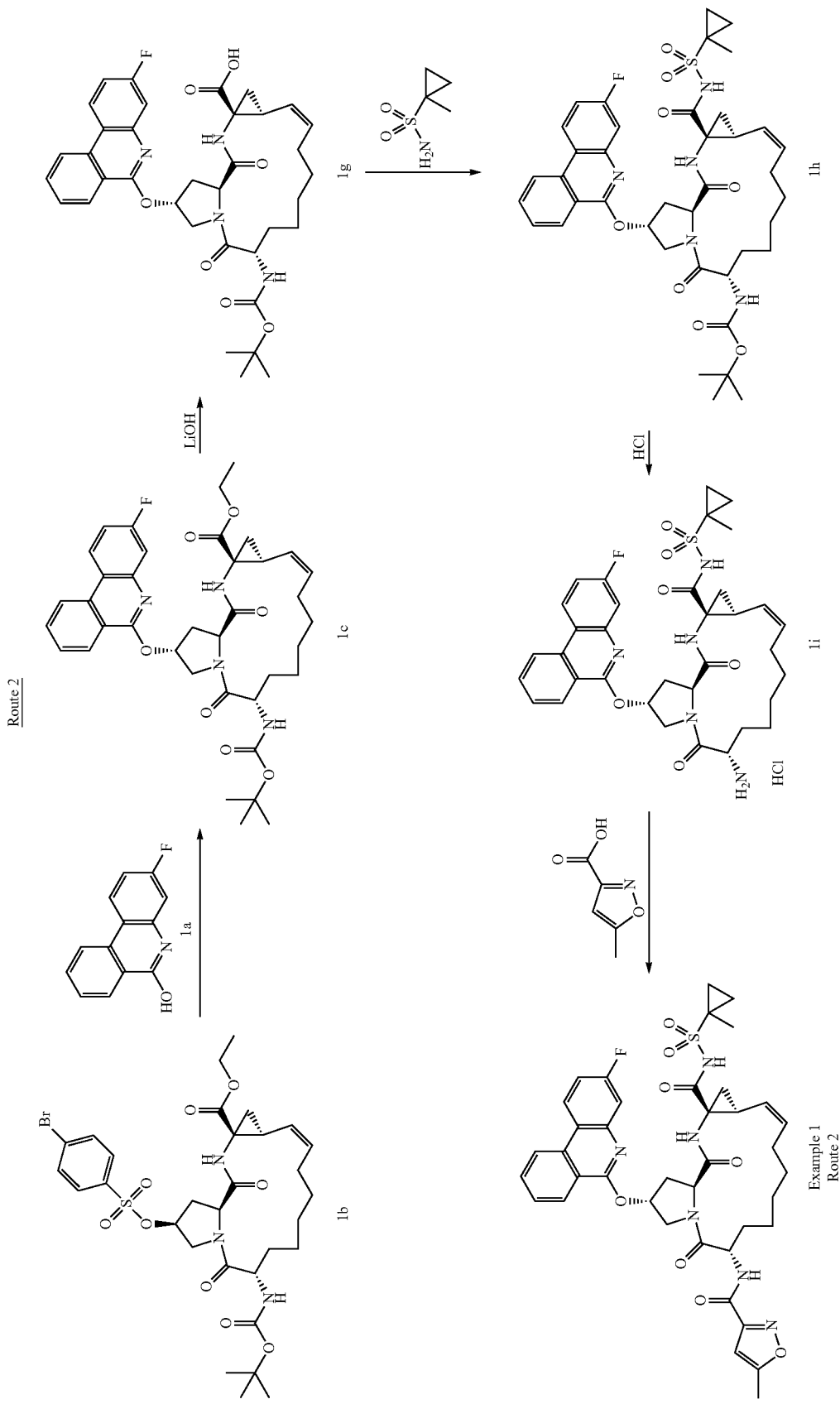

Example 1g (2R,6S,13aS,14aR,16aS,Z)-6-(tert-butoxycarbonylamino)-2-(3-fluorophenanthridin-6-yloxy)-5,16-dioxo-1,2,3,5,6,7,8,9,10,11,13',14,14',15,16,16a-hexadecahydrocyclopropa[e]pyrrolo[1,2-a][1,4]diazacyclopentadecine-14$^a$-carboxylic acid

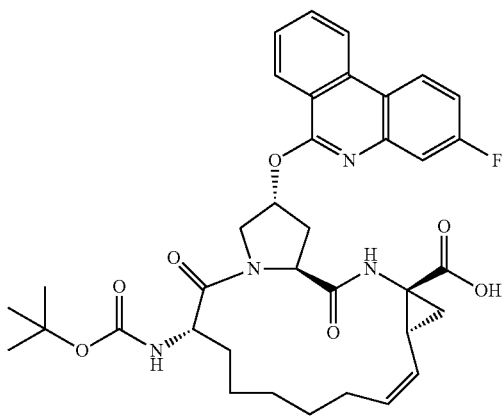 [SMILES: CC(C)(C)OC(=O)N[C@H]1CCCCC/C=C\[C@@H]2C[C@@]2(C(=O)O)NC(=O)[C@@H]2C[C@@H](Oc3nc4cc(F)ccc4c4ccccc34)CN2C1=O]

A mixture of (2R,6S,13aS,14aR,16aS,Z)-ethyl 6-(tert-butoxycarbonylamino)-2-(3-fluorophenanthridin-6-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate (0.90 g, 1.3 mmol, Example 1c) and lithium hydroxide monohydrate (0.384 g, 9.15 mmol) was dissolved in tetrahydrofuran (6.5 mL), methanol (3.3 mL), and water (3.3 mL) and heated to 50° C. for 2 h. The reaction mixture was cooled to room temperature and concentrated under reduced pressure to remove all tetrahydrofuran and methanol. The mixture was diluted with 2 N HCl and the resulting solid was collected by filtration and dried on high vacuum overnight to provide the title compound (0.73 g, 85% yield) as a white solid. This material was taken forward without additional purification.

Example 1h tert-butyl (2R,6S,13aS,14aR,16aS,Z)-2-(3-fluorophenanthridin-6-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate

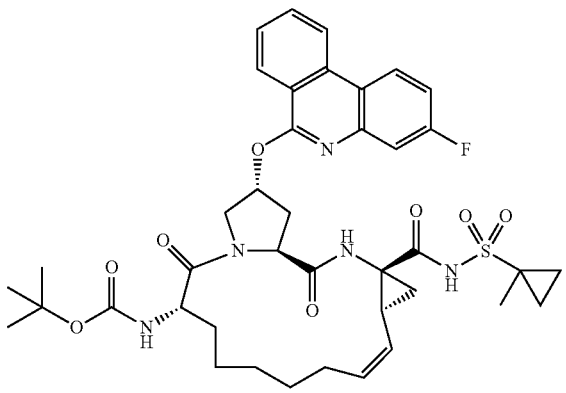 [SMILES: CC(C)(C)OC(=O)N[C@H]1CCCCC/C=C\[C@@H]2C[C@@]2(C(=O)NS(=O)(=O)C2(C)CC2)NC(=O)[C@@H]2C[C@@H](Oc3nc4cc(F)ccc4c4ccccc34)CN2C1=O]

The product of example 1g ((2R,6S,13aS,14aR,16aS,Z)-6-(tert-butoxycarbonylamino)-2-(3-fluorophenanthridin-6-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylic acid (3.0 g, 4.5 mmol)) was dissolved in dichloroethane (45 mL) and crushed 3 Å molecular sieves (3 g) were added and the mixture stirred for 15 min at room temperature. Carbonyl diimidazole (1.91 g, 11.8 mmol) was added and the reaction mixture was heated to 40° C. for 2 h. The reaction mixture was cooled to room temperature and 1-methylcyclopropane-1-sulfonamide (1.60 g, 11.8 mmol) was added. DBU (2.07 g, 13.6 mmol) was then added and the reaction mixture was stirred at room temperature for 16 h. The reaction mixture was filtered through Celite and rinsed with ethyl acetate, and the filtrate was washed with 1 N HCl. The resulting organic phase was washed with saturated aqueous sodium chloride solution, dried over anhydrous magnesium sulfate, filtered, and evaporated under reduced pressure. The residue was purified by flash chromatography on silica gel eluting with chloroform/ethyl acetate (3:1) to provide the title compound (3.0 g, 86% yield) as a white solid.

Example 1i (2R,6S,13aS,14aR,16aS,Z)-6-amino-2-(3-fluorophenanthridin-6-yloxy)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide

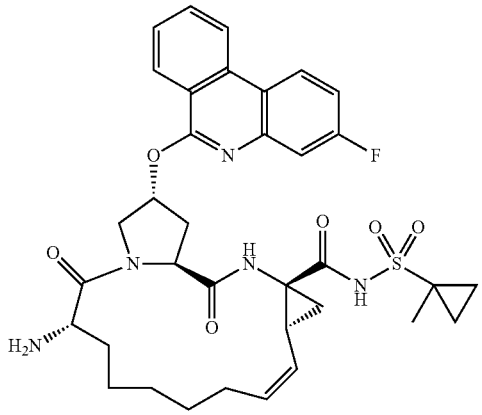 [SMILES: CC1(S(=O)(=O)NC(=O)[C@@]23C[C@H]2/C=C\CCCCC[C@H](N)C(=O)N2C[C@H](Oc4nc5cc(F)ccc5c5ccccc45)C[C@H]2C(=O)N3)CC1]

A solution of the product of Example 1h (tert-butyl (2R,6S,13aS,14aR,16aS,Z)-2-(3-fluorophenanthridin-6-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate, 16.0 g, 20.6 mmol) in dichloromethane (100 mL) and 4 N HCl in dioxane (100 mL) was stirred at room temperature for 90 min and then evaporated under reduced pressure. The residue was partitioned between ethyl acetate (200 mL) and saturated aqueous sodium bicarbonate solution (200 mL) and the resulting solid isolated by filtration of the mixture through a medium porosity sintered glass funnel. The isolated solid was washed with water (2×150 mL) and dried under reduced pressure to provide the title compound (12.2 g, 88% yield).

Example 1

Route 2

N-((2R,6S,13aS,14aR,16aS,Z)-2-(3-fluorophenanthridin-6-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide A solution of the product of Example 1l ((2R,6S,13aS,14aR,16aS,Z)-6-amino-2-(3-fluorophenanthridin-6-yloxy)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide, 2.0 g, 3.0 mmol) and 5-methylisoxazole-3- carboxylic acid (0.38 g, 3.0 mmol) in dimethylformamide (30 mL) was cooled to 0° C. To this mixture was added N-methylmorpholine (0.90 g, 8.9 mmol) followed by HATU (1.46 g, 3.84 mmol). The reaction mixture was stirred at to 0° C. for 30 min. To this mixture was added 1 N HCl (15 mL) followed by ethyl acetate (250 mL). The organic layer was washed with water and then saturated aqueous sodium chloride solution, separated, dried over anhydrous magnesium sulfate, filtered and evaporated under reduced pressure. The residue was purified by flash chromatography on silica gel eluting with a gradient of acetone/hexane (1:3 to 1:2) to provide the title compound (1.9 g, 88% yield) as a white solid. MS (ESI): m/z=787.0 [M+H]+.

Example 1g

Route 3 (Displacement of Chlorophenanthridine by Hydroxy Acid)

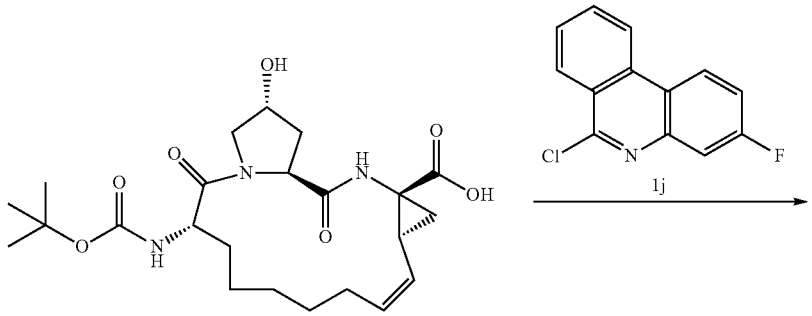

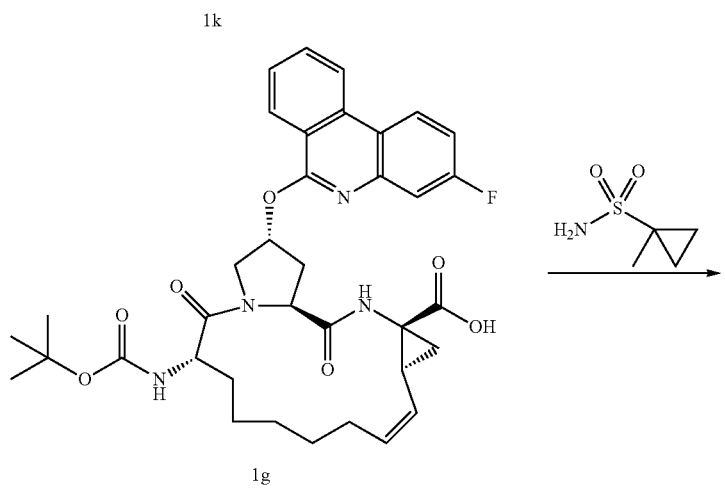

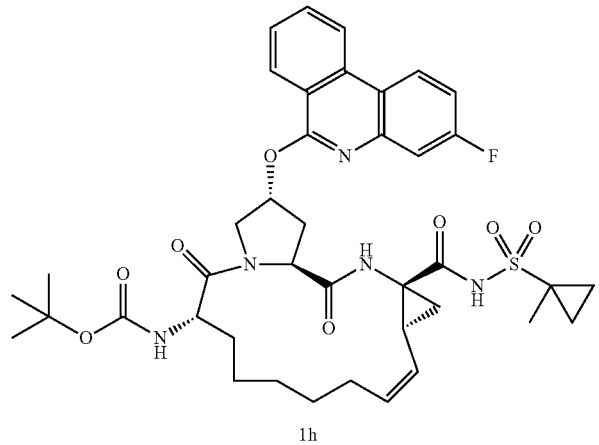

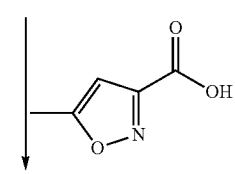

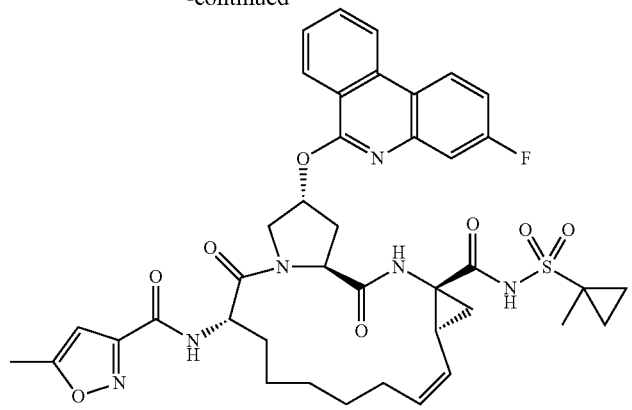

Example 1
A-1258370

Example 1j 6-chloro-3-fluorophenanthridine

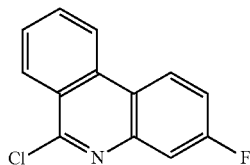 [SMILES: Fc1ccc2c(c1)nc(Cl)c1ccccc12]

To a mixture of 3-fluorophenanthridin-6-ol (Example 1a, 1.58 g, 7.41 mmol) in phosphorus oxychloride (11.7 g, 7.1 mL, 76 mmol) was added dimethylformamide (0.34 g, 0.46 mmol), and the reaction mixture was warmed to 65° C. and stirred under nitrogen for 1 h. The reaction mixture was cooled to room temperature, followed by the careful addition of ice to the reaction mixture. The mixture was stirred for 20 min, and the extracted with ethyl acetate. The resulting organic layer was washed with saturated aqueous sodium chloride solution, dried over anhydrous magnesium sulfate, filtered, and evaporated to provide the title compound (1.2 g, 70% yield), which was used without further purification.

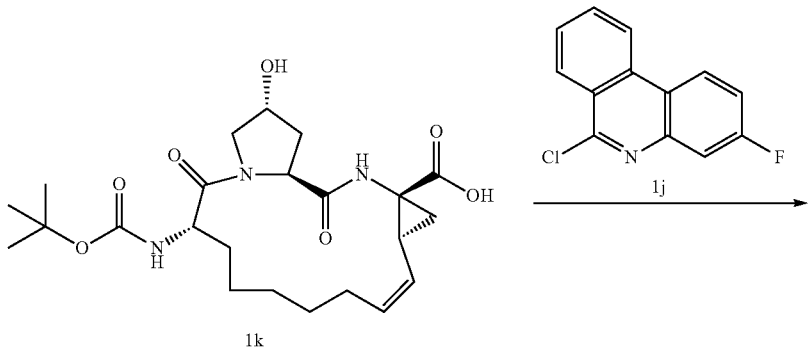

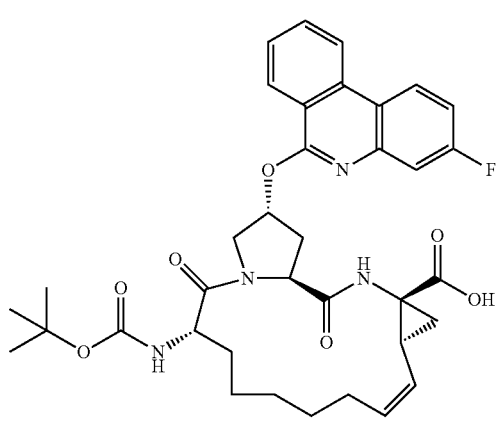

Example 1g

Route 3

(2R,6S,13aS,14aR,16aS,Z)-6-(tert-butoxycarbonylamino)-2-(3-fluorophenanthridin-6-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylic acid A mixture of (2R,6S,13aS,14aR,16aS,Z)-6-(tert-butoxycarbonylamino)-2-hydroxy-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylic acid (1k, 3.00 g, 6.44 mmol), 6-chloro-3-fluorophenanthridine (1j, 1.64 g, 7.09 mmol) and sodium 2-methylbutan-2-olate (2.84 g, 25.8 mmol) in dimethylformamide (21 mL) was stirred at room temperature for 2 h. An additional aliquot of sodium 2-methylbutan-2-olate (0.24 g, 2.8 mmol) was added and the reaction mixture was stirred for 1 h at room temperature. The reaction mixture was diluted with ethyl acetate and washed with 1 N HCl. The resulting aqueous phase was extracted with ethyl acetate, and the combined organic layer was washed with water followed by saturated aqueous sodium chloride solution. The organic layer was dried over anhydrous magnesium sulfate, filtered, and evaporated under reduced pressure. The resulting residue was purified by flash chromatography on silica gel, eluting first with chloroform followed by a chloroform/methanol/acetic acid gradient (98:2:0.2 to 95:5:0.2) to provide the title compound (3.3 g, 78% yield). This material was identical to the product of Example 1g prepared according to Route 2.

Example 2

N-((2R,6S,13aS,14aR,16aS,Z)-14a-(cyclopropylsulfonylcarbamoyl)-2-(8-fluorophenanthridin-6-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide.

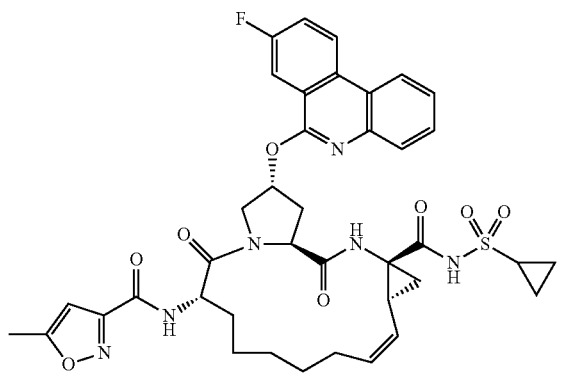 [SMILES: Cc1cc(C(=O)N[C@H]2CCCCC/C=C\[C@@H]3C[C@@]3(C(=O)NS(=O)(=O)C3CC3)NC(=O)[C@@H]3C[C@@H](Oc4nc5ccccc5c5ccc(F)cc45)CN3C2=O)no1]

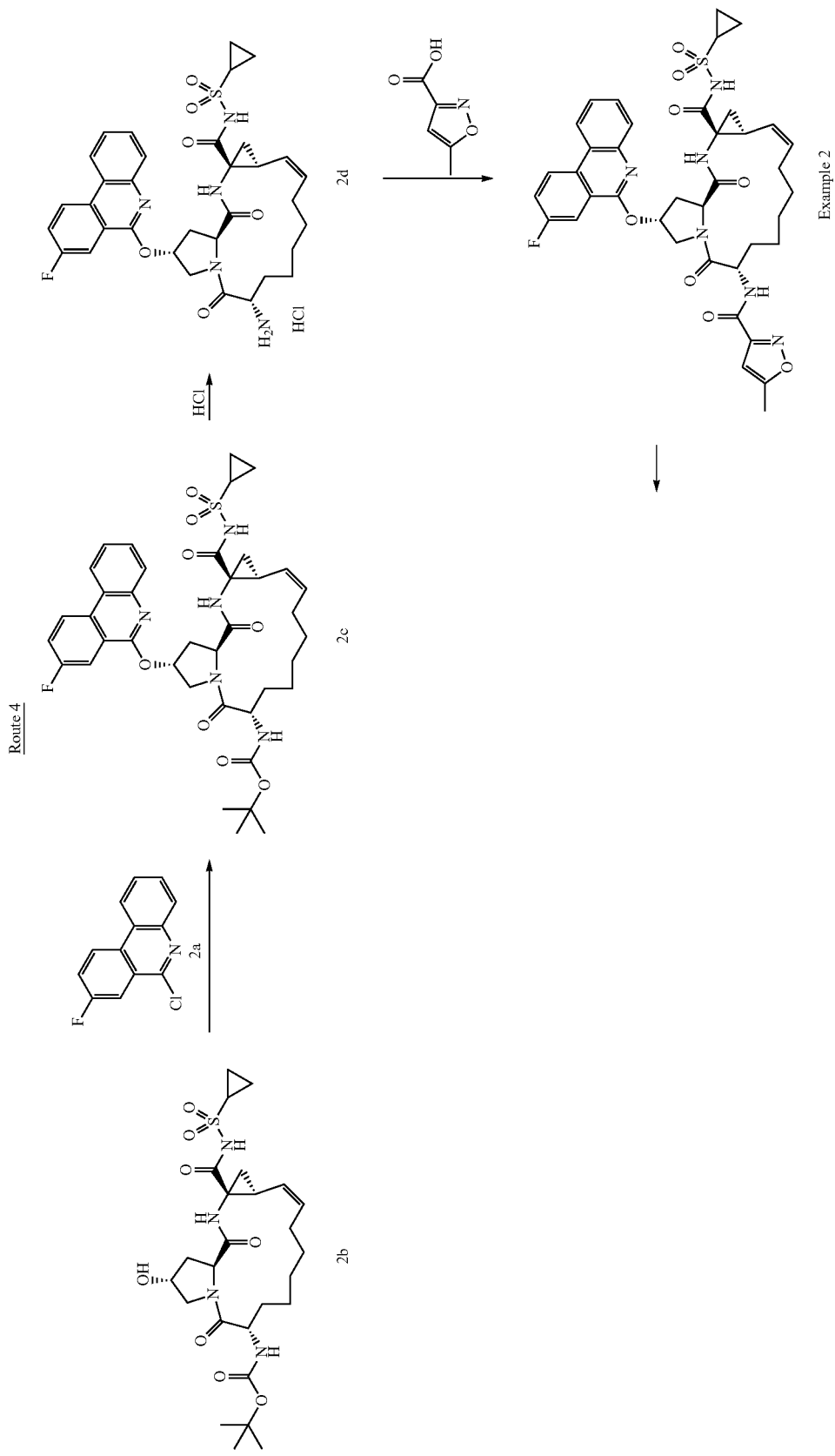

Example 2a 8-fluorophenanthridin-6-ol

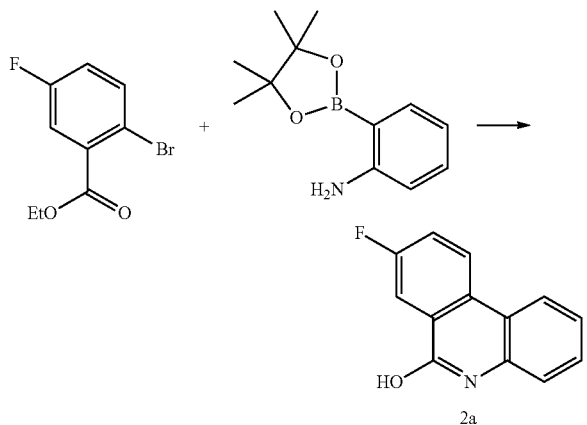

2a

A mixture of methyl 2-bromo-5-fluorobenzoate (0.250 g, 1.07 mmol), 2-(4,4,5,5-tetramethyl-1,3,2-dioxaborolan-2-yl) aniline (0.235 g, 1.07 mmol), palladium acetate (2.4 mg, 0.01 eq.), dicyclohexyl(2',6'-dimethoxybiphenyl-2-yl)phosphine (8.81 mg, 0.021 mmol), and sodium carbonate (0.114 g, 1.073 mmol) in ethanol (5.4 mL) was heated to 80° C. for 3 h. The reaction mixture was cooled to room temperature and concentrated under reduced pressure. The resulting residue was triturated with hexane, and isolated by vacuum filtration, washed with water, and dried to provide the title compound (0.15 g, 65% yield) which was used without further purification.

Example 2b 6-chloro-8-fluorophenanthridine

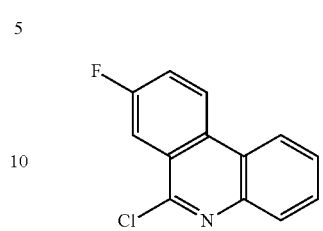

To a mixture of 8-fluorophenanthridin-6-ol (Example 2a, 0.15 g, 0.69 mmol) in phosphorus oxychloride (1.06 g, 0.65 mL, 6.9 mmol) was added dimethylformamide (5 mg, 5 μL), and the reaction mixture was warmed to 80° C. and stirred under nitrogen for 3 h. The reaction mixture was cooled to room temperature and evaporated under reduced pressure. The residue was triturated with hexane, and the resulting solid isolated by vacuum filtration, washed with water, and dried to provide the title compound (0.15 g, 95% yield) which was used without additional purification.

Example 2d tert-butyl (2R,6S,13aS,14aR,16aS,Z)-14a-(cyclopropylsulfonylcarbamoyl)-2-(8-fluorophenanthridin-6-yloxy)-5,16-dioxo-1,2,3,5,6,7,8,9,10,11,13a,14,14a, 15,16,16a-hexadecahydrocyclopropa[e]pyrrolo[1,2-a][1,4]diazacyclopentadecin-6-ylcarbamate

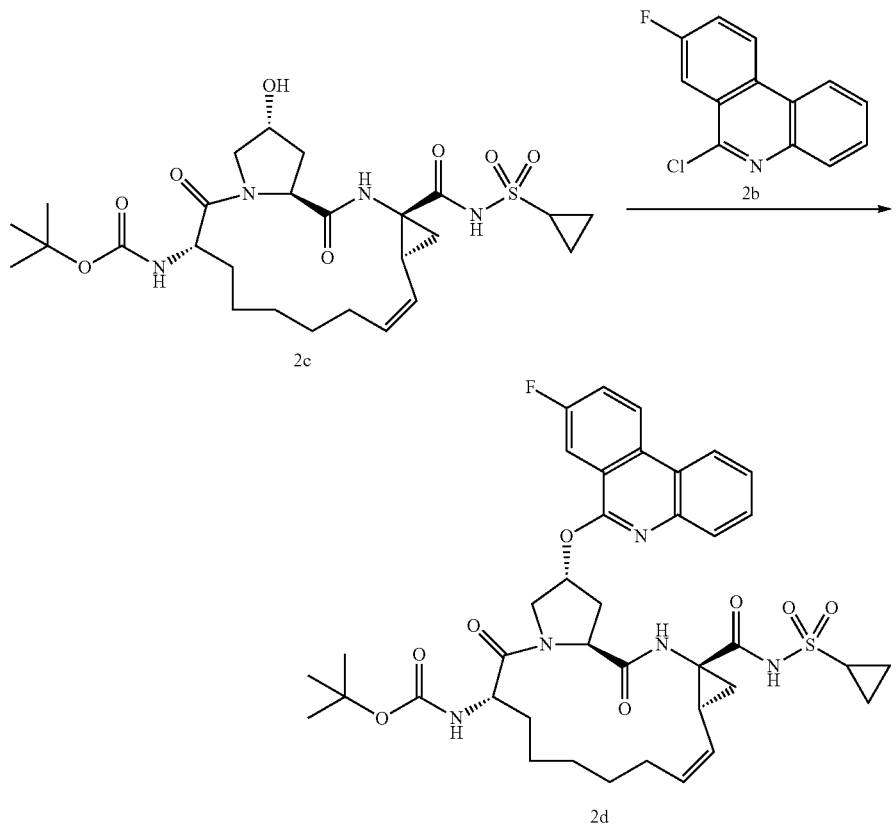

A mixture of tert-butyl (2R,6S,13aS,14aR,16aS,Z)-14a-(cyclopropylsulfonylcarbamoyl)-2-hydroxy-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate (2c, 0.376 g, 0.660 mmol), 6-chloro-8-fluorophenanthridine (2b, 0.153 g, 0.660 mmol) and sodium 2-methylbutan-2-olate (0.218 g, 1.981 mmol) in dimethylformamide (6.6 mL) was stirred at room temperature for 2 h. The reaction mixture was added dropwise to 2N HCl (200 mL) and the resulting solid was collected by vacuum filtration, rinsed with water, and dried. The solid was purified by flash chromatography on silica gel, eluting with acetone/hexane, to provide the title compound (0.355 g, 70% yield) as a white solid.

Example 2e (2R,6S,13aS,14aR,16aS,Z)-6-amino-N-(cyclopropylsulfonyl)-2-(8-fluorophenanthridin-6-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide hydrochloride

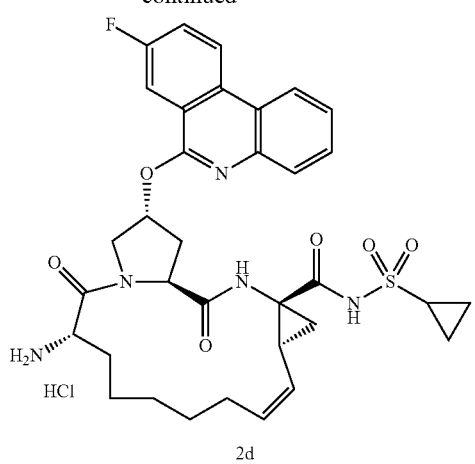

2d

Example 2f

N-((2R,6S,13aS,14aR,16aS,Z)-14a-(cyclopropylsulfonylcarbamoyl)-2-(8-fluorophenanthridin-6-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide

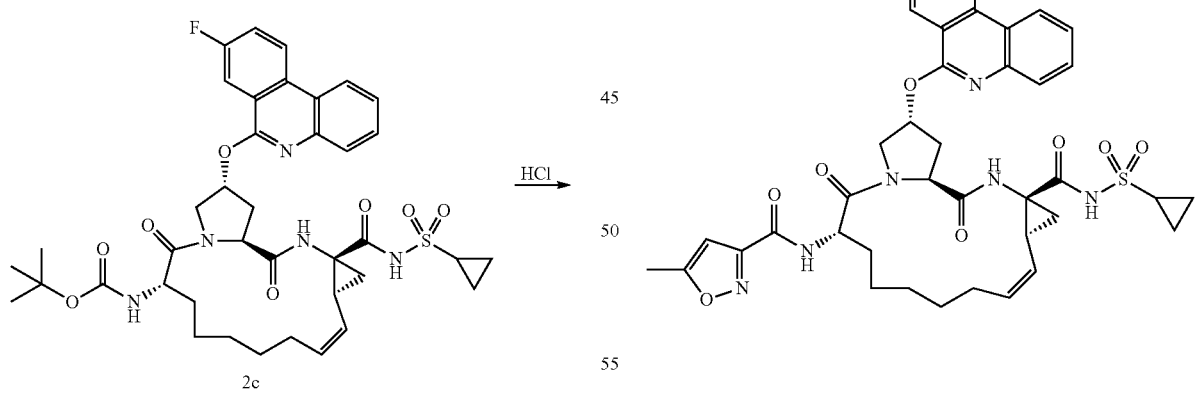

The title compound was prepared according to the procedure utilized for the preparation of Example 1, route 2, replacing the product of Example 11 with the product of Example 2e. The product was purified by flash chromatography on silica gel eluting with a gradient of acetone/hexane to provide the title compound (17.5 mg, 50% yield) as a white solid. MS (ESI): m/z=774.0 [M+H]$^+$.

Example 3

Synthesis of the Cyclic Peptide Precursor

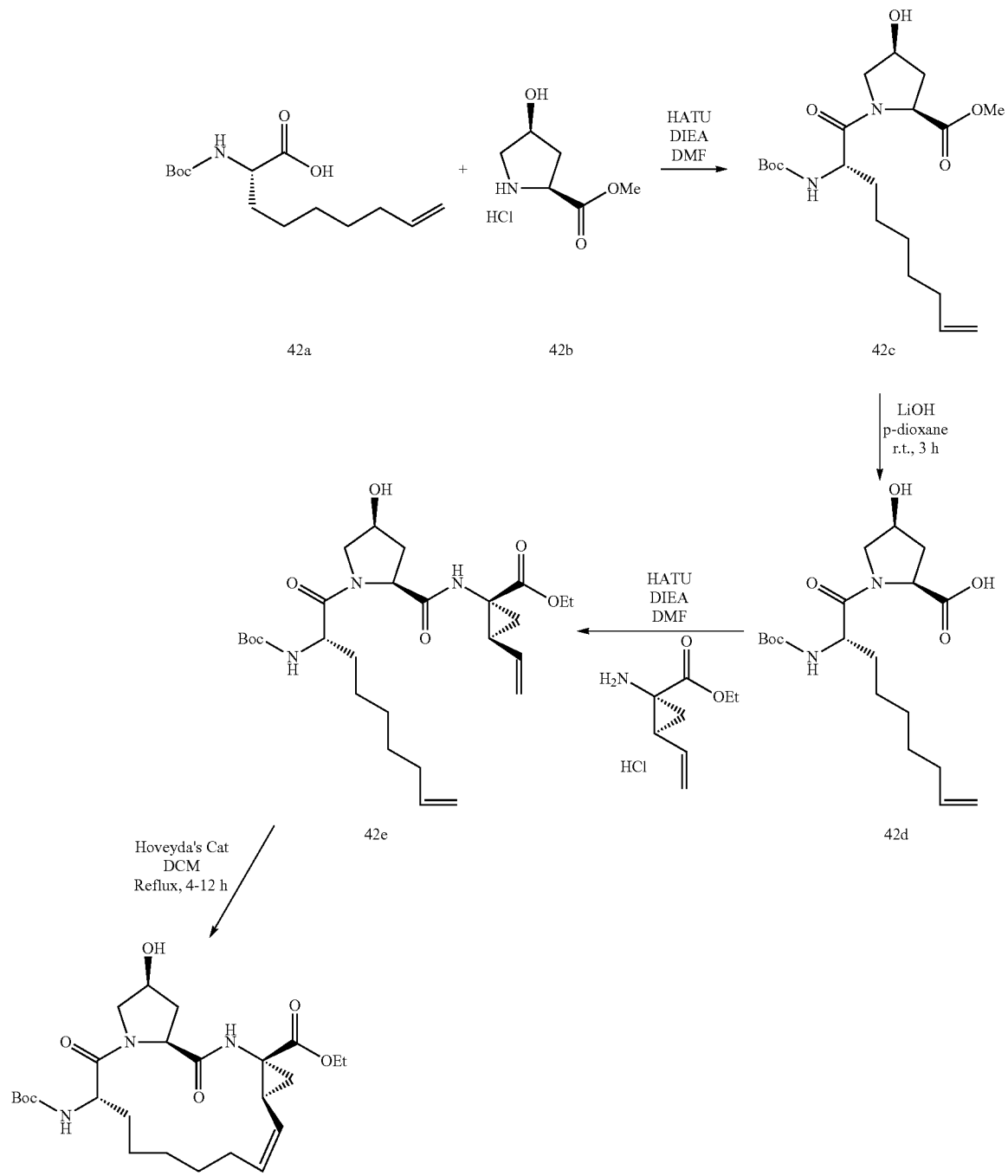

To a solution of Boc-L-2-amino-8-nonenoic acid 42a (1.36 g, 5 mol) and the commercially available cis-L-hydroxyproline methyl ester 42b (1.09 g, 6 mmol) in 15 ml DMF, was added DMA (4 ml, 4 eq.) and HATU (4 g, 2 eq). The coupling was carried out at 0° C. over a period of 1 hour. The reaction mixture was diluted with 100 mL EtOAc, and followed by washing with 5% citric acid 2×20 ml, water 2×20 ml, 1M NaHCO$_3$ 4×20 ml and brine 2×10 ml, respectively. The organic phase was dried over anhydrous Na$_2$SO$_4$ and then was evaporated, affording the dipeptide 42c (1.91 g, 95.8%) that was identified by HPLC (Retention time=8.9 min, 30-70%, 90% B), and MS (found 421.37, M+Na$^+$).

The dipeptide 42c (1.91 g) was dissolved in 15 mL of dioxane and 15 mL of 1 N LiOH aqueous solution and the hydrolysis reaction was carried out at room temperature for 4 hours. The reaction mixture was acidified by 5% citric acid and extracted with 100 mL EtOAc, and followed by washing with water 2×20 ml, and brine 2×20 ml, respectively. The organic phase was dried over anhydrous $Na_2SO_4$ and then removed in vacuum, yielding the free carboxylic acid compound 42d (1.79 g, 97%), which was used for next step synthesis without need for further purification.

To a solution of the free acid obtained above (1.77, 4.64 mmol) in 5 ml DMF, D-β-vinyl cyclopropane amino acid ethyl ester (0.95 g, 5 mmol), DIEA (4 ml, 4 eq.) and HATU (4 g, 2 eq) were added. The coupling was carried out at 0° C. over a period of 5 hours. The reaction mixture was diluted with 80 mL EtOAc, and followed by washing with 5% citric acid 2×20 ml, water 2×20 ml, 1M $NaHCO_3$ 4×20 ml and brine 2×10 ml, respectively. The organic phase was dried over anhydrous $Na_2SO_4$ and then evaporated. The residue was purified by silica gel flash chromatography using different ratios of hexanes:EtOAc as elution phase (5:1→3:1→1:1→1:2→1:5). The linear tripeptide 42e was isolated as an oil after removal of the elution solvents (1.59 g, 65.4%), identified by HPLC (Retention time=11.43 min) and MS (found 544.84, M+Na$^+$).

A solution of the linear tripeptide 42e (1.51 g, 2.89 mmol) in 200 ml dry DCM was deoxygenated by bubbling $N_2$. Hoveyda's generation catalyst (5 mol % eq.) was then added as solid. The reaction was refluxed under $N_2$ atmosphere 12 hours. The solvent was evaporated and the residue was purified by silica gel flash chromatography using different ratios of hexanes:EtOAc as elution phase (9:1→5:1→3:1→1:1→1:2→1:5). The cyclic peptide precursor was isolated as a white powder after removal of the elution solvents (1.24 g, 87%), identified by HPLC (Retention time=7.84 min, 30-70%, 90% B), and MS (found 516.28, M+Na$^+$).

(2S,6S,13aS,14aR,16aS,Z)-ethyl 2-(4-bromophenyl-sulfonyloxy)-6-(tert-butoxycarbonylamino)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate

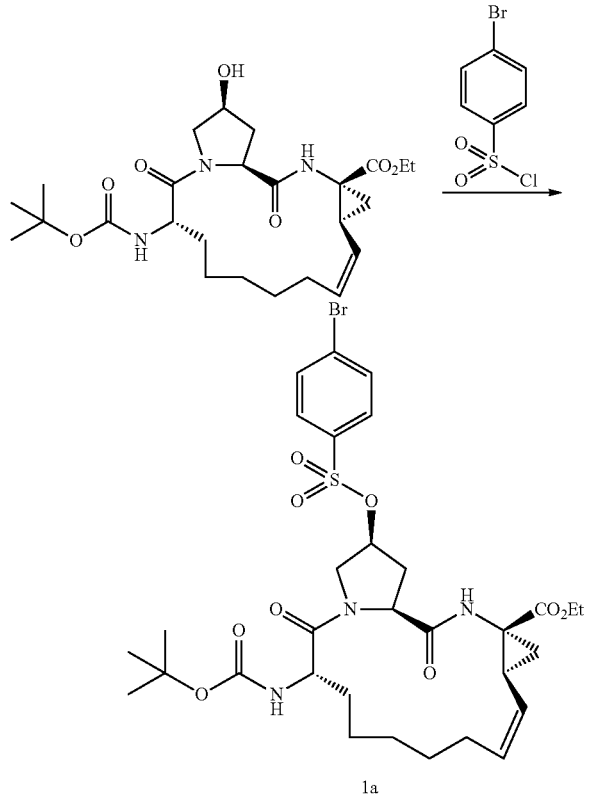

A solution of (2S,6S,13aS,14aR,16aS,Z)-ethyl 6-(tert-butoxycarbonylamino)-2-hydroxy-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate (22.1 g, 44.8 mmol) and DABCO (8.5 g, 76.7 mmol) in toluene (88 mL) was stirred at room temperature. To this solution was added a solution of 4-bromobenzene-1-sulfonyl chloride 17.2 g, 67.2 mmol) in toluene (44 mL). After the addition was complete the reaction mixture was quenched with 10% aqueous sodium carbonate (110 mL) and the mixture stirred for 15 min. Tetrahydrofuran (44 mL) was added and the mixture was washed with 0.5 M HCl, water, and then saturated aqueous sodium chloride. The organic layer was dried over anhydrous magnesium sulfate, filtered, and evaporated under reduced pressure and dried to provide the title compound (27.7 g, 87% yield), which was used without further purification.

Example 4

Measurement of Potency of Inhibition with Purified NS3 Protease Enzyme

The activity of recombinant HCV NS3 proteases derived from isolates representing genotypes 1, 2, 3 or 4 is measured by cleavage of the following peptide substrate:

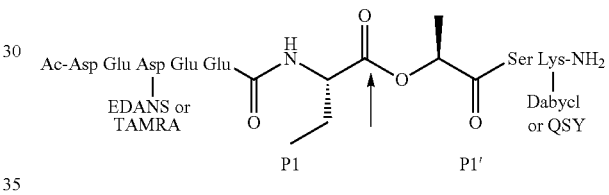

The substrate is labeled with a fluor and a fluorescence quencher. Cleavage results in release of the quencher and an increase in fluorescence. NS3 protease is incubated with a dilution series of inhibitor in 150 mM NaCl, 10% Glycerol, 5 mM DTT, with or without 0.01% dodecyl maltoside for either 30 minutes or 300 minutes. Substrate is added at a concentration of 5 uM to initiate the reaction, and fluorescence is measured at 2 minute intervals for 30 minutes. Enzyme concentrations range from 10 to 100 nM in the absence of detergent, or 10-fold lower in the presence of detergent. Substrate peptides are labeled with either EDANS and DABCYL (excitation 355 nm, emission 485 nm) or TAMRA and QSY (excitation 544 nm, emission 590 nm). For routine IC50 determination, 3-fold serial dilutions starting with initial concentrations of 100 μM, 200 μM, or 2 mM are used. For compounds with $K_i$ values approaching or lower than the enzyme concentration, a tight-binding calculation format is used, with 24 dilutions of inhibitor covering a range of 0 to 100 nM inhibitor. $K_i$ values are calculated using the tight binding assay format, according to the following equation:

$V=A\{[(K+I-E)^2+4KE])^{1/2}-(K+I-E)\}$, where $I$=total inhibitor concentration, $E$=active enzyme concentration, $K$=apparent $K_i$ value and $A=[k_{cat})S/2]$ $[K_m=(S)]$.

Replicon Cell Lines

Two subgenomic replicon cell lines can be used for compound characterization in cell culture: one derived from genotype 1a and one derived from genotype 1b. Both replicon constructs are bicistronic subgenomic replicons essentially similar to those described by Bartenschlager and coworkers (Lohmann et al., *Science* (1999) 285(5424):110-113). The genotype 1a replicon construct contains the NS3-NS5B coding region derived from the H77 strain of HCV (1a-H77) (Blight et al., *J Virol* (2003) 77(5):3181-3190). The first cistron of the construct consists of the first 36 nucleotides of the HCV 1a-H77 core gene fused to a firefly luciferase reporter and a neomycin phosphotransferase (Neo) selectable marker. The luciferase and Neo coding regions are separated by the FMDV 2a protease. The second cistron contains the NS3-NS5B coding region derived from 1a-H77 with the addition of adaptive mutations E1202G in NS3, K1691R in NS4A, and K2040R and S2204I in NS5A. The 1b-Con-1 replicon construct is identical to the 1a-H77 replicon, except that the 5' and 3' NTRs and the NS3-NS5B coding region can be derived from the 1b-Con-1 strain (Blight et al., *Science* (2000) 290 (5498):1972-1974), and the adaptive mutations are E1202G and T1280I in NS3 and S2204I in NS5A.

Replicon Compound Testing

Replicon cell lines can be maintained in Dulbecco's modified Eagles medium (DMEM) containing 100 IU/ml penicillin, 100 mg/ml streptomycin (Invitrogen), 200 mg/ml G418 (Invitrogen) and 10% (v/v) fetal bovine serum (FBS). Replicon-containing cells can be seeded into 96 well plates at a density of 5000 cells per well in 100 µl DMEM containing 5% FBS. The next day, the compound can be initially diluted in dimethyl sulfoxide (DMSO) to generate a 200× stock of the inhibitor in a series of 8 half-log dilutions. The dilution series can then be diluted 100-fold in the medium containing 5% FBS. One hundred microliters of medium with the inhibitor can be added to each well of the overnight cell culture plate already containing 100 µl of DMEM with 5% FBS. In assays where the protein binding effect on inhibitor potency is assessed, the medium from the overnight cell culture plates can be replaced with 200 µl DMEM containing 40% human plasma (Innovative Research) plus 5% FBS as well as compound. The cells can be grown for 4 days in tissue culture incubators. The inhibitory effects of compounds against the replicons can be determined by measuring either the level of luciferase or HCV RNA. The luciferase assay can be conducted using a Luciferase Assay System kit (Promega) following the manufacturer's instructions. Briefly, the cell culture medium is removed and wells are washed with 200 µl of phosphate-buffered saline. To each well Passive Lysis buffer (Promega, Wis.) is added and the plates are incubated for 30 min with rocking to lyse the cells. Luciferin solution (50 µl, Promega) is added, and luciferase activity is measured with a Victor II luminometer (Perkin-Elmer). To determine HCV RNA levels, RNA extractions can be performed using the CellsDirect kit (Invitrogen), and the HCV RNA copy number can be measured using the SuperScript III Platinum One-Step qRT-PCR system (Invitrogen) and primers specific to the HCV 5' nontranslated region. Cytotoxicity can be determined by the 3-[4,5-dimethylhiazol-2-yl]-2,5-diphenyltetrazolium bromide (MTT) colorimetric assay as follows. Replicon cells is plated in 96-well plates (4000 cells per well), the next day compound dilutions are added as in the activity assay, and the cells are grown in the presence of the inhibitors for 4 days. The MTT solution is diluted in DMEM containing 5% FBS and 60 µl of the solution is added to the cells. After 4 hrs, the cells are solubilized by the addition of 30 µl SDS (20% in 0.02 N HCl). The plates are incubated overnight and the optical density can be measured at 570 nm. To determine compounds' $EC_{50}$ and $TD_{50}$, luciferase, RNA inhibition and MTT data can be analyzed using the GraphPad Prism 4 software (equation: sigmoidal dose-response—variable slope).

Mutants in Transient Replicons

Mutations detected in resistance selection studies can be introduced into wild type transient replicon constructs based on genotypes 1a-H77 and 1b-N. Both replicons are bicistronic sub-genomic constructs containing a firefly luciferase reporter similar to those described above, but they do not contain a Neo selectable marker and are therefore only suitable for transient replication assays. The 1a-H77 replicon for transient assays further differs from the replicon in the stable cell line in that it contains NS2 through NS5B in the second cistron. The 1b-N strain replicon contains NS3 through NS5B in the second cistron, with adaptive mutations E1202G in NS3 and S2204I in NS5A. Mutagenesis can be performed using the Stratagene QuikChange XL II site-directed mutagenesis kit. Mutants' sequences can be confirmed, plasmids can be linearized with Xba I restriction enzyme and used as template for in vitro transcription reactions to make mutant replicon RNA for transient transfections. In vitro transcription can be performed with the T7 Megascript kit (Ambion).

Transient replicon transfections can be performed essentially as described by Mo et al. (*Antimicrob Agents Chemother* (2005) 49(10):4305-4314) with slight modifications. Fifteen micrograms of template RNA can be used to electroporate $3 \times 10^6$ cells in a 200 µl volume in a 0.2 cm cuvette. The cells used for transient transfections can be Huh7 cells obtained by curing replicon-containing cells with MN (Mo et al., supra). Electroporation can be done with a Gene Pulser II (Bio-Rad, CA) at 480V and 25 g, using two manual pulses. Transfected cells can be diluted to $7.5 \times 10^4$ cells/ml and plated in 96 well plates at $7.5 \times 10^3$ cells per well in DMEM with 5% FBS and 100 IU/ml penicillin, 100 mg/ml streptomycin (Invitrogen). Four hours post-transfection, one plate is harvested for luciferase measurement; this plate may provide a measure of the amount of input RNA that can be translated, and thus of transfection efficiency. To the remaining plates, test compound serial dilutions in DMSO can be added (0.5% DMSO final concentration), and plates are incubated for 4 days.

Exemplary compounds of the present invention were tested for their anti-HCV activities. Many of the compounds tested showed unexpected anti-HCV activities, including excellent activities in biochemical assays against HCV proteases representing various HCV genotypes, superior activities in standard HCV replicon assays including activity against 1a-H77 and 1b-con1 HCV strains in the absence or presence of 40% human plasma, and/or excellent activities in transient replicon assays against drug-resistant mutants in a number of different HCV genetic backgrounds.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

Those skilled in the art will recognize, or be able to ascertain using no more than routine experimentation, many equivalents of the specific embodiments of the invention described herein. Such equivalents are intended with be encompassed by the following claims.

What is claimed:
1. A compound of formula I:

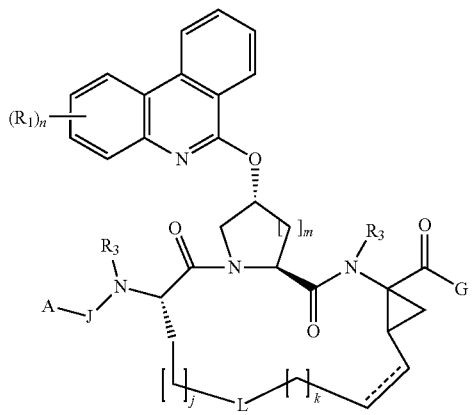

or a pharmaceutically acceptable salt thereof,
wherein:
J is absent, optionally substituted alkylene, optionally substituted alkenylene, optionally substituted alkynylene, —C(O)—, N(R$_3$)—C(O)—, —C(S)—, —C(=NR$_4$)—, —S(O)—, —S(O$_2$)—, or —N(R$_3$)—;

A is optionally substituted alkyl, optionally substituted alkenyl, or optionally substituted alkynyl, each containing 0, 1, 2, or 3 heteroatoms selected from O, S, or N; optionally substituted aryl, optionally substituted arylalkyl, optionally substituted alkoxy, optionally substituted heteroaryl, optionally substituted heterocyclic, or optionally substituted carbocyclic;

each R$_1$ is independently selected from
(i) halogen, hydroxy, amino, —CN, —CF$_3$, —N$_3$, —NO$_2$, —OR$_4$, —SR$_4$, —SOR$_4$, —SO$_2$R$_4$, —N(R$_3$)S(O)$_2$—R$_4$, —N(R$_3$)(SO$_2$)NR$_3$R$_4$, —NR$_3$R$_4$, —C(O)—OR$_4$, —C(O)R$_4$, —C(O)NR$_3$R$_4$, or —N(R$_3$)C(O)R$_4$;
(ii) optionally substituted aryl;
(iii) optionally substituted heteroaryl;
(iv) optionally substituted heterocyclic;
(v) optionally substituted carbocyclic; or
(vi) optionally substituted alkyl, optionally substituted alkenyl, or optionally substituted alkynyl, each containing 0, 1, 2, or 3 heteroatoms selected from O, S, or N;
wherein at least one of R$_1$ is halogen or —OR$_4$;

G is -E-R$_5$;
wherein E is absent; optionally substituted alkylene, optionally substituted alkenylene, optionally substituted alkynylene, each containing 0, 1, 2, or 3 heteroatoms selected from O, S, or N; or —O—, —S—, —N(R$_3$)—, —N(R$_3$)S(O$_p$)—, —N(R$_3$)C(O)—, —N(R$_3$) C(O)S(O)—, —OS(O$_p$)—, —C(O)S (O$_p$)—, or —C(O)N(R$_3$)S(O$_p$)—;

each p is independently 0, 1, or 2;
R$_5$ is H; optionally substituted alkyl, optionally substituted alkenyl, or optionally substituted alkynyl, each containing 0, 1, 2, or 3 heteroatoms selected from O, S, or N;
optionally substituted carbocyclic, optionally substituted heterocyclic, optionally substituted aryl, or optionally substituted heteroaryl;

R$_3$ and R$_4$ are each independently selected at each occurrence from the following:
optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

L is absent or is selected from optionally substituted alkylene, optionally substituted alkenylene or optionally substituted alkynylene, each containing 0, 1, 2, or 3 heteroatoms selected from O, S, or N;
j=0, 1, 2, 3, or 4;
k=0, 1, 2, or 3;
m=0, 1, or 2;
n is 1, 2, 3, or 4; and
===== denotes a carbon-carbon single bond

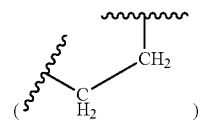

or double bond

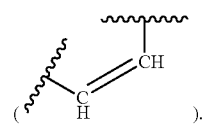

2. The compound of claim 1, or a pharmaceutically acceptable salt thereof, wherein E is —NHS(O)— or —NHS (O$_2$)—, and R$_5$ is cyclopropyl, cyclobutyl, cyclopentyl, cyclohexyl, cycloheptyl, pyridinyl, pyrimidinyl, furanyl, thienyl, pyrrolyl, pyrazolyl, pyrrolidinyl, morpholinyl, piperidinyl, piperazinyl, or imidazolyl, each of which is optionally substituted.

3. The compound of claim 1, or a pharmaceutically acceptable salt, thereof, wherein J is —C(O)— and A is optionally substituted —C$_1$-C$_8$ alkyl, containing 0, 1, 2, or 3 heteroatoms selected from O, S, or N; optionally substituted aryl, optionally substituted —C$_1$-C$_8$ alkoxy, optionally substituted heteroaryl, optionally substituted —C$_3$-C$_{12}$ cycloalkyl, or optionally substituted —C$_3$-C$_{12}$ heterocycloalkyl.

4. The compound of claim 1, or a pharmaceutically acceptable salt thereof, wherein each R$_1$ is independently selected from halogen, hydroxy, amino, —CN, —CF$_3$, —N$_3$, —NO$_2$, —SR$_4$, —SOR$_4$, —SO$_2$R$_4$, —N(R$_3$)S(O$_2$)—R$_4$, —N(R$_3$) S(O$_2$)NR$_3$R$_4$, —C(O)OR$_4$, —C(O)R$_4$, —C(O)NR$_3$R$_4$, or —N(R$_3$)C(O)R$_4$; optionally substituted aryl; optionally substituted heteroaryl; optionally substituted heterocyclic; optionally substituted carbocyclic; or optionally substituted alkyl, optionally substituted alkenyl, or optionally substituted alkynyl, each containing 0, 1, 2, or 3 heteroatoms selected from O, S, or N; wherein at least one R$_1$ is halogen or —OR$_4$.

5. The compound of claim 1, or a pharmaceutically acceptable salt thereof, wherein each R$_1$ is independently halogen or —OR$_4$.

6. The compound of claim 1, or a pharmaceutically acceptable salt thereof, wherein
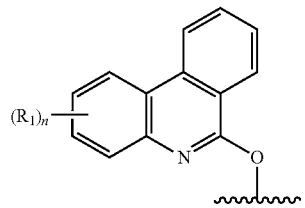
is selected from the following:
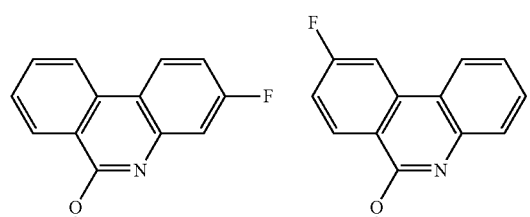
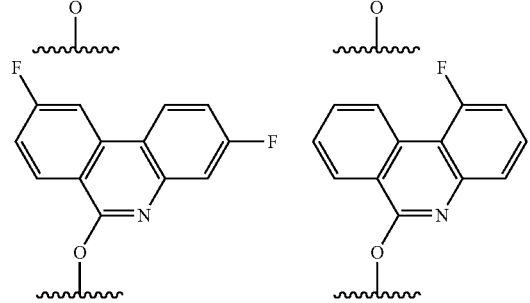
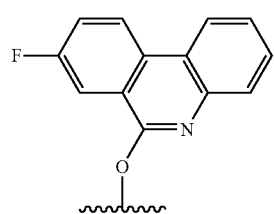
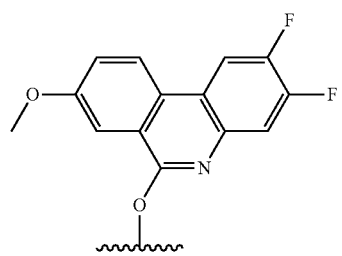
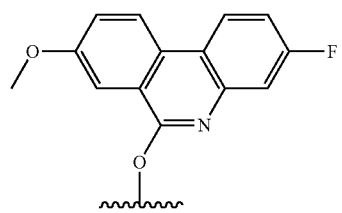
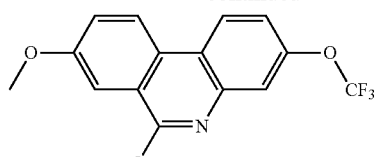
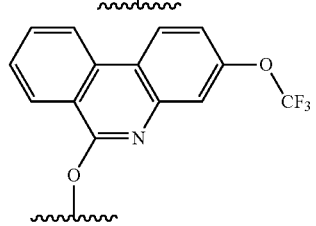
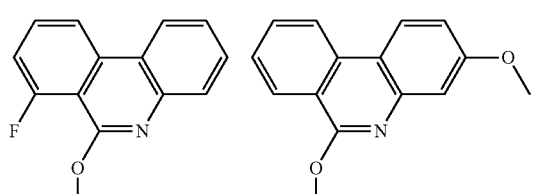
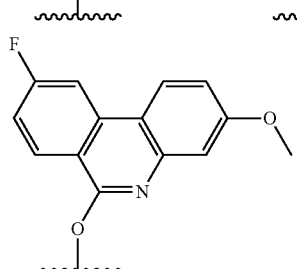
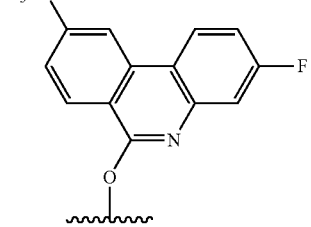
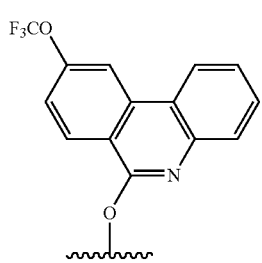
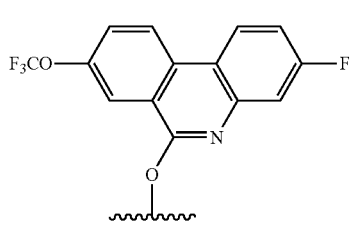

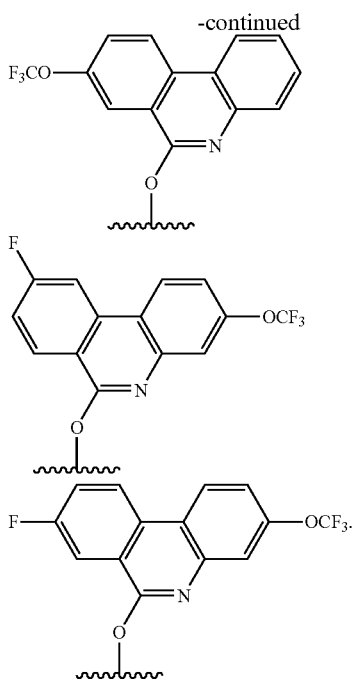

7. The compound of claim 1, or a pharmaceutically acceptable salt thereof, wherein k=3, j=1 and L is absent.

8. The compound of claim 1, of formula II, (II)

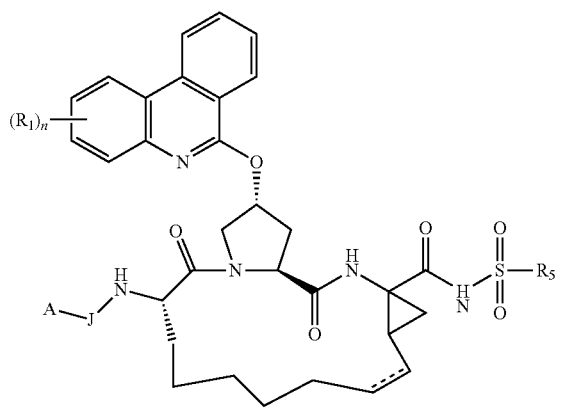

or a pharmaceutically acceptable salt thereof,
wherein:
J is absent, —C(O)—, —N(R$_3$)—C(O)—, —C(S)—, —C(=NR$_4$)—, —S(O)—, —S(O$_2$)—, or —N(R$_3$)—;
A is optionally substituted alkyl, optionally substituted alkenyl, or optionally substituted alkynyl, each containing 0, 1, 2, or 3 heteroatoms selected from O, S, or N; optionally substituted aryl, optionally substituted arylalkyl, optionally substituted alkoxy, optionally substituted heteroaryl, optionally substituted heterocyclic, or optionally substituted carbocyclic;
each R$_1$ is independently selected from
(i) halogen, hydroxy, amino, —OR$_4$, —N(R$_3$)S(O)$_2$—R$_4$, —N(R$_3$)(SO$_2$)NR$_3$R$_4$, —NR$_3$R$_4$, —C(O)—O—R$_4$, —C(O)R$_4$, —C(O)NR$_3$R$_4$, or —N(R$_3$)C(O)R$_4$;
(ii) optionally substituted aryl;
(iii) optionally substituted heteroaryl;
(iv) optionally substituted heterocyclic;
(v) optionally substituted carbocyclic; or
(vi) optionally substituted alkyl, optionally substituted alkenyl, or optionally substituted alkynyl, each containing 0, 1, 2, or 3 heteroatoms selected from O, S, or N;
wherein at least one of R$_1$ is halogen or —OR$_4$—;
R$_5$ is H; optionally substituted alkyl, optionally substituted alkenyl, or optionally substituted alkynyl, each containing 0, 1, 2, or 3 heteroatoms selected from O, S, or N; optionally substituted carbocyclic, optionally substituted heterocyclic, optionally substituted aryl, or optionally substituted heteroaryl;
R$_3$ and R$_4$ are each independently selected at each occurrence from the following:
optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;
n is 1, 2, 3, or 4; and
===== denotes a carbon-carbon single bond

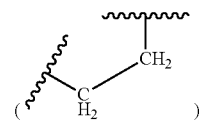

or double bond

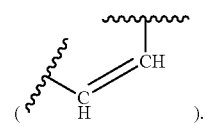

9. The compound of claim 8, or a pharmaceutically acceptable salt thereof, wherein R$_5$ is cyclopropyl, cyclobutyl, cyclopentyl, cyclohexyl, cycloheptyl, pyridinyl, pyrimidinyl, furanyl, thienyl, pyrrolyl, pyrazolyl, pyrrolidinyl, morpholinyl, piperidinyl, piperazinyl, or imidazolyl, each of which is optionally substituted.

10. The compound of claim 8, or a pharmaceutically acceptable salt thereof, wherein J is —C(O)— and A is optionally substituted —C$_1$-C$_8$ alkyl, containing 0, 1, 2, or 3 heteroatoms selected from O, S, or N; optionally substituted aryl, optionally substituted —C$_1$-C$_8$ alkoxy, optionally substituted heteroaryl, optionally substituted —C$_3$-C$_{12}$ cycloalkyl, or optionally substituted —C$_3$-C$_{12}$ heterocycloalkyl.

11. The compound of claim 8, or a pharmaceutically acceptable salt thereof, wherein A is selected from Me, Et, Pr, i-Pr, Bu, s-Bu, t-Bu,

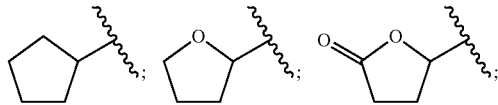

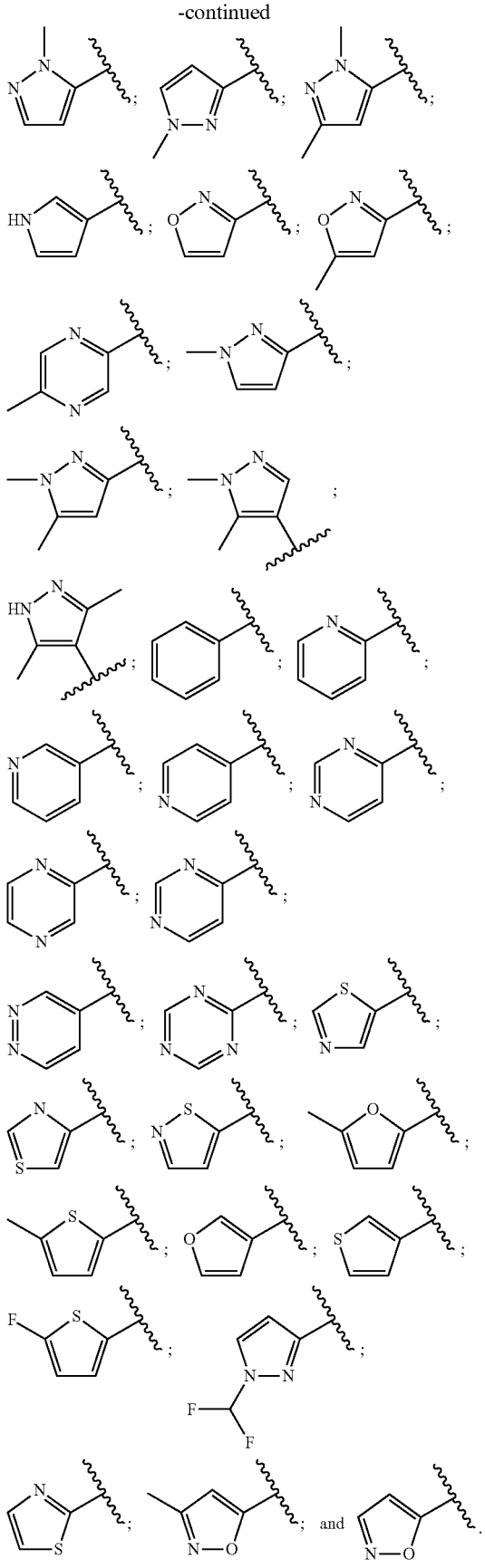

12. The compound of claim 8, or a pharmaceutically acceptable salt thereof, wherein A is

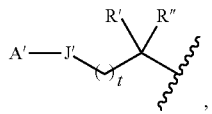

wherein:

J' is —NHC(O)—, —NHC(O)O—, —C(O)—, —O—C(O)—, —C(S)—, —S(O)—, —S(O$_2$)—;

A' is optionally substituted —C$_1$-C$_8$ alkyl, containing 0, 1, 2, or 3 heteroatoms selected from O, S, or N; optionally substituted —C$_1$-C$_8$ haloalkyl, optionally substituted aryl, optionally substituted —C$_1$-C$_8$ alkoxy, optionally substituted heteroaryl, optionally substituted —C$_3$-C$_{12}$ cycloalkyl, or optionally substituted —C$_3$-C$_{12}$ heterocyclyl;

R' is H, optionally substituted —C$_1$-C$_8$ alkyl, optionally substituted —C$_3$-C$_{12}$ cycloalkyl, optionally substituted aryl, optionally substituted heteroaryl, or optionally substituted C$_3$-C$_{12}$ heterocyclyl;

R" is H, optionally substituted —C$_1$-C$_8$ alkyl, optionally substituted —C$_3$-C$_{12}$ cycloalkyl, optionally substituted aryl, optionally substituted heteroaryl, or optionally substituted C$_3$—C$_{12}$ heterocyclyl; and t is 0 or 1.

13. The compound of claim 12, wherein J' is —NHC(O)—, or —NHC(O)O—; A' is optionally substituted —C$_1$-C$_8$ alkyl, containing 0, 1, 2, or 3 heteroatoms selected from O, S, or N; optionally substituted aryl, or optionally substituted heteroaryl; R' is H, optionally substituted —C$_1$-C$_8$ alkyl or optionally substituted —C$_3$-C$_{12}$ cycloalkyl; R" is H, and t is 0 or 1.

14. The compound of claim 13, wherein A' is Me, Et, Pr, i-Pr, Bu, s-Bu, t-Bu, cyclopropyl, cyclobutyl, cyclopentyl, cyclohexyl, cycloheptyl, pyridinyl, pyrimidinyl, furanyl, thienyl, pyrrolyl, pyrazolyl, pyrrolidinyl, morpholinyl, piperidinyl, piperazinyl, imidazolyl,

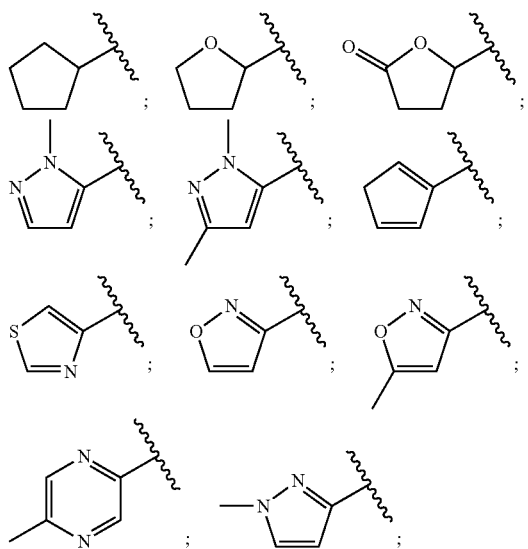

-continued

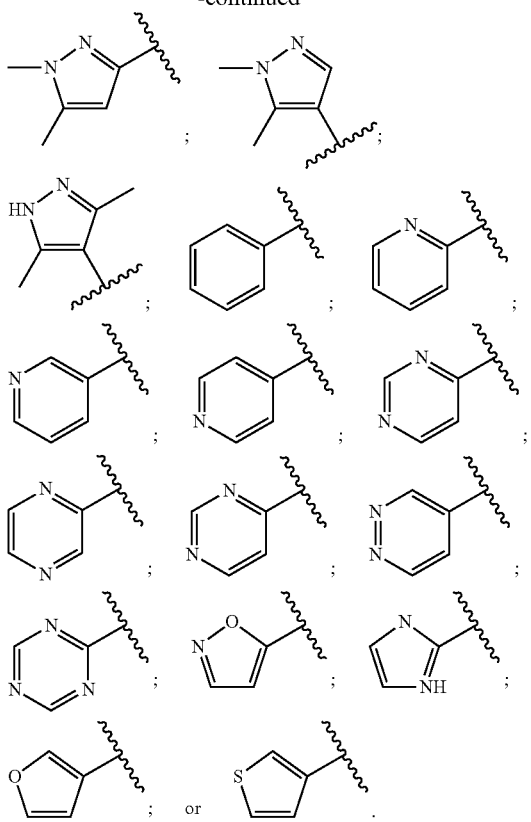

each of which is optionally substituted.

15. The compound of claim 8, wherein A is

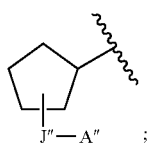

wherein,
J' is —NC(O)—, —NC(O)O—, —C(O)—, —O—C(O)—, —C(S)—, —C(=NR₄)—, —S(O)—, —S(O₂)—; and
A" is optionally substituted —$C_1$-$C_8$ alkyl, containing 0, 1, 2, or 3 heteroatoms selected from O, S, or N; optionally substituted —$C_1$-$C_8$ haloalkyl, optionally substituted aryl, optionally substituted —$C_1$-$C_8$alkoxy, optionally substituted heteroaryl, optionally substituted —$C_3$-$C_{12}$ cycloalkyl, or optionally substituted —$C_3$-$C_{12}$ heterocyclyl.

16. The compound of claim 8, wherein A is —CHR$_Z$(OH)—, wherein R$_Z$ is cyclohexyl, i-Pr, i-Bu, t-Bu, or CF$_3$.

17. The compound of claim 8, wherein, A is CHF$_2$—R$_Y$, wherein R$_Y$ is Ph or Et.

18. A pharmaceutical composition comprising a therapeutically effective amount of a compound of claim 1 or a pharmaceutically acceptable salt prodrug thereof, in combination with a pharmaceutically acceptable carrier or excipient.

19. A method of treating an HCV infection in a subject, comprising administering to the subject a therapeutically effective amount of a compound of claim 1 or a pharmaceutically acceptable salt thereof.

20. A method of producing a compound of claim 1, or a pharmaceutically acceptable salt thereof, comprising the step of reacting a compound of formula X:

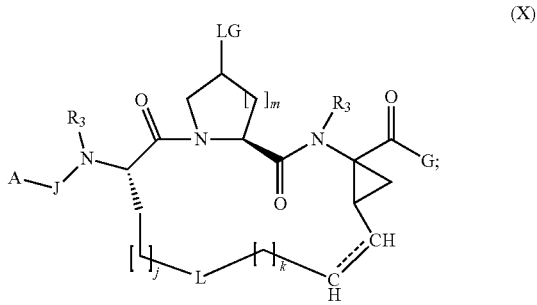

wherein,
J is absent, optionally substituted alkylene, optionally substituted alkenylene, optionally substituted alkynylene, —C(O)—, N(R₃)—C(O)—, —C(S)—, —C(=NR₄)—, —S(O)—, —S(O₂)—, or —N(R₃)—;
A is optionally substituted alkyl, optionally substituted alkenyl, or optionally substituted alkynyl, each containing 0, 1, 2, or 3 heteroatoms selected from O, S, or N; optionally substituted aryl, optionally substituted arylalkyl, optionally substituted alkoxy, optionally substituted heteroaryl, optionally substituted heterocyclic, or optionally substituted carbocyclic;
G is -E-R₅;
wherein E is absent; optionally substituted alkylene, optionally substituted alkenylene, optionally substituted alkynylene, each containing 0, 1, 2, or 3 heteroatoms selected from O, S, or N; or —O—, —S—, —N(R₃)—, —N(R₃)S(O)—, —N(R₃)C(O)—, —N(R₃) C(O)S(O)—, —OS(O)—, —C(O)S(O)—, or —C(O)N(R₃)S(O)—;
each p is independently 0, 1, or 2;
R₅ is H; optionally substituted alkyl, optionally substituted alkenyl, or optionally substituted alkynyl, each containing 0, 1, 2, or 3 heteroatoms selected from O, S, or N; optionally substituted carbocyclic, optionally substituted heterocyclic, optionally substituted aryl, or optionally substituted heteroaryl;
R₃ and R₄ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;
L is absent or is selected from optionally substituted alkylene, optionally substituted alkenylene or optionally substituted alkynylene, each containing 0, 1, 2, or 3 heteroatoms selected from O, S, or N;
j=0, 1, 2, 3, or 4;
k=0, 1, 2, or 3;
m=0, 1, or 2;
===== denotes a carbon-carbon single bond

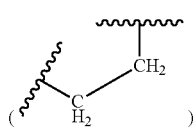

or double bond

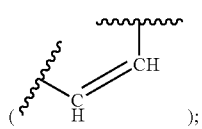 [SMILES: */C=C\*]

and
LG is a leaving group;
with a compound of formula XI:

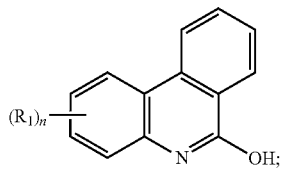

wherein:
each $R_1$ is independently selected from
(i) halogen, hydroxy, amino, —CN, —CF$_3$, —N$_3$, —NO$_2$, —OR$_4$, —SR$_4$, —SOR$_4$, —SO$_2$R$_4$, —N(R$_3$)S(O)$_2$—R$_4$, —N(R$_3$)(O$_2$)NR$_3$R$_4$, —NR$_3$R$_4$, —C(O)—O_R$_4$, —C(O)R$_4$, —C(O)NR$_3$R$_4$, or —N(R$_3$)C(O)R$_4$;
(ii) optionally substituted aryl;
(iii) optionally substituted heteroaryl;
(iv) optionally substituted heterocyclic;
(v) optionally substituted carbocyclic; or
(vi) optionally substituted alkyl, optionally substituted alkenyl, or optionally substituted alkynyl, each containing 0, 1, 2, or 3 heteroatoms selected from O, S, or N;
wherein at least one of $R_1$ is halogen or —OR$_4$—; and
n is 1, 2, 3, or 4;
to thereby produce a compound of formula I.

* * * * *